United States Patent
Wang et al.

(10) Patent No.: US 11,820,807 B2
(45) Date of Patent: Nov. 21, 2023

(54) IMMUNOGLOBULIN FUSION PROTEINS AND USES THEREOF

(71) Applicants: UBI Pharma Inc, Taipei (TW); Chang-Yi Wang, Cold Spring Harbor, NY (US)

(72) Inventors: Chang-Yi Wang, Cold Spring Harbor, NY (US); Wen-Jiun Peng, Hukou Township (TW); Wei-Ting Kao, Hukou Township (TW)

(73) Assignee: UBI PHARMA INC

( * ) Notice: Subject to any disclaimer, the term of this patent is extended or adjusted under 35 U.S.C. 154(b) by 0 days.

(21) Appl. No.: 15/177,605

(22) Filed: Jun. 9, 2016

(65) Prior Publication Data

US 2016/0362474 A1  Dec. 15, 2016

Related U.S. Application Data

(63) Continuation of application No. 15/002,396, filed on Jan. 20, 2016, now abandoned.

(60) Provisional application No. 62/175,186, filed on Jun. 12, 2015.

(51) Int. Cl.

| C07K 14/705 | (2006.01) |
| C07K 14/745 | (2006.01) |
| C07K 19/00 | (2006.01) |
| C07K 14/565 | (2006.01) |
| C07K 14/505 | (2006.01) |
| C07K 14/535 | (2006.01) |
| C07K 14/56 | (2006.01) |
| C07K 14/57 | (2006.01) |
| C12N 9/64 | (2006.01) |

(52) U.S. Cl.
CPC .......... *C07K 14/745* (2013.01); *C07K 14/505* (2013.01); *C07K 14/535* (2013.01); *C07K 14/56* (2013.01); *C07K 14/565* (2013.01); *C07K 14/57* (2013.01); *C07K 19/00* (2013.01); *C07K 2317/53* (2013.01); *C07K 2319/03* (2013.01); *C12N 9/644* (2013.01)

(58) Field of Classification Search
None
See application file for complete search history.

(56) References Cited

U.S. PATENT DOCUMENTS

| 5,116,964 | A |   | 5/1992 | Capon et al. |
| 5,624,821 | A |   | 4/1997 | Winter et al. |
| 5,807,734 | A | * | 9/1998 | Diegel ............. A61K 47/48561 |
|           |   |   |        | 424/134.1 |
| 6,030,613 | A |   | 2/2000 | Blumberg |
| 6,086,875 | A |   | 7/2000 | Blumberg |
| 6,485,726 | B1 |  | 11/2002 | Blumberg |
| 6,797,493 | B2 |  | 9/2004 | Sun et al. |
| 8,557,232 | B2 |  | 10/2013 | Gillies et al. |
| 8,846,874 | B2 | * | 9/2014 | Jung ...................... C07K 19/00 |
|           |   |   |        | 530/391.1 |
| 9,617,328 | B2 | * | 4/2017 | Lee ...................... C07K 14/745 |
| 2003/0235536 | A1 | | 12/2003 | Blumberg |
| 2014/0113370 | A1 | * | 4/2014 | Camphausen ......... C07K 14/78 |
|           |   |   |        | 435/328 |

FOREIGN PATENT DOCUMENTS

| WO | 1994/004689 | 3/1994 |
| WO | 2003/077834 | 9/2003 |

OTHER PUBLICATIONS

Capon, D.J., et al., "Designing CD4 immunoadhesins for AIDS therapy"; Nature 337: 525-531 (1989).
Chen, M., et al., "Regulatory effects of IFN-β on production of osteopontin and IL-17 by CD4+ T Cells in MS"; Eur. J. Immunol. 39: 2525-2536 (2009).
Goebl, N.A., et al., "Neonatal Fc Receptor Mediates Internalization of Fc in Transfected Human Endothelial Cells"; Mol. Biol. Cell, 19(12): 5490-5505 (2008).
Janeway, C.A., et al., Immunobiology, Garland Publishing, N.Y., N.Y (2001).
Junghans, R.P., et al., "The protection receptor for IgG catabolismis the beta2-microglobulin-containing neonatal intestinal transport receptor"; Proc Natl Acad Sci USA. 93(11): 5512-5516 (1996).
Ober, R.J., et al., "Exocytosis of IgG as mediated by the receptor, FcRn: an analysis at the single-molecule level"; Proc Natl Acad Sci USA. 101(30): 11076-11081 (2004).
Ober, R.J., et al., "Visualizing the site and dynamics of IgG salvage by the MHC class I-related receptor, FcRn"; J Immunol. 172(4): 2021-2029 (2004).
Osborn, B.L., et al., "Pharmacokinetic and pharmacodynamic studies of a human serum albumin-interferon-alpha fusion protein in cynomolgus monkeys"; J Pharmacol Exp Ther. 303(2): 540-548 (2002).
Peters, R.T., et al., "Prolonged activity of factor IX as a monomeric Fc fusion protein"; Blood. 115(10): 2057-2064 (2010).
Vaccaro, C., et al., "Engineering the Fc region of immunoglobulin G to modulate in vivo antibody levels"; Nat Biotechnol. 23(10): 1283-1288 (2005).

(Continued)

*Primary Examiner* — Michael D Pak

(74) *Attorney, Agent, or Firm* — Locke Lord LLP; Peter N. Fill; Nicholas J. DiCeglie, Jr.

(57) ABSTRACT

A fusion protein is disclosed. The fusion protein of the invention comprises an Fc fragment of an immunoglobulin G and a bioactive molecule, wherein the Fc is a single chain Fc. The amino acids in the hinge of the Fc is mutated, substituted, or deleted so that the hinge of Fc cannot form disulfide bonds. Methods for producing and using the fusion protein of the invention are also provided.

4 Claims, 20 Drawing Sheets

Specification includes a Sequence Listing.

(56) References Cited

OTHER PUBLICATIONS

U.S. Food and Drug Administration website. (http://www.fda.gov/forconsumers/byaudience/forpatientadvocates/ucm151494.htm) Web Archived version of the webpage from Jun. 25, 2014 accessed Jan. 27, 2016 from: http://web.archive.org/web/20140625151058/http://www.fda.gov/ForConsumers/ByAudience/ForPatientAdvocates/ucm151494.htm.

* cited by examiner

US 11,820,807 B2

IMMUNOGLOBULIN FUSION PROTEINS AND USES THEREOF

This application is a continuation of U.S. application Ser. No. 15/002,396, filed Jan. 20, 2016, which claims the benefit of U.S. Provisional Application Ser. No. 62/175,186, filed Jun. 12, 2015, all of which are incorporated herein by reference in their entireties.

FIELD OF THE INVENTION

The present invention relates to a therapeutic fusion protein comprising an Fc fragment of an immunoglobulin G and a bioactive molecule, wherein the Fc fragment is a single chain.

BACKGROUND OF THE INVENTION

An immunoglobulin comprises four polypeptide chains, two heavy chains and two light chains, that associate via interchain disulfide bonds. Each light chain has two domains, a variable light domain ($V_L$) and a constant light domain ($C_L$); and each heavy chain has two regions, a variable heavy region ($V_H$) and a constant heavy region ($C_H$). The constant heavy region ($C_H$) is composed of constant heavy domains that are designated by number (e.g., $C_H1$, $C_H2$, $C_H3$, etc.) (see e.g., U.S. Pat. No. 6,086,875 (Blumberg R. S. et al.); U.S. Pat. No. 5,624,821 (Winter G. P. et al.); and U.S. Pat. No. 5,116,964 (Capon D. J. and Lasky L. A.)). Immunoglobulins are categorized into different isotypes based on their biological properties, location in an organism, and ability to deal with different antigens (i.e., IgG, IgM, IgA, IgD and IgE). Depending on the immunoglobulin isotype, the constant heavy region ($C_H$) can have three or four $C_H$ domains. Also, in some isotypes (IgA, IgD, and IgG), the heavy chains contain a hinge region that adds flexibility to the molecule (Janeway et al. 2001, *Immunobiology*, Garland Publishing, N.Y., N.Y.).

There are four IgG subclasses (IgG1, 2, 3, and 4) in humans, named in order of their abundance in serum (IgG1 being the most abundant). The IgG isotype, is composed of two light chains and two heavy chains, where each heavy chain contains three constant heavy domains ($C_H1$, $C_H2$, $C_H3$). The two heavy chains of IgG are linked to each other and to a light chain each by disulfide bonds (—S—S—). The antigen binding site of IgG is located in the Fragment antigen binding region (Fab region), which contains variable light ($V_L$) and variable heavy ($V_H$) chain domains as well as constant light ($C_L$) and constant heavy ($C_H1$) chain domains. The fragment crystallizable region (Fc region) of IgG is a portion of the heavy chain containing the $C_H2$ and $C_H3$ domains that binds to an Fc receptor found on the surface of certain cells, including the neonatal Fc receptor (FcRn). The heavy chain of IgG also has a hinge region (hinge) between the $C_H1$ and $C_H2$ domains that separates the Fab region from the Fc region and participates in linking the two heavy chains together via disulfide bonds. The structure of the hinge region contributes to unique biological properties of each of the four IgG subclasses.

IgG is secreted as a monomer that is small in size allowing it to easily perfuse tissues. It is the only isotype that has receptors (neonatal Fc receptor (FcRn)) that facilitate passage through the human placenta to provide protection to the fetus in utero. IgG absorbed through the placenta provides the neonate with humoral immunity before its own immune system develops.

The IgG neonatal Fc receptor (FcRn) binding site is located in the Fc region of the antibody. FcRn is normally expressed in human placenta and epithelial cells and participates in an endocytic salvage pathway that prevents degradation of IgG. This salvage pathway is mediated by the highly pH-dependent binding affinity of IgG to FcRn in acidic pH. The high affinity of IgG for FcRn at acidic pH is believed to result in binding of internalized IgG to FcRn after uptake into acidic endosomes (Goebl N A, et al, 2008; Junghans R P, et al, 1996). Although most soluble proteins are directed to lysosomes after internalization, internalized FcRn-bound IgG returns to the plasma membrane and is effectively rescued from the default degradative pathway. Upon exposure to the neutral pH of the extracellular space, IgG can then dissociate from FcRn and return to circulation. Thus, the extended serum half-life property of the antibody is retained in the Fc fragment.

This salvage pathway provides one mechanism for developing next-generation protein drugs that have a prolonged half-life in blood circulation compared to unmodified protein drugs. In particular, unmodified protein drugs have a short circulating half-life, making frequent dosing over an extended treatment period necessary. Extensive efforts have been made to extend the half-life of the protein drugs by many means including PEGylation fusion protein technologies (U.S. Food and Drug Administration; Osborn B L, et al, 2002); however, the results from these efforts have not been ideal.

The creation of fusion proteins comprising IgG constant regions linked to a protein of interest, or fragment thereof, has been described. For example, protein "X" of interest is linked to an IgG "Fc" domain to create an "Fc-X" or "X-Fc" fusion protein (immunofusion). Immunofusion proteins can generally be prepared and purified in larger quantities compared to other types of fusion proteins because the Fc moiety of the fusion protein is designed for efficient secretion by the cell. Fusion proteins containing a Fc region of an immunoglobulin have been shown to have enhanced features compared to their non-Fc-containing counterparts, including increased protein stability and longer serum half-life (see Capon et al. 1989, *Nature* 337:525), as well as an ability to bind to Fc receptors such as the neonatal Fc receptor (FcRn) (see e.g., U.S. Pat. No. 6,086,875 (Blumberg R. S. et al.); U.S. Pat. No. 6,485,726 (Blumberg R. S. et al.); U.S. Pat. No. 6,030,613; WO 03/077834 (Blumberg R. S. et al.); and US 2003-0235536A1 (Blumberg R. S. et al.)). The following patent documents describe additional examples.

U.S. Pat. No. 5,116,964 (Capon D. J. and Lasky L. A.) discloses a ligand binding partner protein which comprises a lymphocyte cell surface glycoprotein (LHR) and an immunoglobulin chain, in which the ligand binding partner protein and immunoglobulin are fused through either N-terminus amino or C-terminus carboxyl group.

WO 94/04689 (Pastan I. H. et al.) discloses the use of Fc of immunoglobulin to provide a toxin with extended half-life that includes a ligand binding domain (CD4 receptor) and a *Pseudomonas* exotoxin A. The IgG Fc links the CD4 receptor and a *Pseudomonas* exotoxin A.

U.S. Pat. No. 6,797,493 (Sun L-H. et al.) discloses a hG-CSF-L-vFc fusion protein comprising human granulocyte colony-stimulating factor (hG-CSF), a flexible peptide linker (L) of about 20 or fewer amino acids, and a human IgG Fc variant. The Fc variant is of a non-lytic nature and shows minimal undesirable Fc-mediated side effects.

U.S. Pat. No. 8,557,232 (Gillies S. D. et al.) discloses a method and composition for expressing soluble, biologically active Fc-IFN-β fusion proteins and variants thereof (Fc- IFN-β$^{sol}$). The Fc-IFN-β fusion protein includes an IFN-β protein linked to the carboxy-terminus of the immunoglobulin Fc region The above documents describe fusion proteins having a two chain Fc fusion protein design with two bioactive molecules in close proximity to one another. The bioactive molecules of these traditional fusion proteins are generally suppressed or sterically hindered from interacting with the target molecules or cells. Therefore, there is a need to develop a fusion protein comprising a bioactive molecule linked to a modified Fc region of an IgG, that can confer increased in vivo half-life of the bioactive molecules without suppressing the bioactivity of the bioactive molecule. Such modified fusion proteins would provide an added benefit for ease of purification by related affinity purification processes.

REFERENCES

1. Blumberg R. S. et al., "Receptor specific transepithelialus transport of therapeutics" U.S. Pat. No. 6,030,613 (2000), U.S. Pat. No. 6,086,875 (2000), and U.S. Pat. No. 6,485,726 (2002)
2. Blumberg R. S. et al., "Central airway administration for systemic delivery of therapeutics" WO 03/077834 (2002) and US Patent Application 2003-0235536A1 (2003)
3. Capon D. J., et al., "Designing CD4 immunoadhesins for AIDS therapy" Nature 337:525 (1989)
4. Capon D. J. and Lasky L. A., "Hybrid immunoglobulins" U.S. Pat. No. 5,116,964 (1992)
5. Gillies S. D. et al., "Stabilization of Fc-interferon-beta fusion proteins" U.S. Pat. No. 8,557,232 (2013)
6. Goebl N. A., et al, "Neonatal Fc Receptor Mediates Internalization of Fc in Transfected Human Endothelial Cells" Mol. Biol. Cell, 19(12): 5490-5505 (2008)
7. Janeway et al., Immunobiology, Garland Publishing, N.Y., N.Y. (2001)
8. Junghans R. P., et al., "The protection receptor for IgG catabolism is the beta2-microglobulin-containing neonatal intestinal transport receptor" Proc Natl Acad Sci USA. 93(11): 5512-5516 (1996)
9. Ober R. J. et al, Exocytosis of IgG as mediated by the receptor, FcRn: an analysis at the single-molecule level. Proc Natl Acad Sci USA. 101(30): 11076-81 (2004)
10. Ober R. J. et al., Visualizing the site and dynamics of IgG salvage by the MHC class I-related receptor, FcRn. J Immunol. 172(4):2021-9 (2004)
11. Osborn B. L. et al., "Pharmacokinetic and pharmacodynamic studies of a human serum albumin-interferon-alpha fusion protein in cynomolgus monkeys." J Pharmacol Exp Ther. 303(2): 540-8 (2002)
12. Pastan I. H., et al, "Recombinant toxin with increased half-life" WO 94/04689 (1993)
13. Peters R. T. et al., Prolonged activity of factor IX as a monomeric Fc fusion protein. Blood. 115(10):2057-64 (2010)
14. Sun L.-H. et al., "Fc fusion proteins of human granulocyte colony-stimulating factor with increased biological activities" U.S. Pat. No. 6,797,493 (2004)
15. Winter G P. et al., "Antibodies with altered effector functions" U.S. Pat. No. 5,624,821 (1997)
16. Vaccaro C, et al., Engineering the Fc region of immunoglobulin G to modulate in vivo antibody levels. Nat Biotechnol. 23(10):1283-8 (2005)

SUMMARY OF THE INVENTION

The present disclosure is directed to novel fusion proteins comprising a portion of an immunoglobulin (Ig) molecule, compositions thereof, and methods for making and using the disclosed fusion proteins. The disclosed fusion proteins are useful for extending the serum half-life of bioactive molecules in an organism.

One aspect of the present disclosure relates to a fusion protein, hybrid, conjugate and compositions thereof. The fusion protein of the present disclosure generally comprises (a) bioactive molecule and (b) a portion of a constant heavy region ($C_H$) derived from an Ig molecule (the Ig fragment). The Ig fragment can include any portion of the constant heavy region, including one or more constant heavy domains, a hinge region, an Fc region, and/or combinations thereof. The amino acid sequence of the (a) bioactive molecule and (b) Ig fragment of the fusion protein are derived from the wild-type sequence of each fragment, as disclosed in the art. Derived sequences include the wild-type sequence as well as homologues, analogues, fragments, and other variants of the wild-type sequence.

In certain embodiments, the Ig fragment of the fusion protein comprises a single chain Fc (sFc or scFc), a monomer, that is incapable of forming a dimer. In some embodiments, the fusion protein includes a sequence corresponding to an immunoglobulin hinge region. In various embodiments, the hinge region contains a modification that prevents the fusion protein from forming a disulfide bond with another fusion protein or another immunoglobulin molecule. In some embodiments, the hinge region is modified by mutating and/or deleting one or more cysteine amino acids to prevent the formation of a disulfide bond. In some embodiments, the bioactive molecule is linked to the scFc through a hinge region. In specific embodiments, the fusion protein comprises the bioactive molecule at its N-terminus that is linked to a scFc through a mutated hinge region. In certain embodiments, the present invention relates to compositions, including pharmaceutical compositions, comprising the fusion protein and a pharmaceutically acceptable carrier or excipient.

Another aspect of the present invention relates to methods for making and using a fusion protein and compositions thereof. In some embodiments, the method for making the fusion protein comprises (i) providing a bioactive molecule, an Fc fragment, and a hinge region, (ii) modifying the hinge region to prevent it from forming a disulfide bond, and (iii) linking the bioactive molecule to the Fc fragment through the mutated hinge region to form the fusion protein, hybrid, conjugate, or composition thereof. The present disclosure also provides a method for purifying the fusion protein, comprising (i) providing a fusion protein, and (ii) purifying the fusion protein by Protein A or Protein G-based chromatography media.

Detailed description of the invention is given in the following embodiments with reference to the accompanying drawings.

BRIEF DESCRIPTION OF THE DRAWINGS

FIG. 1A illustrates a fusion protein comprising a biologically active molecule at the N-terminus that is covalently linked to a hinge region and Fc fragment ($C_H2$ and $C_H3$ domains) of human IgG. FIG. 1B illustrates a fusion protein comprising a biologically active molecule at the N-terminus that is covalently linked to a hinge region and Fc fragment ($C_H2$ and $C_H3$ domains) of human IgG through a linker. FIG. 1C illustrates a fusion protein comprising a biologically active molecule at the C-terminus that is covalently linked to a hinge region and Fc fragment ($C_H2$ and $C_H3$ domains) of human IgG. FIG. 1D illustrates a fusion protein comprising a biologically active molecule at the C-terminus that is covalently linked to a hinge region and Fc fragment ($C_H2$ and $C_H3$ domains) of human IgG through a linker.

DETAILED DESCRIPTION OF THE INVENTION

The present disclosure is directed to novel fusion proteins comprising a bioactive molecule and portions of an immunoglobulin molecule. Various aspects of the present disclosure relate to fusion proteins, compositions thereof, and methods for making and using the disclosed fusion proteins. The disclosed fusion proteins are useful for extending the serum half-life of bioactive molecules in an organism.

The following is a detailed description provided to aid those skilled in the art in practicing the present invention. Those of ordinary skill in the art would understand that modifications or variations of the embodiments expressly described herein, which do not depart from the spirit or scope of the information contained herein, are encompassed by the present disclosure. The terminology used in the description is for describing particular embodiments only and is not intended to be limiting of the invention. The section headings used below are for organizational purposes only and are not to be construed as limiting the subject matter described.

All publications, patent applications, patents, figures and other references mentioned herein are incorporated by reference in their entireties as if disclosed and recited completely in the specification.

1. FUSION PROTEIN

As used herein, "fusion protein" or a "fusion polypeptide" is a hybrid protein or polypeptide comprising at least two proteins or peptides linked together in a manner not normally found in nature.

One aspect of the present disclosure is directed to a fusion protein comprising an immunoglobulin (Ig) Fc fragment and a bioactive molecule. The bioactive molecule that is incorporated into the disclosed fusion protein has improved biological properties compared to the same bioactive molecule that is either not-fused or incorporated into a fusion protein described in the prior art (e.g., fusion proteins containing a two chain Fc region). For example, the bioactive molecule incorporated into the disclosed fusion protein has a longer serum half-life compared to its non-fused counterpart. Additionally, the disclosed fusion protein maintains full biological activity of the bioactive molecule without any functional decrease, which is an improvement over the fusion proteins of the prior art that have a decrease in activity due to steric hindrance from a two chain Fc region.

The fusion proteins of the present disclosure provide significant biological advantages to bioactive molecules compared to non-fused bioactive molecules and bioactive molecules incorporated into fusion proteins described in the prior art.

Figure 1A:
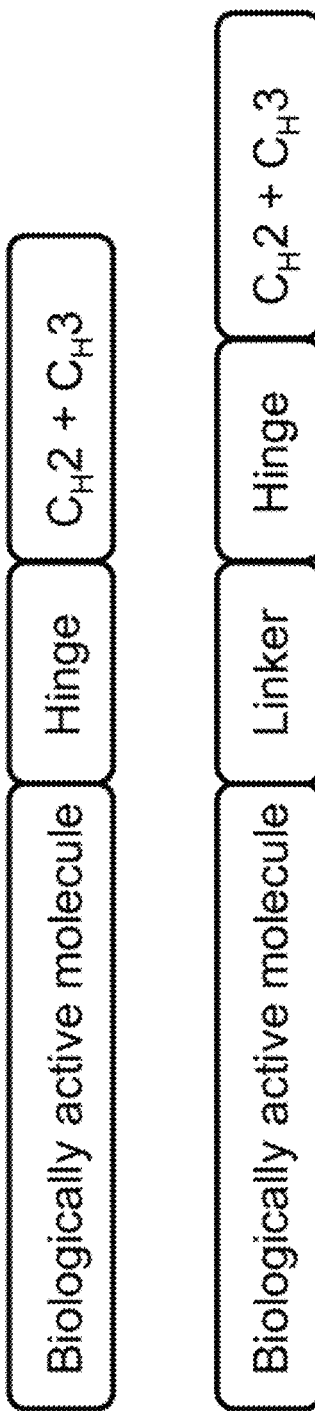
FIGS. 1A to 1D illustrate the design of a single chain fusion protein according to various embodiments of the present disclosure.

The disclosed fusion protein can have any of the following formulae (also shown in FIGS. 1A to 1D):

(B)-(Hinge)-($C_H2$-$C_H3$)      (Formula 1) (FIG. 1A)

Figure 1B:

($C_H3$-$C_H2$)-(Hinge)-(B)      (Formula 2) (FIG. 1B)

Figure 1C:
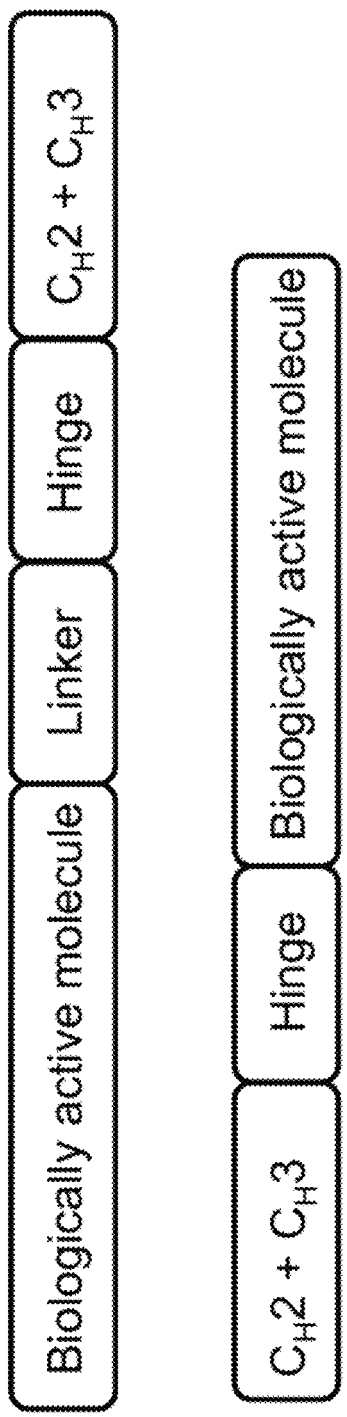

(B)-(L)$_m$-(Hinge)-($C_H2$-$C_H3$); or      (Formula 3) (FIG. 1C)

Figure 1D:
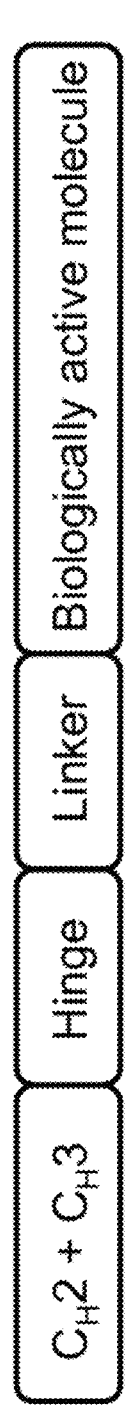

($C_H3$-$C_H2$)-(Hinge)-(L)$_m$-(B)      (Formula 4) (FIG. 1D)

wherein
"B" is a bioactive molecule;
"Hinge" is a hinge region of an IgG molecule;
"$C_H2$-$C_H3$" is the $C_H2$ and $C_H3$ constant region domains of an IgG heavy chain;
"L" is an optional linker; and
"m" may be an any integer or 0.

The various portions/fragments of the fusion protein are discussed further below.

a. Fc Region and Fc Fragment

The fusion protein of the present disclosure contains an Fc fragment from an immunoglobulin (Ig) molecule.

As used below, "Fc region" refers to a portion of an immunoglobulin located in the c-terminus of the heavy chain constant region. The Fc region is the portion of the immunoglobulin that interacts with a cell surface receptor (an Fc receptor) and other proteins of the complement system to assist in activating the immune system. In IgG, IgA and IgD isotypes, the Fc region contains two heavy chain domains ($C_H2$ and $C_H3$ domains). In IgM and IgE isotypes, the Fc region contains three heavy chain constant domains ($C_H2$ to $C_H4$ domains). Although the boundaries of the Fc portion may vary, the human IgG heavy chain Fc portion is usually defined to comprise residues C226 or P230 to its carboxyl-terminus, wherein the numbering is according to the EU index.

In certain embodiments, the fusion protein comprises a $C_H2$-$C_H3$ domain, which is an FcRn binding fragment, that can be recycled into circulation again. Fusion proteins having this domain demonstrate an increase in the in vivo half-life of the fusion proteins.

As used herein, "Fc fragment" refers to the portion of the fusion protein that corresponds to an Fc region of an immunoglobulin molecule from any isotype. In some embodiments, the Fc fragment comprises the Fc region of IgG. In specific embodiments, the Fc fragment comprises the full-length region of the Fc region of IgG1. In some embodiments, the Fc fragment refers to the full-length Fc region of an immunoglobulin molecule, as characterized and described in the art. In other embodiments, the Fc fragment includes a portion or fragment of the full-length Fc region, such as a portion of a heavy chain domain (e.g., $C_H2$ domain, $C_H3$ domain, etc.) and/or a hinge region typically found in the Fc region. For example, the Fc fragment of can comprise all or part of the $C_H2$ domain and/or all or part of the $C_H3$ domain. In some embodiments, the Fc fragment includes a functional analogue of the full-length Fc region or portion thereof.

As used herein, "functional analogue" refers to a variant of an amino acid sequence or nucleic acid sequence, which retains substantially the same functional characteristics (binding recognition, binding affinity, etc.) as the original sequence. Examples of functional analogues include sequences that are similar to an original sequence, but contain a conservative substitution in an amino acid position; a change in overall charge; a covalent attachment to another moiety; or small additions, insertions, deletions or conservative substitutions and/or any combination thereof. Functional analogues of the Fc fragment can be synthetically produced by any method known in the art. For example, a functional analogue can be produced by modifying a known amino acid sequence by the addition, deletion, and/or substitution of an amino acid by site-directed mutation. In some embodiments, functional analogues have an amino acid sequence that is at least 50%, 55%, 60%, 65%, 70%, 75%, 80%, 85%, 90%, 92%, 95% 96%, 97%, 98%, or 99% identical to a given sequence. Percent identity between two sequences is determined by standard alignment algorithms such as ClustalX when the two sequences are in best alignment according to the alignment algorithm.

The immunoglobulin molecule can be obtained or derived from any animal (e.g., human, cows, goats, swine, mice, rabbits, hamsters, rats, guinea pigs). Additionally, the Fc fragment of the immunoglobulin can be obtained or derived from any isotype (e.g., IgA, IgD, IgE, IgG or IgM) or subclass within an isotype (IgG1, IgG2, IgG3, and IgG4). In some embodiments, the Fc fragment is obtained or derived from IgG and, in particular embodiments, the Fc fragment is obtained or derived from human IgG, including humanized IgG.

The Fc fragment can be obtained or produced by any method known in the art. For example, the Fc fragment can be isolated and purified from an animal, recombinantly expressed, or synthetically produced. In some embodiments, the Fc fragment is encoded in a nucleic acid molecule (e.g., DNA or RNA) and isolated from a cell, germ line, cDNA library, or phage library.

The Fc region and/or Fc fragment can include a hinge region found in some immunoglobulin isotypes (IgA, IgD, and IgG). In certain embodiments, the Fc fragment is modified by mutating the hinge region so that it does not contain any Cys and cannot form disulfide bonds. The hinge region is discussed further below.

The Fc fragment of the disclosed fusion protein is preferably a single chain Fc. As used herein, "single chain Fc" (of "sFc") means that the Fc fragment is modified in such a manner that prevents it from forming a dimer (e.g., by chemical modification or mutation addition, deletion, or substation of an amino acid).

In certain embodiments, the Fc fragment of the fusion protein is derived from human IgG1, which can include the wild-type human IgG1 amino acid sequence or variations thereof. In some embodiments, the Fc fragment of the fusion protein contains an Asn amino acid that serves as an N-glycosylation site at amino acid position 297 of the native human IgG1 molecule (based on the European numbering system for IgG1, as discussed in U.S. Pat. No. 7,501,494), which corresponds to residue 67 in the Fc fragment (SEQ ID NO: 61). In other embodiments, the N-glycosylation site in the Fc fragment is removed by mutating the Asn (N) residue with His (H) (SEQ ID NO: 62) or Ala (A) (SEQ ID NO: 63). An Fc fragment containing a variable position at the N-glycosylation site is shown as SEQ ID NO: 64 in the Sequence Listing.

In some embodiments, the $C_H3$-$C_H2$ domain of the Fc fragment has an amino acid sequence corresponding to the wild-type sequence (disclosed in SEQ ID NO: 61). In certain embodiments, the $C_H3$-$C_H2$ domain of the Fc fragment has the amino acid sequence of SEQ ID NO: 62, where the N-glycosylation site is removed by mutating the Asn (N) residue with His (H). In certain embodiments, the $C_H3$-$C_H2$ domain of the Fc fragment has the amino acid sequence of SEQ ID NO: 63, where the N-glycosylation site is removed by mutating the Asn (N) residue with Ala (A).

b. Hinge Region

The disclosed fusion protein can include a hinge region found in some immunoglobulin isotypes (IgA, IgD, and IgG). The hinge region separates the Fc region from the Fab region, and adds flexibility to the molecule, and can link two heavy chains via disulfide bonds. Formation of a dimer, comprising two $C_H2$-$C_H3$ domains, is required for the functions provided by intact Fc regions. Interchain disulfide bonds between cysteines in the wild-type hinge region help hold the two chains of the Fc molecules together to create a functional unit.

In certain embodiments, the hinge region is be derived from IgG, preferably IgG1. The hinge region can be a full-length or a modified (truncated) hinge region.

In specific embodiments, the hinge region contains a modification that prevents the fusion protein from forming a disulfide bond with another fusion protein or an immunoglobulin molecule. In specific embodiments, the hinge region is modified by mutating and/or deleting one or more cysteine amino acids to prevent the formation of a disulfide bond. The N-terminus or C-terminus of the full-length hinge region may be deleted to form a truncated hinge region. In order to avoid the formation of disulfide bonds, the cysteine (Cys) in the hinge region can be substituted with a non-Cys amino acid or deleted. In specific embodiments, the Cys of hinge region may be substituted with Ser, Gly, Ala, Thr, Leu, Ile, Met or Val. Examples of wild-type and mutated hinge regions from IgG1 to IgG4 include the amino acid sequences shown in Table 1 (SEQ ID NOs: 1 to 22). Disulfide bonds cannot be formed between two hinge regions that contain mutated sequences. The IgG1 hinge region was modified to accommodate various mutated hinge regions with sequences shown in Table 2 (SEQ ID NOs: 23-60).

c. Linker

The fusion protein may have the bioactive molecule linked to the N-terminus of the Fc fragment. Alternatively, the fusion protein may have the bioactive molecule linked to the C-terminus of the Fc fragment. The linkage is a covalent bond, and preferably a peptide bond.

In the present invention, one or more bioactive molecule may be directly linked to the C-terminus or N-terminus of the Fc fragment. Preferably, the bioactive molecule(s) can be directly linked to the hinge of the Fc fragment.

Additionally, the fusion protein may optionally comprise at least one linker. Thus, the bioactive molecule may not be directly linked to the Fc fragment. The linker may intervene between the bioactive molecule and the Fc fragment. The linker can be linked to the N-terminus of the Fc fragment or the C-terminus of the Fc fragment.

In one embodiment, the linker includes amino acids. The linker may includes 1-5 amino acids.

d. Bioactive Molecule

As used herein, the term "biologically active molecule" refers to proteins, glycoproteins, and combinations thereof. Examples of biologically active substances include anti-angiogenesis factors, cytokines, growth factors, hormones, enzymes, receptors thereof, and fragments thereof.

Examples of biologically active cytokines include, but are not limited to: interleukins (IL) (e.g., IL-1, IL-2, IL-3, IL-4, IL-5, IL-6, IL-7, IL-8, IL-9, IL-10, IL-11, IL-12, IL-13, IL-14, IL-15, IL-16, IL-17, IL-18); macrophage inflammatory proteins (e.g., MIP1α, MIP1β); macrophage colony stimulating factor; granulocyte macrophage colony stimulating factor; interferons (IFNs) (e.g., interferon α, interferon β, interferon γ); tumor necrosis factors (e.g., TNF-alpha, TNF-beta), lymphokine inhibitory factor; platelet derived growth factor; stem cell factor; tumor growth factor β; lymphotoxin; Fas; erythropoietin (EPO); leukemia inhibitory factor; oncostatin-M; ciliary neurotrophic factor; prolactin; CD40-ligand; CD27-ligand; and CD30-ligand; colony stimulating factors and growth factors including granulocyte and/or macrophage stimulating factors (GM-CSF, G-CSF and CSF-1); and platelet derived, epidermal, insulin-like, transforming and fibroblast growth factors. Biologically active cytokines also include receptors and/or fragments thereof. The biologically active cytokines also include those previously described (see e.g., U.S. Pat. Nos. 6,086,875, and 6,485,726).

Examples of growth factors, protein hormones, and receptors thereof which may be delivered via an FcRn binding partner include, but are not limited to, erythropoietin (EPO), angiogenin, hepatocyte growth factor, fibroblast growth factor, keratinocyte growth factor, nerve growth factor, tumor growth factor α, thrombopoietin, thyroid stimulating factor, thyroid releasing hormone, neurotrophin, epidermal growth factor, VEGF, ciliary neurotrophic factor, LDL, somatomedin, insulin growth factor, insulin-like growth factor I and II. The biologically active growth factors also include those previously described (see e.g., U.S. Pat. Nos. 6,086,875, and 6,485,726).

In certain embodiments, the biologically active molecule contemplated by the invention includes erythropoietin (EPO), Factor IX (FIX), interferons (IFNs), and granulocyte colony stimulating factor (G-CSF or GCSF).

In one embodiment, the biologically active molecule is erythropoietin (EPO). Erythropoietin, an acidic glycoprotein of approximately 34,000 dalton molecular weight, is a glycoprotein hormone involved in the maturation of erythroid progenitor cells into erythrocytes. It is essential in regulating levels of red blood cells in circulation. Naturally occurring erythropoietin is produced by the liver during fetal life and by the kidney of adults and circulates in the blood and stimulates the production of red blood cells in bone marrow. See, Erythropoietin concentrated solution of European Pharmacopoeia. In a specific embodiment, the EPO protein has an amino acid sequence of SEQ ID NO: 65.

In another embodiment, the biologically active molecule is Factor IX (FIX). FIX, a globular protein which has a molecular weight of about 70,000 daltons, is a vitamin K-dependent protein which participates in blood coagulation. It is synthesized in the form of a zymogen and undergoes three types of post-translational modifications before being secreted into the blood. In man, the liver is the site of FIX synthesis. This protein participates in the blood coagulation cycle and is used for the treatment of hemophilia B patients. At the present time the only commercially available source of FIX is human plasma. See, Human coagulation Factor IX of European Pharmacopoeia. In a specific embodiment, the FIX protein has an amino acid sequence of SEQ ID NO: 67.

In other embodiments, the biologically active molecule is Interferon alpha (IFNα) or Interferon beta (IFNβ). Interferons (IFNs) are glycoproteins (19-20 KDa), possessing antiviral, immunomodulatory and anti-proliferative effects and are divided in to three classes (Types I, II and III) according to their structural homology and the specific receptor they associate with. The type I IFN family includes numerous IFN alpha variants, a single IFN beta member, and lesser known IFN epsilon, kappa, omega and delta. However, all type I IFNs bind exclusively to the IFN alpha receptor (IFNAR). IFN alphas are produced by leukocytes in response to different stimuli whereas IFN beta is produced by most cell types except leukocytes. IFN beta has 30% amino-acid homology with IFN alpha but with higher binding affinity to IFNAR when compared to IFN alpha. IFN alpha and beta are used in the treatment of various human cancers and disease of viral origin. In a specific embodiment, the IFNα protein is IFNα8 having an amino acid sequence of SEQ ID NO: 69. In a specific embodiment, the IFNβ protein has an amino acid sequence of SEQ ID NO: 73.

In another embodiment, the biologically active molecule is granulocyte colony stimulating factor (GCSF). Granulocyte colony stimulating factor (GCSF) is a 20 KDa glycoprotein with a 174- or 177-amino acids single polypeptide chain. The shorter form possesses greater activity and stability than the longer isoform and is the basis for commercial pharmaceutical GCSF products. GCSF stimulates the proliferation of neutropenic progenitor cells and their differentiation into granulocytes, and also activates mature neutrophils. GCSF is most frequently used in the treatment of chemotherapy-induced neutropenia. In a specific embodiment, the GCSF protein has an amino acid sequence of SEQ ID NO: 71.

2. COMPOSITIONS

In certain embodiments, the present invention relates to compositions, including pharmaceutical compositions, comprising the fusion protein and a pharmaceutically acceptable carrier or excipient.

Pharmaceutical compositions can be prepared by mixing the fusion protein with optional pharmaceutically acceptable carriers. Pharmaceutically acceptable carriers include solvents, dispersion media, isotonic agents and the like. Examples of carriers include water, saline solutions or other buffers (such as phosphate, citrate buffers), oil, alcohol, proteins (such as serum albumin, gelatin), carbohydrates (such as monosaccharides, disaccharides, and other carbohydrates including glucose, sucrose, trehalose, mannose, mannitol, sorbitol or dextrins), gel, lipids, liposomes, stabilizers, preservatives, antioxidants including ascorbic acid and methionine, chelating agents such as EDTA; salt forming counter-ions such as sodium; non-ionic surfactants such as TWEEN™, PLURONICS™ or polyethylene glycol (PEG), or combinations thereof.

The pharmaceutical compositions can contain more than one active compound. For example, the formulation can contain one or more fusion protein and/or one or more additional beneficial compound(s). The active ingredients can be combined with the carrier in any convenient and practical manner, e.g., by admixture, solution, suspension, emulsification, encapsulation, absorption and the like, and can be made in formulations such as powder (including lyophilized powder), suspensions that are suitable for injections, infusion, or the like. Sustained-release preparations can also be prepared.

In certain embodiments, the pharmaceutical compositions contains the fusion protein for human use. The pharmaceutical compositions can be prepared in an appropriate buffer including, but not limited to, citrate, phosphate, Tris, BIS-Tris, etc. at an appropriate pH and can also contain excipients such as sugars (50 mM to 500 mM of sucrose, trehalose, mannitol, or mixtures thereof), surfactants (e.g., 0.025%-0.5% of Tween 20 or Tween 80), and/or other reagents. The formulation can be prepared to contain various amounts of fusion protein. In general, formulations for administration to a subject contain between about 0.1 mg/mL to about 200 mg/mL. In certain embodiments, the formulations can contain between about 0.5 mg/mL to about 50 mg/mL; between about 1.0 mg/mL to about 50 mg/mL; between about 1 mg/mL to about 25 mg/mL; or between about 10 mg/mL to about 25 mg/mL of fusion protein. In specific embodiments, the formulations contain about 1.0 mg/mL, about 5.0 mg/mL, about 10.0 mg/mL, or about 25.0 mg/mL of fusion protein.

3. METHODS

Another aspect of the present invention relates to methods for making and using a fusion protein and compositions thereof.

a. Producing the Fusion Protein

In some embodiments, the method for making the fusion protein comprises (i) providing a bioactive molecule and an Fc fragment comprising a hinge region, (ii) modifying the hinge region to prevent it from forming a disulfide bond, and (iii) linking the bioactive molecule directly or indirectly to the scFc through the mutated hinge region to form the fusion protein, hybrid, conjugate, or composition thereof. The present disclosure also provides a method for purifying the fusion protein, comprising (i) providing a fusion protein, and (ii) purifying the fusion protein by Protein A or Protein G-based chromatography media.

The fusion protein may alternatively be expressed by well known molecular biology techniques. Any standard manual on molecular cloning technology provides detailed protocols to produce the fusion protein of the invention by expression of recombinant DNA and RNA. To construct a gene expressing a fusion protein of this invention, the amino acid sequence is reverse translated into a nucleic acid sequence, preferably using optimized codons for the organism in which the gene will be expressed. Next, a gene encoding the peptide or protein is made, typically by synthesizing overlapping oligonucleotides which encode the fusion protein and necessary regulatory elements. The synthetic gene is assembled and inserted into the desired expression vector. The synthetic nucleic acid sequences encompassed by this invention include those which encode the fusion protein of the invention, and nucleic acid constructs characterized by changes in the non-coding sequences that do not alter the biological activity of the molecule encoded thereby. The synthetic gene is inserted into a suitable cloning vector and recombinants are obtained and characterized. The fusion protein is expressed under conditions appropriate for the selected expression system and host. The fusion protein is purified by an affinity column of Protein A or Protein G (e.g., SoftMax®, AcroSep®, Sera-Mag®, or Sepharose®).

The fusion protein of the present invention can be produced in mammalian cells, lower eukaryotes, or prokaryotes. Examples of mammalian cells include monkey COS cells, CHO cells, human kidney 293 cells, human epidermal A431 cells, human Colo205 cells, 3T3 cells, CV-1 cells, other transformed primate cell lines, normal diploid cells, cell strains derived from in vitro culture of primary tissue, primary explants, HeLa cells, mouse L cells, BHK, HL-60, U937, HaK or Jurkat cells.

The invention also provides a method for producing a single chain Fc (sFc) region of an immunoglobulin G, comprising mutating, substituting, or deleting the Cys in a hinge region of Fc of IgG. In one embodiment, the Cys is substituted with Ser, Gly, The, Ala, Val, Leu, Ile, or Met. In another embodiment, the Cys is deleted. In an additional embodiment, a fragment of the hinge is deleted.

The invention further provides a method for producing a fusion protein comprising: (a) providing a bioactive molecule and an IgG Fc fragment comprising a hinge region, (b) mutating the hinge region by amino acid substitution and/or deletion to form a mutated Fc without disulfide bond formation, and (c) combining the bioactive molecule and the mutated Fc.

b. Using the Fusion Protein

The fusion protein of the invention can be administered intravenously, subcutaneously, intra-muscularly, or via any mucosal surface, e.g., orally, sublingually, buccally, sublingually, nasally, rectally, vaginally, or via pulmonary route.

The dose of the fusion protein of the invention will vary depending upon the subject and the particular mode of administration. The dosage required will vary according to a number of factors known to those skilled in the art, including, but not limited to, the fusion protein, the species of the subject and, the size of the subject. Dosage may range from 0.1 to 100,000 µg/kg body weight. The fusion protein can be administered in a single dose, in multiple doses throughout a 24-hour period, or by continuous infusion. The fusion protein can be administered continuously or at specific schedule. The effective doses may be extrapolated from dose-response curves obtained from animal models.

4. SPECIFIC EMBODIMENTS

Specific embodiments of the present invention include, but are not limited to, the following:

(1) A fusion protein comprising an Fc fragment of an IgG molecule and a bioactive molecule, wherein the Fc fragment is a single chain Fc (sFc).
(2) The fusion protein according to (1), wherein the Fc fragment comprises a hinge region.
(3) The fusion protein according to (2), wherein the hinge region is mutated and does not form disulfide bonds.
(4) The fusion protein according to (2), wherein the hinge region comprises an amino acid sequence selected from the group consisting of SEQ ID NOs: 1-60.
(5) The fusion protein according to (2), wherein the hinge region comprises an amino acid sequence of SEQ ID NO: 23 or 27.
(6) The fusion protein according to (1), wherein the bioactive molecule is a cytokine, a growth factor, a hormone, or a functional portion thereof
(7) The fusion protein according to (1), wherein the bioactive molecule is erythropoietin, Factor IX, IFNα, GCSF, and IFNβ.
(8) The fusion protein according to (1), wherein the bioactive molecule is linked to the Fc fragment through a mutated hinge region.
(9) The fusion protein according to (1), wherein the amino acid sequence of the fusion protein is selected from the group consisting of SEQ ID NOs: 66, 68, 70, 72, and 74.
(10) A pharmaceutical composition comprising the fusion protein according to any one of (1) to (9) and a pharmaceutically acceptable carrier or excipient.
(11) A method for producing a fusion protein comprising:
  a) providing a bioactive molecule and an Fc fragment comprising a hinge region,
  b) mutating the hinge region by amino acid substitution and/or deletion to form a mutated Fc, and
  c) combining the bioactive molecule and the mutated Fc.
(12) The method according to (11), wherein the hinge region is mutated by substitution and/or deletion of a cysteine residue.
(13) The method according to (11), wherein the bioactive molecule is combined with the mutated Fc through the hinge region.
(14) The method according to (11), wherein the bioactive molecule is a cytokine, a growth factor, a hormone, or a functional portion thereof
(15) The method according to (11), wherein the bioactive molecule is erythropoietin, Factor IX, IFNα, GCSF, and IFNβ.

Additional specific embodiments of the present invention include, but are not limited to the following examples.

EXAMPLE 1

Erythropoietin Single Chain Fc Fusion Protein (EPO-sFc)

1. Fusion Protein

In this example, a fusion protein was prepared having a structure of formula 1 discussed above:

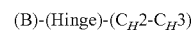

wherein:
the bioactive molecule (B) is erythropoietin (EPO) protein (SEQ ID NO: 65);

the hinge region (Hinge) is a mutated IgG1 hinge (SEQ ID NO: 27);

and ($C_H2$-$C_H3$) is a $C_H2$-$C_H3$ of IgG1 (SEQ ID NO: 62).

The full-length amino acid sequence of the EPO-sFc fusion protein is shown in the Sequence Listing as SEQ ID NO: 66.

2. Expression Vector

Figure 2:
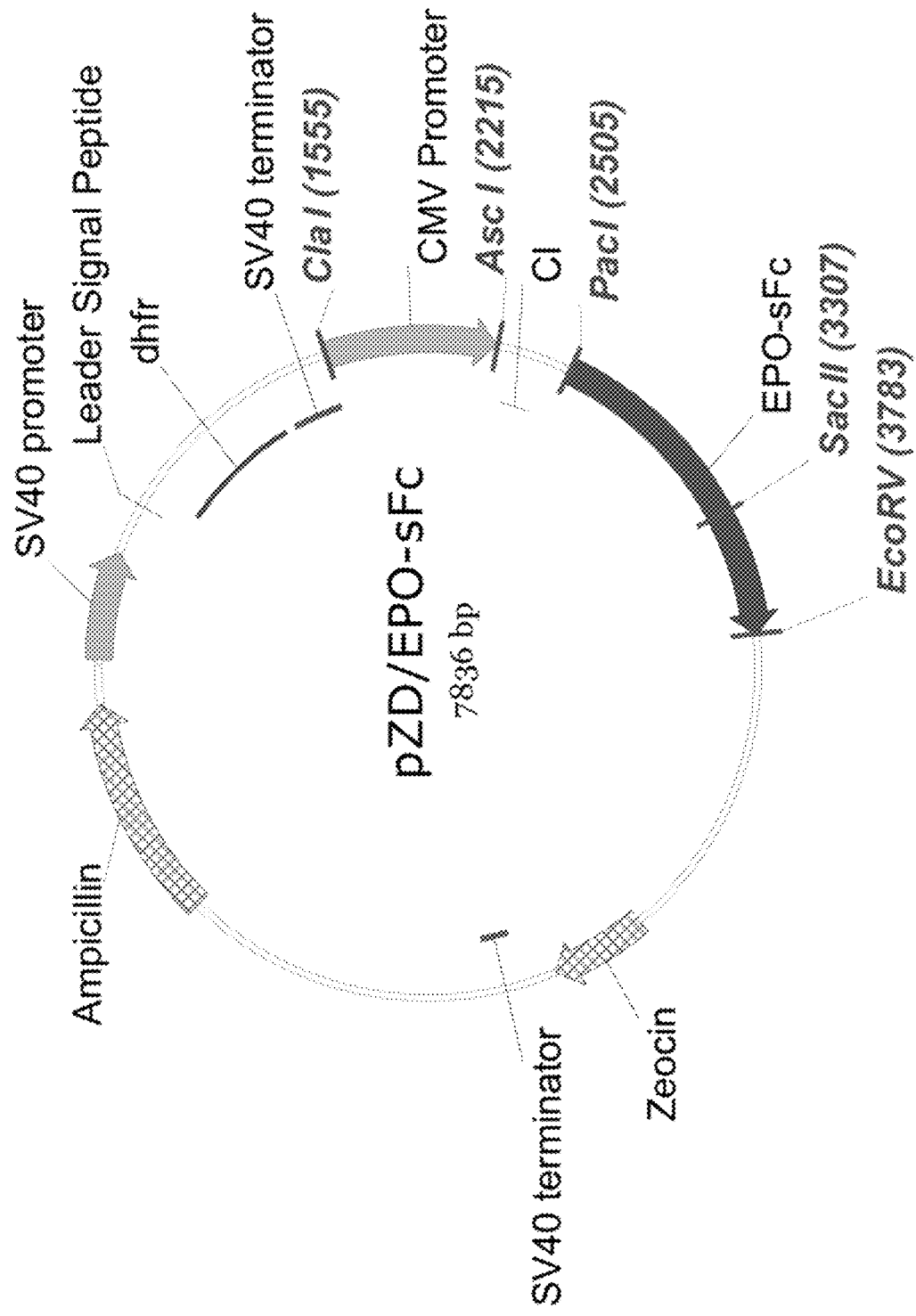
FIG. 2 illustrates a map of pZD/EPO-sFc plasmid. The pZD/EPO-sFc plasmid encodes an EPO-sFc fusion protein according to an embodiment of the present invention.

The EPO-sFc was produced using a DNA expression vector. The DNA fragment of the erythropoietin single chain Fc fusion protein (EPO-sFc) was assembled using overlapping primers by the method of assembly polymerase chain reaction (PCR). The assembled EPO-sFc fragment was then ligated into PacI and EcoRV sites of pZD vector (pcDNA3.1Neo, Invitrogen, Carlsbad, CA, cat. no. V790-20 with dhfr gene) to obtain pZD/EPO-sFc as shown in FIG. 2 and then transformed into *E. coli*. The expression vector construct contained the zeocin-resistance gene as a selection marker.

EXAMPLE 2

Establishment of Stable Recombinant Cell Lines Producing EPO-sFc

CHOdhfr- cells were trypsinized and resuspended at a concentration of 3×106 cells/mL in CP-T buffer (Cyto pluse Cat. CP-T). 0.2 mL of cell suspension (6×105 cells) was transfected with 10 μg of plasmid pZD/EPO-sFc by electroporation (PA4000 PulseAgile® electroporator, Cyto Pulse Sciences). After 48 hrs of growth in non-selective medium, the transfectants were incubated in the selective complete medium containing IMDM, 10% fetal bovine serum, Zeocin (Invitrogen Cat. 1486406) and 5 nM MTX (Sigma Cat. BCL5707V) to obtain high yield clone zE93. The expression of the secreted fusion protein in the culture medium was detected and quantified by Q-ELISA (Quantikine® IVD® Epo ELISA kit).

The original zE93 cells were cultivated in a 10-cm dish containing IMDM supplemented with 10% FBS, zeocin, and 0.1 μM MTX. Cells were maintained in a 37° C. humidified 95% air/5% $CO_2$ incubator (Model 3326, Forma scientific). In order to adapt the cells in serum-free culture medium, the medium was changed from IMDM to JRH serum-free medium supplemented with 5% FBS, zeocin, and 0.1 μM MTX. When cells became stable, the cells were detached from 10-cm dish by trypsinization and then transferred to spinner flasks containing 50 mL JRH serum-free medium supplemented with the same percentage of FBS. When confluency reach 90% in 3-5 days, the cells were subcultured into spinner flask containing JRH serum-free medium supplemented with a lower percentage of FBS. Cells were adapted into lower serum conditions by stepwise decreasing the FBS percentage from 10% to 0% in spinner flasks.

The concentration of EPO-sFc fusion protein in serum samples were quantified by QUANTIKINE® IVD® Epo ELISA kit (R&D Systems Inc., CN: DEP00). The serum dilution-fold was optimized and the plate layout for standards, controls, and specimens were determined before performing formal assays using the fusion protein. Absorbance at wavelength 450 nm and 600 nm was acquired by SOFTMAX® Pro 5 software.

High-yield clones were successfully obtained by selection, limiting dilution and stepwise MTX challenges to produce finally the fusion protein comprising the recombinant EPO linked to single chain Fc (i.e., EPO-sFc). The resulting fusion protein was purified for further in vitro or in vivo biological activity assays and pharmacokinetics studies.

EXAMPLE 3

Chromatographic Purification of EPO-sFc

Both Protein A based resin (MABSELECT SURE™) and DEAE resin (DEAE FF anion exchange column) were used to purify EPO-sFc. After purification, the corresponding recovery rate was analyzed by quantitative ELISA, and the respective purity by SDS-PAGE. Detailed purification processes for EPO-sFc are described below.

1. (MABSELECT SURE™) Purification

Culture medium from the high yield EPO-sFc producing cell line was applied to a Protein A based MABSELECT SURE™ column (GE; Cat. no. 11-0034-93) with a loading ratio at about 4.8 mg for 1 mL resin. After 2 washing steps, the fusion protein was eluted with pH 3.0 elution buffer and the eluate was thereafter neutralized to pH 8.8. The MABSELECT SURE™ eluate was analyzed by Q-ELISA (QUANTIKINE® IVD® EPO ELISA kit) to determine the quantity and recovery rate. The recovery rate was 65.8%, indicative of an efficient binding and purification of the designed EPO-sFc by MABSELECT SURE™ Protein A column (Table 3).

2. DEAE FF Purification

Before loading to DEAE FF 1 mL Hitrap column, the buffer was exchanged to DEAE FF equilibrium buffer. Thereafter, the EPO-sFc containing cell medium prepared from high yield cell line as described Example 2 was loaded to DEAE FF 1 mL Hitrap column with a loading ratio at about 5.92 mg for 1 mL resin. After acidic wash step, the main peak was eluted by 40 mM Tris buffer containing 130 mM NaCl, pH 8.0. DEAE FF eluate was then analyzed by Q-ELISA (QUANTIKINE® IVD® EPO ELISA kit). The overall recovery rate was 15.48% (Table 3).

3. Results

Table 3 reports information pertaining to the EPO-sFc fusion protein purified with MABSELECT SURE™ and DEAE FF, respectively. The table shows that MABSELECT SURE™ yields high purity EPO-sFc efficiently by a single purification step.

Figure 4:
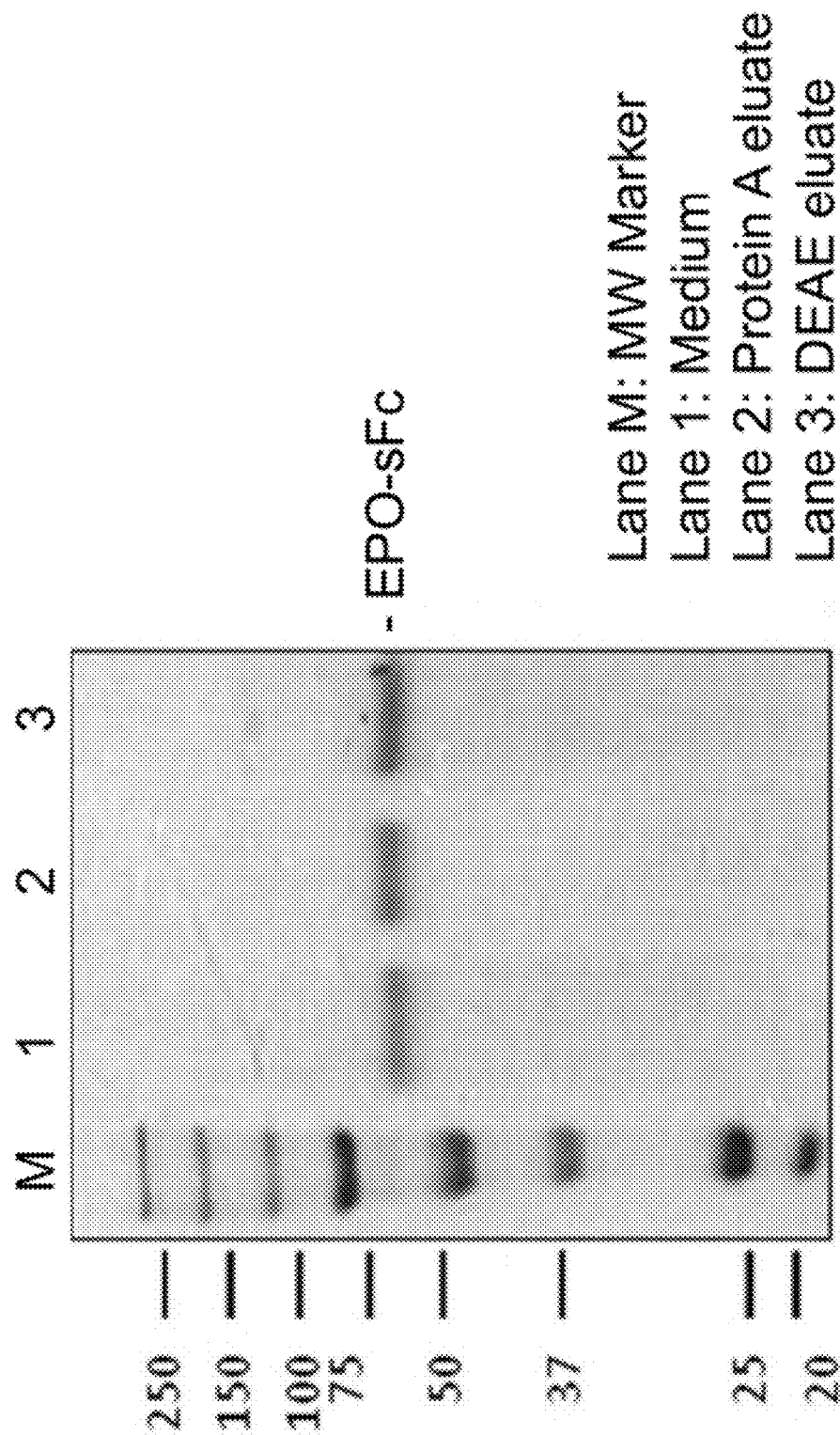
FIG. 4 illustrates an SDS-PAGE profile, by Coomassie blue staining, of erythropoietin single chain Fc fusion protein (EPO-sFc) produced by methods disclosed herein. Lane M is a molecular weight marker (marker contains recombinant proteins in size of 20, 25, 37, 50, 75, 100, 150, and 250 kDa). Lane 1 is an EPO-sFc fusion protein in cell culture medium. Lane 2 is an eluate of EPO-sFc fusion protein purified by Protein A resin (MabSelect SuRe™ Hitrap column). Lane 3 is an eluate of EPO-sFc fusion protein purified by DEAE column. The MW of EPO-sFc (Lanes 1 to 3) is between 50-70 KDa with high content of glycosylation.

FIG. 4 shows the EPO-sFc fusion protein produced using the methods discussed above revealed a major band by the SDS-PAGE (Lanes 1, 2, and 3). The MW of EPO-sFc was between 50-70 KDa with high content of glycosylation which was shown in a duplicated SDS-PAGE gel by Periodic Acid-Schiff (PAS) staining method.

Sialic acid was one of the important components for EPO-sFc to affect its half-life in body circulation. The MW of EPO-sFc was between 50-70 KDa with high content of glycosylation. According to Table 3, EPO-sFc was purified by different chromatographies including MABSELECT SURE™ and DEAE FF, respectively. MABSELECT SURE™ could yield high purity EPO-sFc efficiently by a single purification step. The DEAE FF anion exchange resin would provide further polish in purification to remove low sialic acid isoforms of EPO-sFc which might affect the half-life of EPO-sFc.

EXAMPLE 4

Pharmacokinetic Study for EPO-sFc

Ten rats (body weights ranging from 276-300 g rats) were purchased from BioLASCO Taiwan Co., Ltd. All rats were quarantined and acclimatized for four days prior to the initiation of the pharmacokinetic (PK) studies. The rats were divided into three testing groups, for the PK studies: (1) EPO-sFc purified by DEAE; (2) EPO-sFc purified by Protein A; and (3) original recombinant human EPO (EPREX®). The rats of groups (1) and (2) were dosed at 16.8 μg/kg and the rats of group (3) were dosed at 3.5 μg/kg. The proteins were dosed via subcutaneous (S.C.) administration. The rats were grouped and labeled with fur dye. Both reference protein (EPREX®, 3.5 μg/mL) and test fusion proteins EPO-sFc (DEAE resin) and EPO-sFc-(Protein A resin) (at 16.8 μg/mL) were prepared with fresh sample diluent (0.25% bovine serum albumin (AppliChem, CN: A0850,0250)) in saline for injection. All injections were administered to the rats via the site of dorsal neck for S.C. route.

Blood samples were collected at 0.5, 1, 2, 5, 8, 12, 24, 48, 72, 96, 120, and 144 hours after injection and then centrifuged at 3,000 rpm for 20 minutes. The supernatant was stored at −70° C.

The EPO concentrations in serum samples were quantified by QUANTIKINE® IVD® EPO ELISA kit (R&D Systems Inc., CN: DEP00). Before performing the assay, the serum dilution-fold was optimized and the plate was laid out for standards, controls, and specimens. The absorbances at wavelength 450 nm and 600 nm were acquired by SOFT-MAX® Pro 5 software. The Cmax, Tmax, AUC values, and the elimination phase half-life ($T_{1/2}$) from the EPO concentrations in serum were calculated by PK Solutions 2.0™ software.

Figure 6:
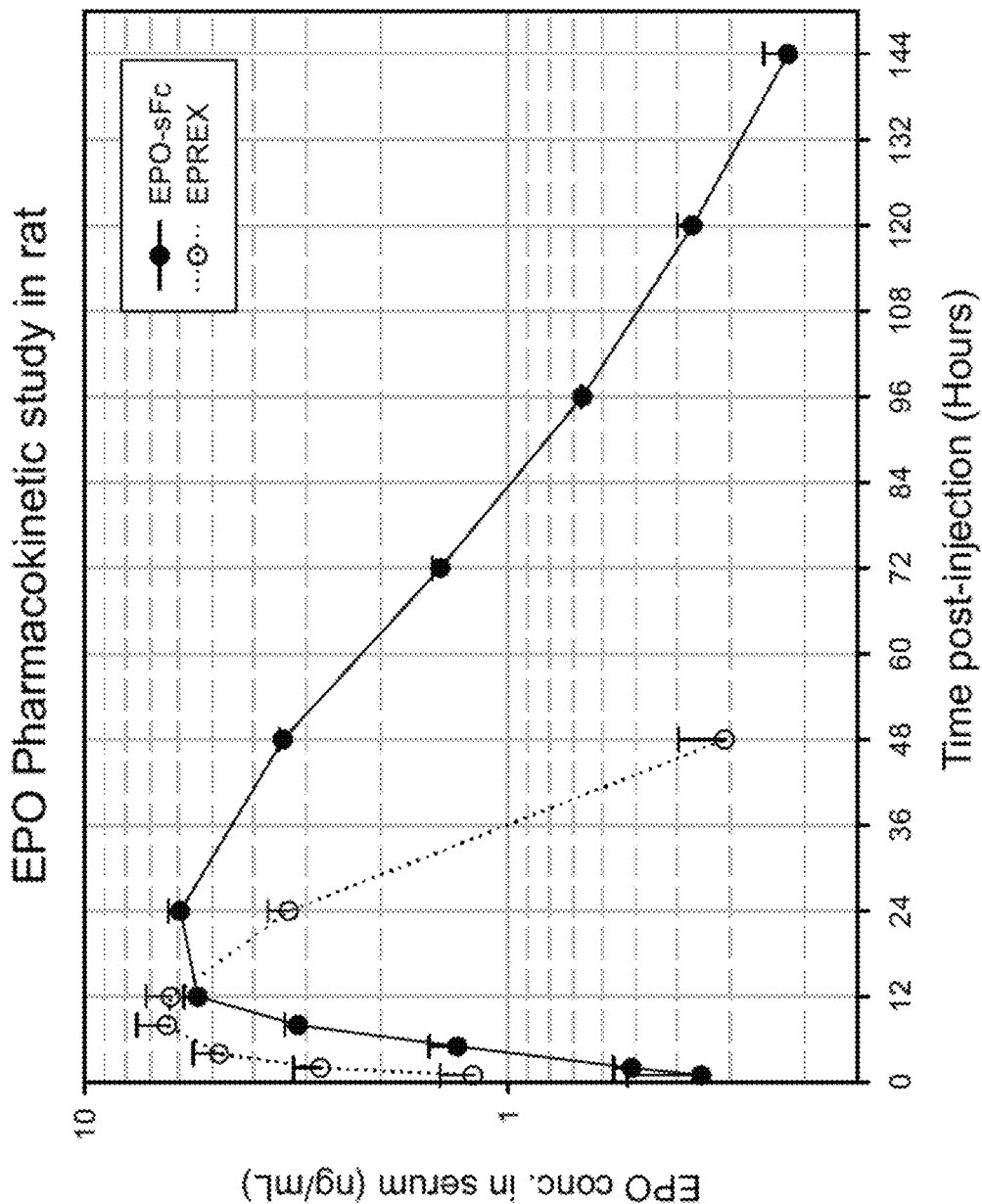
FIG. 6 is a graph showing the pharmacokinetics (PK) profile of a single dose subcutaneous (S.C.) administration of erythropoietin single chain Fc fusion protein (EPO-sFc) (closed circle) and original recombinant human EPO (EPREX®) (open circle) in rats. For single dose S.C. administration of EPO-sFc at 16.8 μg/kg, the half-life of EPO-sFc is about 22 hours, which is 3 times longer than EPREX®.

The subcutaneous (S.C.) pharmacokinetic profiles of EPO-sFc purified from DEAE FF and EPREX® in rats after administration with single dose are shown in FIG. 6 and the mean pharmacokinetic features are shown in Table 5. The half-life of EPO-sFc-DEAE was 22.3±0.38 (hrs). In contrast, the half-life of EPREX® was only 6.182±0.675 (hrs). The AUCs of EPO-sFc (DEAE) and EPREX® were 327.4±15.13 and 161.5±23.64 (ng-hr/mL), respectively. The Tmax of EPO-sFc (DEAE) and EPREX® was 18±0.00 and 9.33±2.31 (hr), respectively.

The half-life of EPO-sFc was shown to be prolonged for up to 3 fold when compared to the original EPO (EPREX®) product. The EPO-sFc of this instant invention would therefore allow for use in chronic kidney disease (CKD) or cancer patients to decrease the injection frequency and improve patient life quality.

EXAMPLE 5

Biological Activity Assay for EPO-sFc

Eight female BALB/c mice (8 weeks old) were divided into two groups for determining the biological activity of EPO. One group was dosed with the reference drug (EPREX®) and other group was dosed with the EPO-sFc fusion protein of the present disclosure (EPO-sFc). Reference drug (EPREX®, Johnson and Johnson) was purchased and freshly prepared at the concentrations of 336 μg/mL (equal to 40 IU/mL). The EPO-sFc fusion protein produced according to Example 3 was freshly prepared at the concentrations of 0.336 ng/mL (equivalent molar to 40 IU/mL of EPREX®). Each mouse was subcutaneously administered with 0.5 ml of EPREX® or EPO-sFc fusion protein on day 1, and then blood collection was performed on days 4 to 9, 11, and 13.

The number of reticulocytes is a good indicator of biological activity of erythropoietin as it represents recent production and allows for the determination of reticulocyte count and erythropoietin potency. The number of reticulocytes was determined by FACS. 1.0 mL of PBS and 5.0 μL of whole blood were added to a polystyrene tube for unstained sample. 1.0 mL of Thiazole Orange (BD RETIC-COUNT™, cn:349204) and 5.0 μL of whole blood were added to a polystyrene tube for stained sample. Both tubes were incubated in the dark at room temperature for 30 min, and then analyzed within 3.5 hours after incubation. The samples were gently mixed immediately prior to analysis. The reticulocytes was determined by flow-cytometry (BD FACSCalibur™) and analyzed by CellQuest Pro™ software. The percentage of reticulocytes of each sample was calculated to evaluate the efficacy area under the curve (AUC) and maximal percentage of reticulocyte ($RET_{max}$) by PK solutions 2.0 software (Summit, Montrose, CO, USA).

The reticulocyte counts were used to compare the activity of reference drug and EPO-sFc fusion protein by measuring AUEC and $RET_{max}$ (Table 7). The AUEC of 0 to 13 hours was 88.69 and 91.03 ng·hr/ml for EPREX® and EPO-sFc fusion protein, respectively. In addition, the RETmax of EPREX® and EPO-sFc fusion protein was 11.12% and 10.48%, respectively. The results of AUEC and $RET_{max}$ suggests that the single chain Fc portion of the EPO-sFc fusion protein does not significantly interfere with the function of the EPO portion since the biological activity of EPO-sFc was comparable to EPREX® in this Example.

EXAMPLE 6

Factor IX Single Chain Fc Fusion Protein (FIX-sFc)

1. Fusion Protein

In this example, a fusion protein was prepared having a structure of formula 1 discussed above:

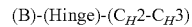

wherein:
the bioactive molecule (B) is Factor IX protein (FIX) (SEQ ID NO: 67);
the hinge region (Hinge) is a mutated IgG1 hinge (SEQ ID NO: 23); and
($C_H2$-$C_H3$) is a $C_H2$-$C_H3$ of IgG1 (SEQ ID NO: 61).

The full-length amino acid sequence of the FIX-sFc fusion protein is shown in the Sequence Listing as SEQ ID NO: 68.

2. Expression Vector

Figure 3:
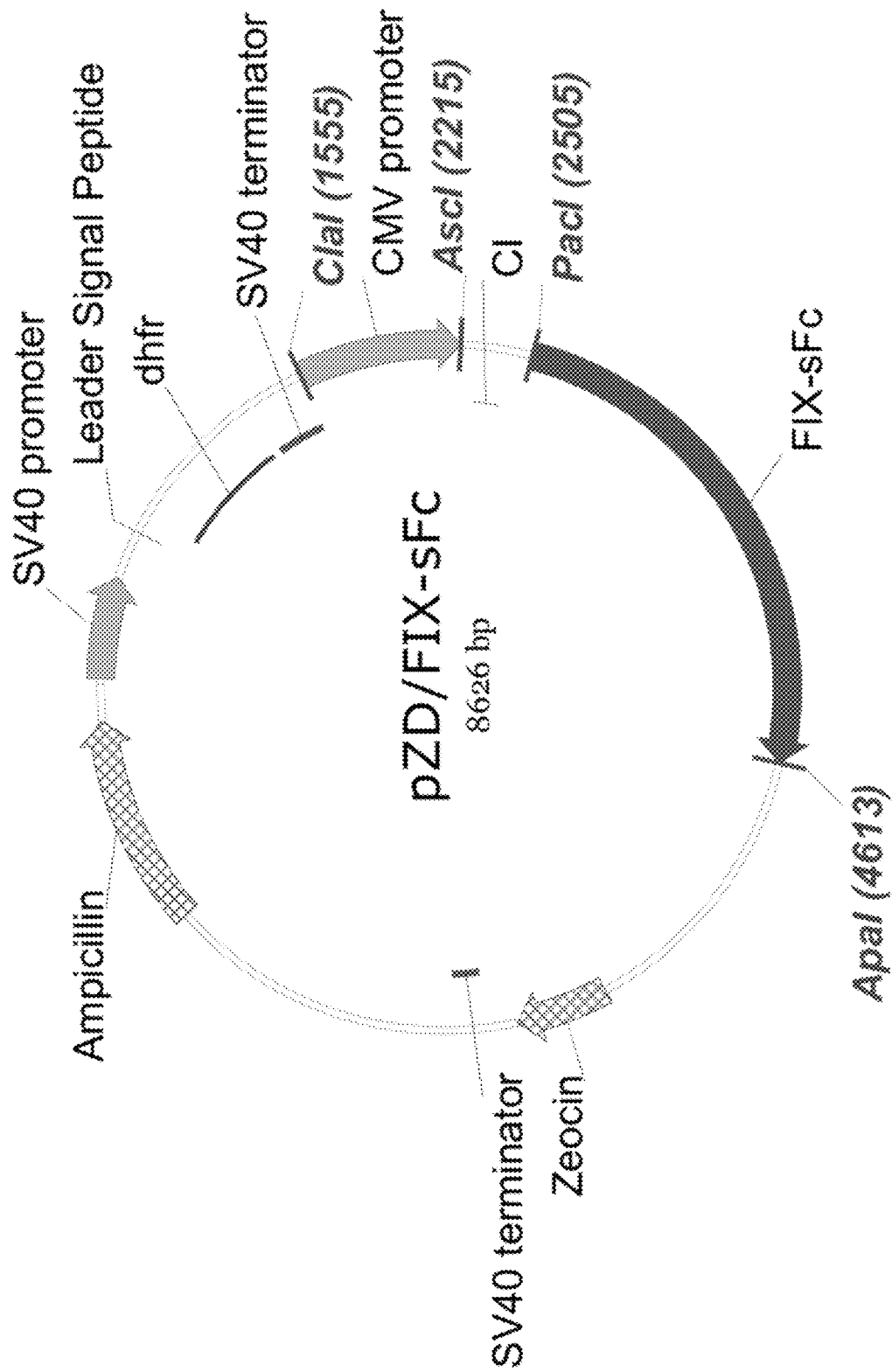
FIG. 3 illustrates a map of pZD/FIX-sFC plasmid. The pZD/FIX-sFc plasmid encodes a Factor IX-sFc fusion protein according to an embodiment of the present invention.

The FIX-sFc was produced using a DNA expression vector. The DNA fragment of the Factor IX was assembled using overlapping primers by the method of assembly PCR. The full-length gene of Factor IX single chain Fc fusion protein (FIX-sFc) was amplified from the reaction mixture, ligated into PacI and ApaI sites of pZD vector (pcDNA3.1Neo, Invitrogen, Carlsbad, CA, cat. no. V790-20 with dhfr gene) to obtain pZD/FIX-sFc as shown in FIG. 3 and then transformed into E. coli. The expression vector construct contained the zeocin-resistance gene as a selection marker.

EXAMPLE 7

Establishment of Stable Recombinant Cell Lines Producing FIX-sFc $CHO_{dhfr}$-cells were trypsinized and resuspended at a concentration of $3\times10^6$ cells/mL in CP-T buffer (Cyto pluse Cat. CP-T). Then 0.2 mL of the cell suspension (6×10⁵ cells) was transfected with 15 μg of plasmid pZD/FIX-sFc by electroporation for the expression of rhFIX-sFc (PA4000 PulseAgile® electroporator, Cyto Pulse Sciences). After 48 hrs of growth in non-selective medium, the transfectants were cultured under selective complete medium containing IMDM, 10% fetal bovine serum, Geneticin (Invitrogen Cat. 10131-027) and 5 nM MTX (Sigma Cat. M-8407) to obtain high yield clone N18. After cells achieving confluent in 96-well plates, the level of rhFIX-sFc was assessed by Q-ELISA and clones with high expression were transferred to 6-well plate. These clones were subcultured at 1×10⁵ cells per well and allowed to grow for 7 days before determining FIX-sFc containing media titer by Q-ELISA.

The capture antibody (mouse Factor IX monoclonal antibody, Bioporto, Denmark, Cat. HYB 133-09) in 1:1000 (1 μg/mL) was prepared in carbonate/bicarbonate coating buffer for use. 100 μl of the diluted capture antibody was added into wells of ELISA plate and incubated at 4° C. overnight. A detection antibody (Rabbit factor IX polyclonal Ab, Abcam, (U.K.), Cat. Ab23335) was diluted in PBST (PBS with 0.05% Tween 20) at 1:1,000 and added to ELISA plates. HRP conjugate antibody (Peroxidase-AffiniPure Goat Anti-Rabbit Ab, Jackson ImmunoResearch, (USA), Cat.111-035-144) and TMB Peroxidase Substrate (KPL, Cat.53-00-03) were used to produce color. Finally, 100 μl N $H_2SO_4$ was added to stop the reaction. The absorbances at wavelength 450 nm and 600 nm were acquired by Soft-Max® Pro 5 software. The concentration of FIX-sFc were determined by an equation $(X=[a/(Y-Y_0)-1](1/b) \times X_0)$, and the C initial value, AUC value and elimination phase half-life $(T_{1/2})$ were calculated for the concentration of FIX-sFc using PK solution 2.0™ software.

The original N18 clone was cultivated in a 10-cm dish containing IMDM supplemented with 5% FBS, zeocin, and 0.01 μM MTX. Cells were maintained in a 37° C. humidified 95% air/8% $CO_2$ incubator (Model 3326, Forma scientific). In order for cells to adapt in serum-free medium, the culture medium was changed from IMDM to EX-CELL® 325 PF CHO Serum-Free Medium supplemented with 2% FBS, zeocin, and 0.02 μM MTX. When cells became stable, the cells were detached from 10-cm dish by trypsinization and then transferred to spinner flasks containing 50 mL EX-CELL® 325 PF CHO Serum-Free Medium supplemented with the same percentage of FBS. When cell confluence reached 90% in 3-5 days, the cells were subcultured into spinner flask containing EX-CELL® 325 PF CHO Serum-Free Medium supplemented with a lower percentage of FBS. Cells were adapted into lower serum conditions by stepwise decreasing the FBS percentage from 2% to 0% in spinner. To further increase rhFIX-sFc productivity and activity, the clone was re-transfected with pZD/FIX-sFc. Cells from the high yield clone, N18-reZB, were subsequently sorted by FACS to separate therein the high yield cell group and grow under EX-CELL® 325 PF CHO Serum-Free Medium. Cells from the clone N18-reZB were tested by different MTX condition to select cells producing high yield of rhFIX-sFc.

After a round of selection, one high-yield clone, N18-reZB-sp4-sp5, was further selected by Q-ELISA MTX challenge. Subsequently, the serum-free clone was retransfected with pZD/FIX-sFc by sorting and MTX challenging and subjected to function selection leading to high-yield clones. N18-reZB-sp4-sp5 was obtained in this process. The accumulated titer in batch culture of N18-reZB-sp4-sp5 was about 53.4 μg/mL as determined by the Q-ELISA.

EXAMPLE 8

Chromatographic Purification of FIX-sFc

Both Protein A resin (MabSelect SuRe™) and IX Select resin were used to purify FIX-sFc. After purification, the corresponding recovery rate was analyzed by quantitative ELISA and the respective purity by SDS-PAGE. Detailed purification processes for FIX-sFc are described below.

1. MabSelect SuRe™ Purification

FIX-sFc producing cell line culture medium was applied to a Protein A based MabSelect SuRe™ column with a loading ratio about 1.84 mg for 1 mL resin. After 2 washing steps, the fusion protein was eluted from the column by pH 3.0 buffer. MabSelect SuRe™ eluate was analyzed by Q-ELISA to determine the quantity and recovery rate. The FIX-sFc was captured by MabSelect SuRe™ efficiently and a single step purification already yielded a highly purified preparation as shown in Lane 2 of FIG. 5.

2. IX Select Purification

The IXSelect affinity (GE; no. 17-5505-01) resin was packed in 1 mL column. The resin was coupled with monoclonal antibody directed against FIX. The range of loading pH was from 6.5-8.0. The FIX-sFc medium was loaded to IXSelect column without buffer exchange. The loading ratio was about 1.69 mg for 1 mL resin. After washing step to remove unbound materials, the main peak was eluted by 20 mM Tris containing 2 M $MgCl_2$, pH 7.4 buffer. Thereafter, IXSelect eluate was analyzed by Q-ELISA.

3. Results

Table 4 reports information pertaining to the FIX-sFc fusion protein purified with MabSelect SuRe™ and IX Select affinity resin, respectively. The table shows that MabSelect SuRe™ and IX Select yield high purity FIX-sFc efficiently by a single purification step.

Figure 5:
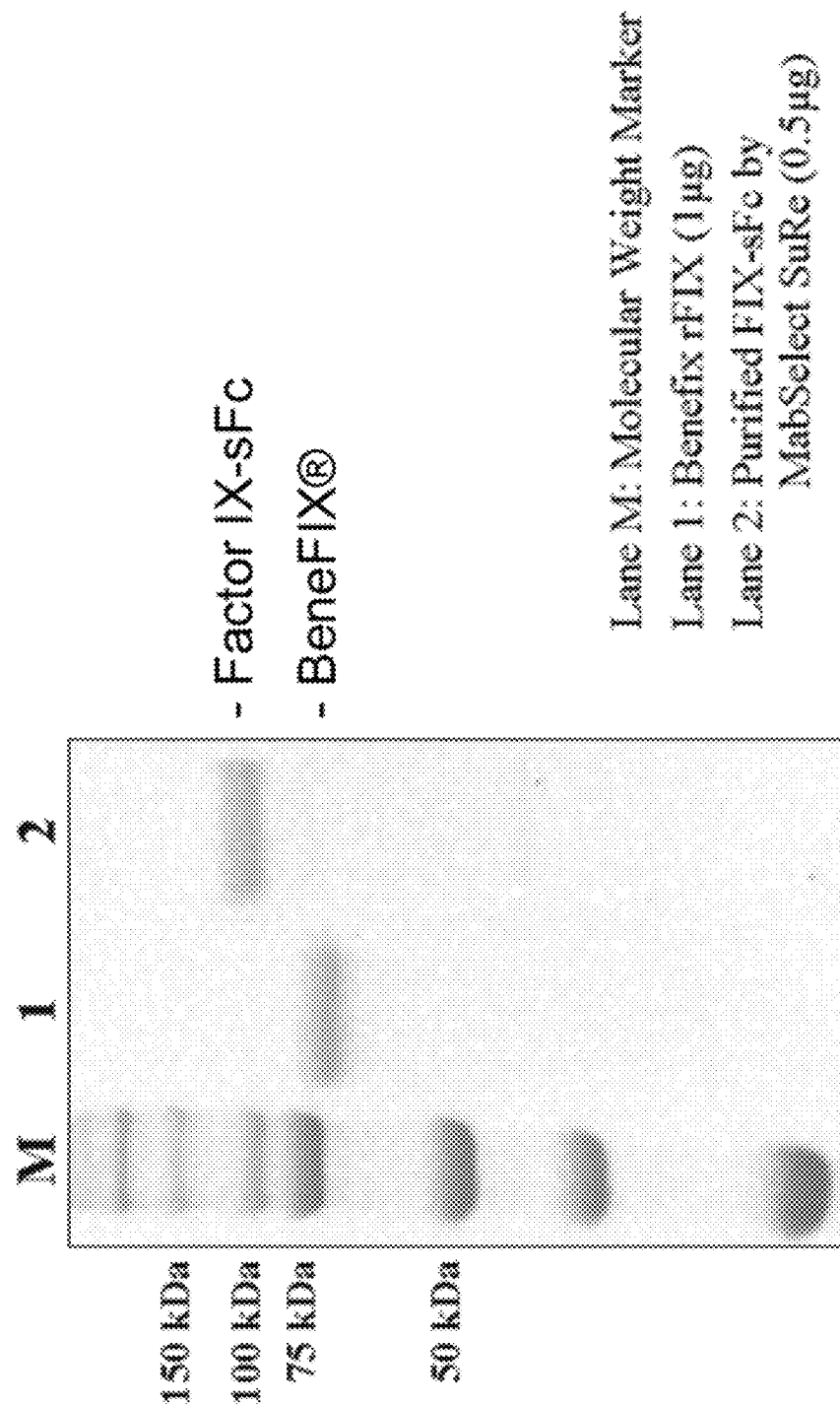
FIG. 5 illustrates an SDS-PAGE profile, by Coomassie blue staining, of Factor IX single chain Fc fusion protein (Factor IX-sFc) produced by methods disclosed herein. Lane M is a molecular weight marker (marker contains recombinant protein in size of 50, 75, 100, and 150 kDa). Lane 1 is an original recombinant human Factor IX (BeneFIX®). Lane 2 is an eluate of Factor IX-sFc fusion protein purified by Protein A resin (MabSelect SuRe™ Hitrap column). The MW of Factor IX-sFc (Lane 2) is between 100-110 KDa with high content of glycosylation.

FIG. 5 shows the FIX-sFc fusion protein produced using the methods discussed above revealed a major band by the SDS-PAGE (Lanes 1 and 2). The MW of Factor IX-sFc was between 100-110 KDa with high content of glycosylation which was shown in a duplicated SDS-PAGE gel by Periodic Acid-Schiff (PAS) staining method. The recovery rate of MabSelect SuRe™ and IXSelect was 88.34% and 20.05%, respectively (Table 4). The Protein A based MabSelect SuRe™ column chromatography purified FIX-sFc efficiently by a single step with high yield and purity as shown in FIG. 5 due to the unexpected Protein A/G binding property of the sFc from the designed fusion protein FIX-sFc.

EXAMPLE 9

Pharmacokinetic Study for FIX-sFc

Eight SD rats, weighing 315-375 g, were purchased from BioLASCO Taiwan Co., Ltd. The rats were randomly divided into two groups for pharmacokinetic (PK) studies: (1) recombinant FIX (BeneFIX®) as a reference drug; and (2) FIX-sFc of the present disclosure. The rats of group (1) and (2) were dosed at 1 mg/kg via tail vein on Day 0. After injection, the rats were bled at 0, 0.25, 4, 8, 24, 48, 72, 96 and 168 hours after injection according to the testing schedule. The coagulant free blood samples were placed at room temperature for at least 30 minutes with the serum isolated by centrifugation at 3,000 rpm for 20 minutes. The serum samples were aliquoted and stored at −70° C. until analysis.

The diluted capture antibody (mouse Factor IX monoclonal antibody, Bioporto, Denmark, Cat. HYB 133-09) in 1:1000 (1 µg/mL) was prepared using carbonate/bicarbonate coating buffer. A buffer capsule (Sigma, Cat. # C-3041) was dissolved in 100 mL ddH$_2$O to yield 0.05 M buffer, pH 9.6, filtrated by 0.2 µm filter, and stored at 4° C. 100 µl of the diluted captured antibody was added into wells of ELISA plate and incubated at 4° C. overnight. The plates were blocked using 200 µl of blocking buffer (PBS, pH 7.2 containing 2.0% BSA), and washed 3 times with 200 µl of PBS (PBS, pH 7.2). 100 µl of BeneFIX® (100 ng/mL, 50 ng/mL, 25 ng/mL, 12.5 ng/mL, 6.25 ng/mL, 3.125 ng/mL, and 1.5625 ng/mL) and FIX-sFc at corresponding concentrations were added to each ELISA well, respectively, and incubated at 37° C. for 1 hour. The ELISA plates were then washed 3 times with 200 µl of PBST (PBS with 0.05% Tween 20). A detection antibody (Rabbit factor IX polyclonal Ab, Abcam, (U.K.), Cat. Ab23335) was diluted in PBST (PBS with 0.05% Tween 20) by 1:1,000 and added into ELISA plates. After incubation, the ELISA plates were washed 3 times with PBST. HRP conjugate antibody (Peroxidase-AffiniPure Goat Anti-Rabbit Ab, Jackson ImmunoResearch, (USA), Cat.111-035-144) and TMB Peroxidase Substrate (KPL, Cat.53-00-03) were added into the plates to produce color. Finally, 100 µl 1 N H$_2$SO$_4$ was used to stop the reaction. The absorbances of diluted serum at wavelength 450 nm and 600 nm were acquired by SoftMax® Pro 5 software. The concentration of FIX-sFc was determined using an equation $(X=[a/(Y-Y_0)-1](1/b) \times X_0)$. The C initial value, AUC value and elimination phase half-life $(T_{1/2})$ were calculated by the concentration of FIX-sFc using PK solution 2.0™ software.

Figure 7:
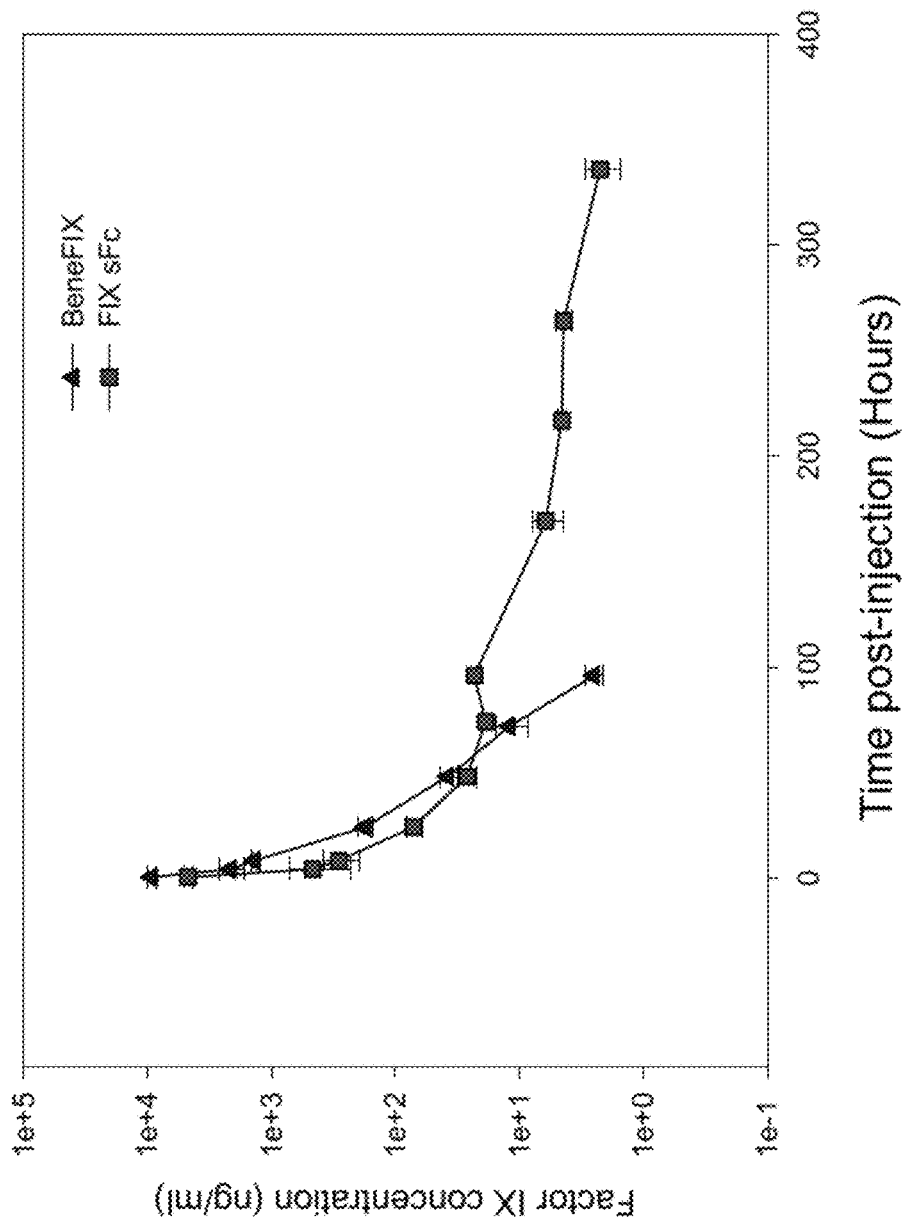
FIG. 7 is a graph showing the pharmacokinetics (PK) profile of a single dose intravenous (I.V.) administration of Factor IX single chain Fc fusion protein (FIX-sFc) (square) and original recombinant human Factor IX (BeneFIX®) (triangle) in rats. The half-life of FIX-sFc is about 56 hours for I.V. administration, which is 5 times longer than BeneFIX® ($T_{1/2}$=11.91 hours).

The intravenous (I.V.) pharmacokinetic profiles of FIX-sFc purified from MabSelect SuRe™ and BeneFIX® in rats after administration with a single dose are shown in FIG. 7 and the mean pharmacokinetic features are shown in Table 6. The half-life of FIX-sFc and BeneFIX® were 56.0±13.1 and 11.91±2.54 (hrs), respectively. The AUCs of FIX-sFc and BeneFIX® were 19080.3±2606.4 and 46594.40±3634.08 (ng-hr/mL), respectively. The C initial of FIX-sFc and BeneFIX® were 4668.0±447.5 and 11790.98±4898.85 (ng/mL), respectively.

The half-life of FIX-sFc of the present invention was about 56 hours in rats with I.V. administration, which is 5× longer than that (11.91±2.54 hrs) of BeneFIX®. The FIX-sFc is, therefore, a long-acting drug for hemophilia patients to decrease the injection frequency and improve patient's quality of life. The pharmacokinetic data indicated that the FIX-sFc of the invention might be bound to the Fc receptor, resulting in a lower C initial concentration and AUC and released slowly back into the blood stream, resulting in its longer half-life.

EXAMPLE 10

Biological Activity Assay of FIX-sFc

Activated Partial Thromboplastin Time (APTT) test was used to determine the biological activity of FIX-sFc. Briefly, the reference drug (BeneFIX®, Wyeth) and FIX-sFc were freshly prepared and diluted in Factor IX deficient plasma (Haematologic Technologies, Inc) at concentrations of 10, 5, and 2.5 µg/ml (final volume=500 µL). The samples (BeneFIX® or FIX-sFc) were then mixed with equal volume of Dade® Actin® FSL Reagent (Siemens Healthcare Diagnostics Products GmbH) and incubated at 37° C. for 3 min. Finally, CaCl$_2$ was added to stop the clotting reaction and observe the clot formation. The clotting time and specific activity were recorded and calculated by parallel line method (PLA analysis).

As shown in Table 8, the clotting time was dependent on the concentration of BeneFIX® or FIX-sFc. The average APTT result was 30.1, 26.2, and 25.5 sec for the FIX-sFc at the concentration of 2.5, 5.0, and 10.0 µg/ml, respectively. As shown in Table 8, the FIX-sFc had a similar relative potency and specific activity compared to BeneFIX®. FIX-sFc maintained an equivalent biological activity to BeneFIX®, which suggests that the single chain Fc does not interfere with the function of FIX in the fusion protein.

EXAMPLE 11

Interferon Alpha Single Chain Fc Fusion Protein (IFNα-sFc)

1. Fusion Protein

In this example, a fusion protein comprising interferon alpha (IFNα) was prepared and subsequently used in later examples. IFNα is a representative example of the large family of IFNα molecules.

Specifically, an IFNα single chain fusion protein (IFNα-sFc) was prepared having a structure of formula 1 discussed above:

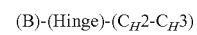

wherein:
the bioactive molecule (B) is interferon alpha (IFNα) protein (SEQ ID NO: 69);
the hinge region (Hinge) is a mutated IgG1 hinge (SEQ ID NO: 23); and
$(C_H2-C_H3)$ is a $C_H2-C_H3$ of IgG1 (SEQ ID NO: 62).

The full-length amino acid sequence of the IFNα-sFc fusion protein is shown in the Sequence Listing as SEQ ID NO: 70.

2. Expression Vector

Figure 8:
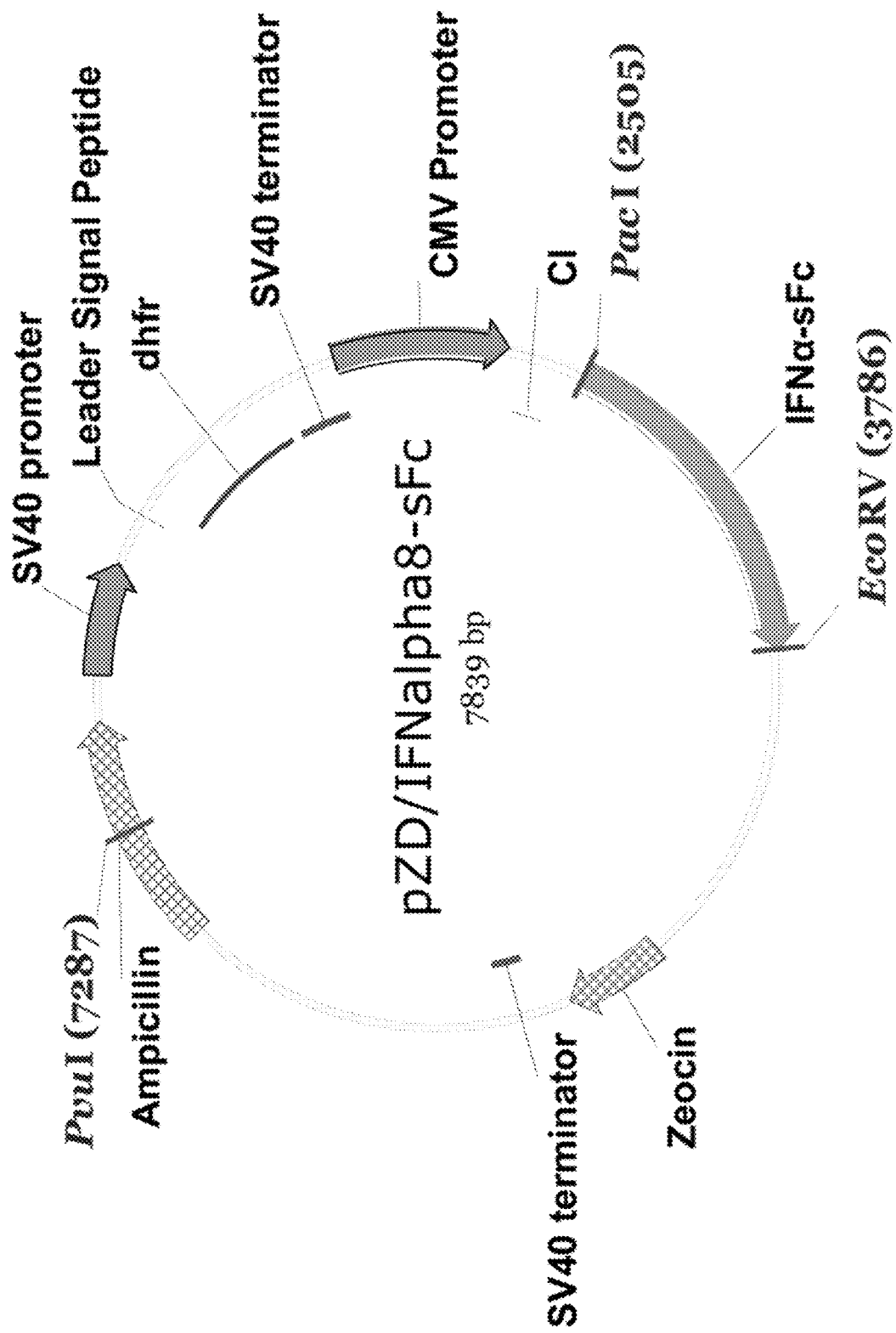
FIG. 8 illustrates a plasmid map of pZD/IFNα-sFc. The pZD/IFNα-sFc plasmid encodes an IFNα-sFc fusion protein according to an embodiment of the present invention.

The IFNα-sFc was produced using a DNA expression vector. The DNA fragment of IFNα-sFc was assembled using overlapping primers by the method of assembly polymerase chain reaction (PCR). The assembled IFNα-sFc fragment was then ligated into PacI and EcoRV sites of pZD vector (pcDNA3.1Neo, Invitrogen, Carlsbad, Calif., cat. no. V790-20 with dhfr gene) to obtain pZD/IFNα-sFc as shown in FIG. 8 and then transformed into E. coli. The expression vector construct contained the zeocin-resistance gene as a selected marker.

EXAMPLE 12

Establishment of Stable Recombinant Cell Lines Producing IFNα-sFc

CHO$_{dhfr-}$ cells were trypsinized and resuspended at a concentration of 3×10$^6$ cells/mL in CP-T buffer (Cyto pluse Cat. CP-T). 0.2 mL of cell suspension (6×10$^5$ cells) was transfected with 10 µg of plasmid pZD/IFNα-sFc by electroporation (PA4000 PulseAgile® electroporator, Cyto Pulse Sciences). After 48 hrs of growth in non-selective medium, the transfectants were incubated in the selective complete medium containing IMDM, 10% fetal bovine serum, Zeocin (Invitrogen Cat. 1486406) and 5 nM MTX (Sigma Cat. BCL5707V) to obtain high yield clone 22-123-

327-117-Re117. The expression of the secreted fusion protein in the culture medium was detected and quantified by Q-ELISA.

The original 22-123-327-117-Re117 cells were cultivated in a 10-cm dish containing IMDM supplemented with 10% FBS, zeocin, and 0.1 μM MTX. Cells were maintained in a 37° C. humidified 95% air/5% $CO_2$ incubator (Model 3326, Forma scientific). In order to adapt the cells in serum-free culture medium, the medium was changed from IMDM to JRH serum-free medium supplemented with 5% FBS, zeocin, and 0.1 μM MTX. When cells became stable, the cells were detached from 10-cm dish by trypsinization and then transferred to spinner flasks containing 50 mL JRH serum-free medium supplemented with the same percentage of FBS. When confluency reached 90% in 3-5 days, the cells were subcultured into spinner flask containing JRH serum-free medium supplemented with a lower percentage of FBS. Cells were adapted into lower serum conditions by stepwise decreasing the FBS percentage from 10% to 0% in spinner flasks.

The concentration of IFNα-sFc fusion protein in serum samples was quantified by an in-house IFNα-sFc ELISA kit. Absorbance at wavelength 450 nm and 600 nm was acquired by SoftMax® Pro 5 software. High-yield clones were successfully obtained by selection, limiting dilution and stepwise MTX challenges to produce finally the fusion protein comprising the recombinant IFN alpha8 linked to single chain Fc (i.e., IFNα-sFc). The resulting fusion protein was purified for further in vitro or in vivo biological activity assays and pharmacokinetics studies.

EXAMPLE 13

Chromatographic Purification of IFNα-sFc

Figure 9:
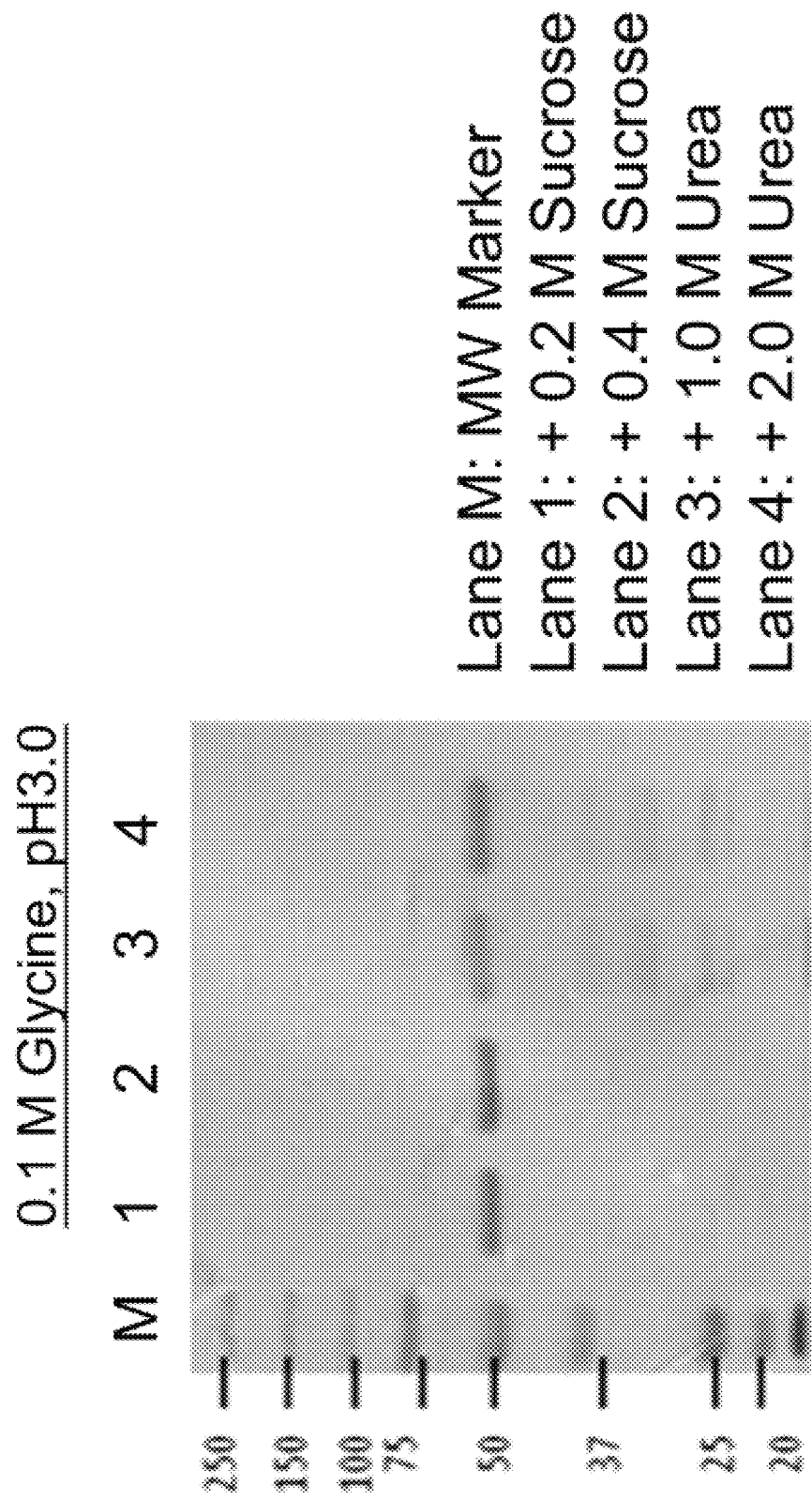
FIG. 9 illustrates an SDS-PAGE profile, by Coomassie blue staining, of Interferon alpha single chain Fc fusion protein (IFNα-sFc) produced by methods disclosed herein. Lane M is a molecular weight marker (marker contains recombinant proteins in size of 20, 25, 37, 50, 75, 100, 150, and 250 kDa). Lanes 1 and 2 are eluates of IFNα-sFc fusion protein containing 0.2 to 0.4 M sucrose, respectively. Lanes 3 and 4 are eluates of IFNα-sFc fusion protein containing 1.0 to 2.0 M urea, respectively.

Protein A based resin (MabSelect SuRe™) was used to purify IFNα-sFc. After purification, the corresponding recovery rate was analyzed by quantitative ELISA, and the respective purity by SDS-PAGE. The detailed purification processes for IFNα-sFc fusion protein is described below.
1. MabSelect SuRe™ Purification Culture medium from the high yield IFNα-sFc producing cell line was applied to a Protein A based MabSelect SuRe™ column (GE; Cat. no. 11-0034-93) with a loading ratio at about 4.6 mg for 1 mL resin. After 2 washing steps, the fusion protein was eluted with 0.1M Glycine pH3.0 elution buffer. The main peak is eluted by elution buffer. The MabSelect SuRe™ eluate was analyzed by Q-ELISA to determine the quantity and recovery rate.
2. Results IFNα-sFc was purified by MabSelect SuRe™ using different buffer conditions. The results showed that the 0.1 M Glycine pH3.0 elution buffer could purify IFNα-sFc efficiently with high purity for further determination of the physical-chemical properties. The eluates of purified IFNα-sFc samples were analyzed by SDS-PAGE as shown in FIG. 9 which revealed the purified IFNα-sFc as a major band in all buffers evaluated. The stabilizing additives (sucrose or urea) were used in the elution buffer to prevent precipitation. Some low molecular weight impurities appeared when urea was used as an additive in the buffer. The purity of IFNα-sFc in the glycine elution buffer having a sucrose additive was found to be >95%.

EXAMPLE 14

Pharmacokinetic Study for IFNα-sFc

Eight rats, weighing from 276-300 g, were purchased from BioLASCO Taiwan Co., Ltd. All rats were quarantined and acclimatized for four days prior to the initiation of the pharmacokinetic (PK) studies. The rats were divided into four testing groups for the PK studies: (1) Pegasys® (pegylated IFNα), (2) IFNα-sFc of this disclosure, (3) Peg-Intron® (pegylated IFNα), and (4) Roferon-A® (recombinant IFNα). The rats were dosed at 310 pmol/kg, which was converted equivalently into 18.6 μg/kg for Pegasys®, 13.95 μg/kg for IFNα-sFc, 9.7 μg/kg for Peg-Intron® and 5.89 μg/kg for Roferon-A®. All articles were freshly prepared with fresh sample diluents, 0.2% bovine serum albumin (AppliChem, CN: A0850,0250) in phosphate-buffered saline. The rats were grouped and labeled with fur dye. All injections were administered to the rats via the site of dorsal neck for subcutaneous (S.C.) route.

Blood samples were collected at 0.5, 1, 2, 4, 6, 12, 24, 36, 48, 60, 72, 96, 120, 144, 192, 240, 288 and 336 hours after injection respectively and then centrifuged at 3,000 rpm for 20 minutes. The supernatants were stored at −70° C. Additional blood samples were collected and stored for the rats dosed with Roferon-A® at 0.08, 0.25, and 8 hours after injection.

The interferon concentration in serum samples was quantified by ELISA method. Before performing the assay, the serum dilution-fold was optimized and the plate was laid out for standards, controls, and specimens. The absorbances at wavelength 450 nm and 600 nm were acquired by SoftMax® Pro 5 software. The Cmax, Tmax, and AUC values and the elimination phase half-life ($T_{1/2}$) from the IFN concentrations in serum were calculated by PK Solutions 2.0™ software.

Figure 10:
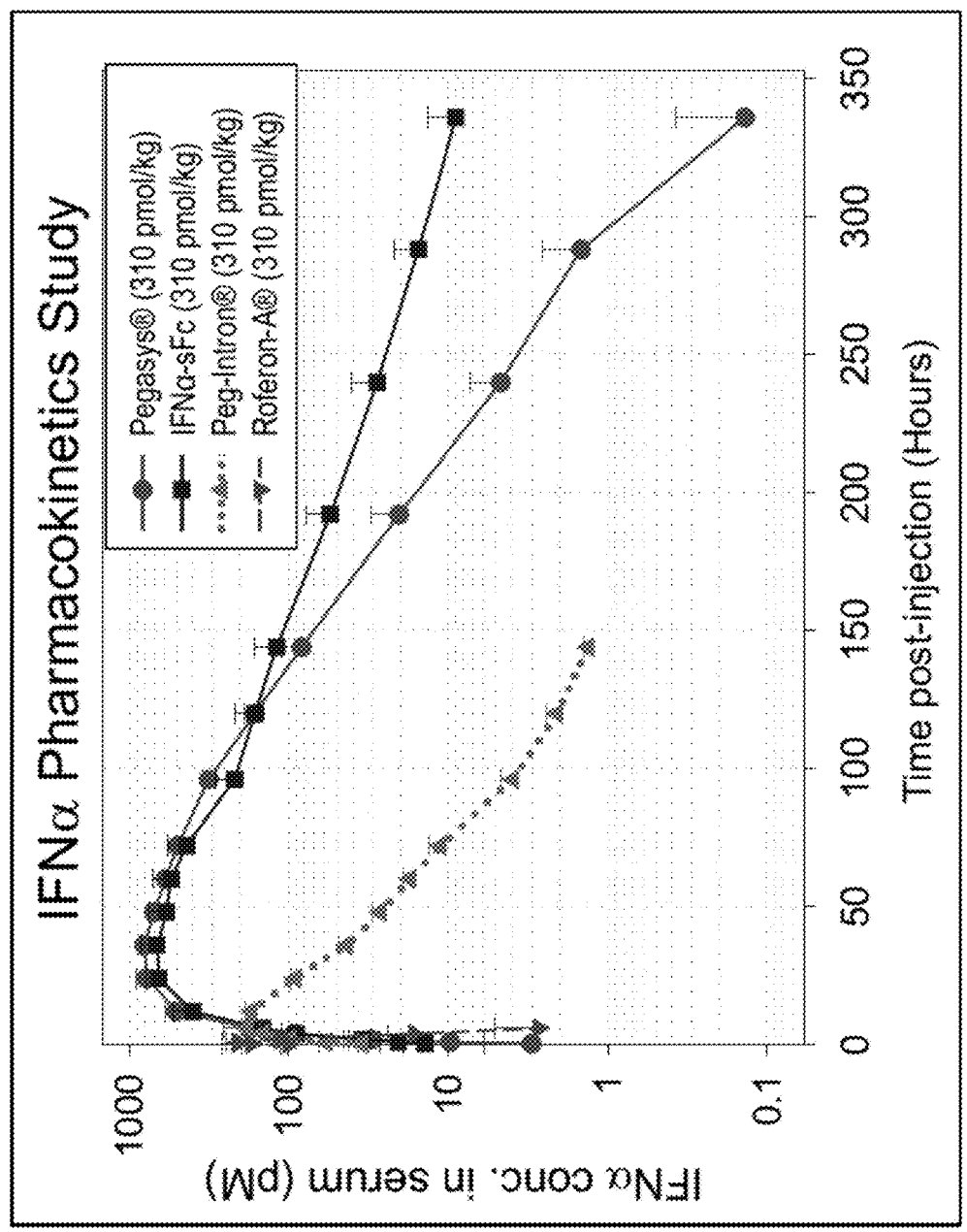
FIG. 10 is a graph showing the pharmacokinetics (PK) profile of a single dose subcutaneous (S.C.) administration of Pegasys® (circle), interferon alpha single chain Fc fusion protein (IFNα-sFc) (rectangle), Peg-Intron® (regular triangle), and Roferon-A® (inverted triangle) in rats. The half-life of IFNα-sFc is about 50.2 hours, which is longer than other interferon products.

The subcutaneous (S.C.) pharmacokinetic profiles of the different treatment Groups after administration with single dose are shown in FIG. 10 with their mean pharmacokinetic features shown in Table 9. The half-life of Pegasys®, IFNα-sFc, Peg-Intron® and Roferon-A® was 23.2, 50.2, 20.8 and 0.73 hrs, respectively. The AUCs of Pegasys®, IFNα-sFc, Peg-Intron® and Roferon-A® were 64694.5, 60621.9, 5307.6 and 489.2 pM/h, respectively. The Tmax of Pegasys®, IFNα-sFc, Peg-Intron®, and Roferon-A® were 32.0, 32.0, 6.0 and 0.67 hr, respectively.

Roferon-A® is a first generation recombinant IFNα product. Pegasys® and Peg-Intron® are both second generation products of IFNα, with PEG (polyethylene glycol) coupled to the native IFNα. The inclusion of PEG has previously been shown to significantly prolong the half-life of IFNα compared to the non-pegylated form. The increase in half-life by PEG was also observed in this Example, as shown by the pharmacokinetic data reported in Table 9 and FIG. 10 (compare the data for Pegasys® and Peg-Intron® with the data for Roferon-A®).

Table 9 and FIG. 10 also show that the half-life of IFNα is prolonged even further, compared to Pegasys®, Peg-Intron®, and Roferon-A®, when it is present in a single chain Fc fusion protein of the present disclosure. Specifically, the half-life of IFNα-sFc is more than 2 times longer than the two PEGylated interferons (Pegasys® and Peg-Intron®) and more than 68 times longer than recombinant IFNα (Roferon-A®).

EXAMPLE 15

Biological Activity Assay for IFNα-sFc

Antiviral activity of the IFN was determined by a cytopathic effect (CPE) inhibition assay. In brief, the wells of 96-well plates were seeded with $1.0 \times 10^4$ A549 cells and incubated at 37° C. in a 5% $CO_2$ incubator for 24 hours.

When cell growth formed confluent monolayers, cells were treated with various concentrations and forms of IFNα. Five-fold serial dilutions of the IFNs were prepared starting at a concentration of 178 ng/mL. The final volume of IFN added to the wells was 100µl After 24 hours, the medium was removed, and the cells were infected with murine encephalomyocarditis virus (EMCV) at a titer of $6 \times 10^4$ PFU/mL and incubated for 24 hours. Cytopathic effect (CPE) was observed in virus control wells without any interferon. 20 µl of MTS solution was added to each well, and the plates were incubated at 37° C. in a 5% $CO_2$ incubator for 3 hours. The stained cells were analyzed by spectrophotometry at OD 490 nm in an automated plate reader. All assays were performed in triplicate and the overall mean was calculated.

The percentage inhibition of viral CPE at each concentration of IFN was calculated using the formula below:

"Inhibition (%)=(OD test well−OD virus control)/
(OD cell control−OD virus control)"

A four-parameter logistic curve and a 50% viral replication inhibition dose were both calculated by Sigma Plot software.

Figure 11:
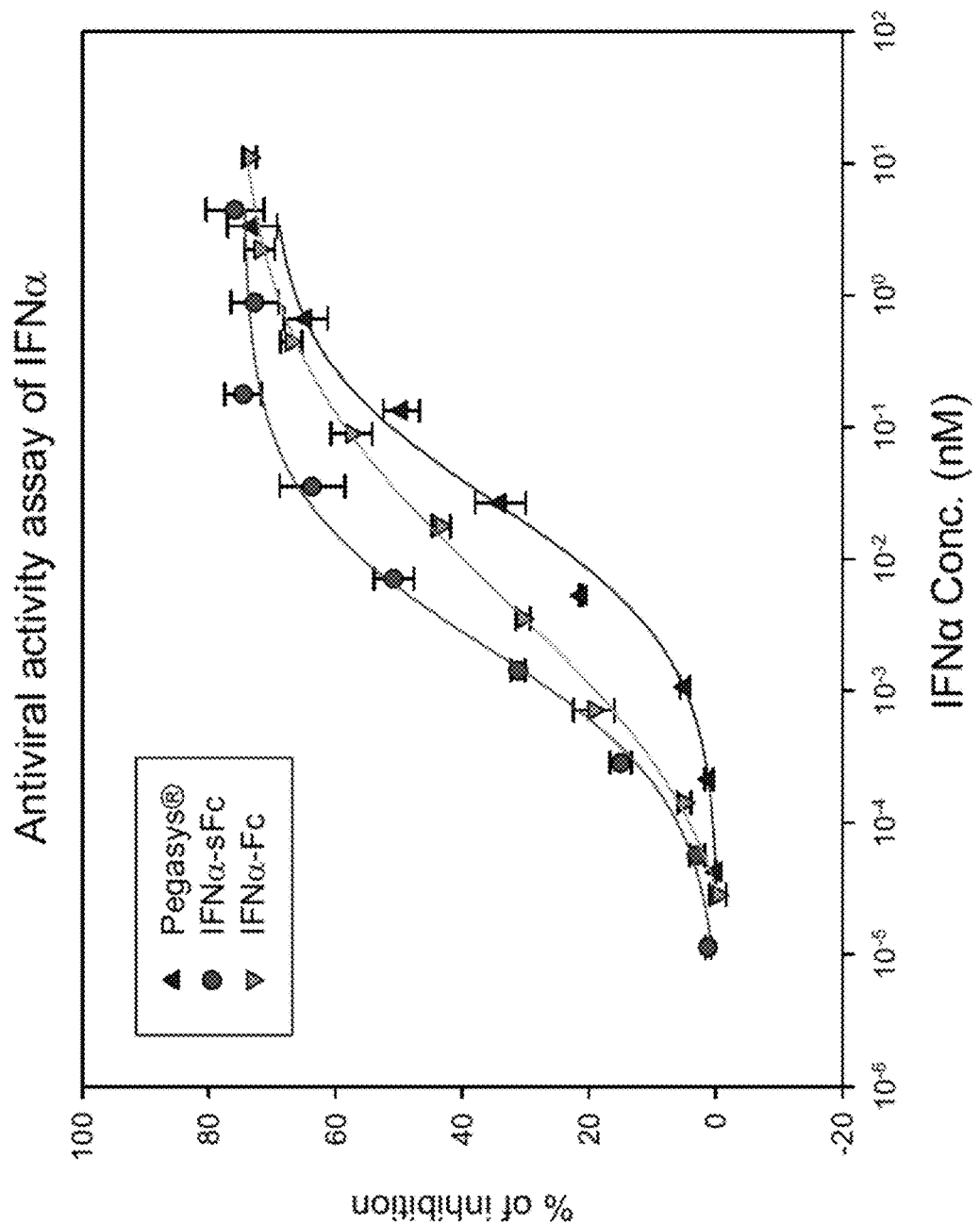
FIG. 11 is a graph showing the anti-virus activity of interferon alpha single chain Fc fusion protein (IFNα-sFc) (circle), Pegasys® (regular triangle) and interferon alpha Fc fusion protein (IFNα-Fc) (inverted triangle) in rats. The antiviral activity ($IC_{50}$) of IFNα-sFc is about 0.0061 nM, which is far better than that of IFNα-Fc ($IC_{50}$=0.0313 nM) and Pegasys® ($IC_{50}$=0.0894).

In addition, the antiviral activity of IFNα-sFc (single chain) was compared to IFNα-Fc (dimer) and the results are shown in FIG. 11 and Table 10. The antiviral activity of IFN-α-sFc ($IC_{50}$=0.0061 nM) was 5.1-fold higher than IFN-α-Fc ($IC_{50}$=0.0313 nM) and 14.7-fold higher than Pegasys® ($IC_{50}$=0.0894).

Summary

The results obtained in Examples 14 and 15 demonstrate that the IFNα single chain Fc fusion protein of this disclosure (IFNα-sFc) has improved biological properties and advantages compared to other IFNα products, including: (1) reduction in production cost by increasing purification yield through Protein A chromatography, (2) enhancement in anti-viral activity, (3) longer serum half-life, resulting in a decrease in dosing frequency, and (4) reduction in renal clearance. Although the half-life of a traditional dimerized Fc fusion protein (IFNα-Fc) and Pegasys® were prolonged compared to Roferon-A®, their biological activities were lower than IFNα-sFc. The lower biological activities seen with IFNα-Fc and Pegasys® is likely caused, at least in part, by the steric interference of receptor binding with the larger fusion molecules (i.e., the Fc dimer in IFNα-Fc and the branched 40 kDa PEG chain in Pegasys®).

The results shown in FIGS. 10-11 and Tables 9-10 demonstrate that the single chain Fc modification of this disclosure produces an IFNα having a prolonged half-life and enhanced biological activity compared to other forms of IFNα. These results suggest that the modification of the present invention can be used to produce highly potent and efficient pharmaceutical compositions containing peptide and protein based treatments.

EXAMPLE 16

Comparison of the Respective Binding Affinities of IFNα-sFc (Single Chain) and IFNα-Fc (Dimer) to Interferon Alpha Receptor 1 (IFNAR1) and Interferon Alpha Receptor 2 (IFNAR2)

The binding affinities of the interferon fusion proteins were determined by Kinetic/Affinity assay.

Briefly, 5 µg/mL rhIFN alpha receptor 2 (IFNAR2) (Sino biotechnology, CN.: 10359-H08H) prepared in immobilization buffer (10 mM sodium acetate buffer, pH 4.0). The rhIFNAR2 ($R_L$=800 RU) was immobilized on a CM5 sensor chip (GE, CN.: BR-1003-99) through conventional amine coupling on a Surface Plasmon Resonance (SPR) machine (GE, Model: Biacore X100). Sample solutions containing 12.5 to 200 nM IFNα-sFc or IFNα-Fc were prepared by a 2-fold series dilution with running buffer (PBS with 0.005% Tween 20, pH 7.4). Solutions prepared in previous steps were diluted by 2-fold series with running buffer to prepare 6.25 to 100 nM IFNα-sFc or IFNα-Fc single injection solutions. Then, 200 nM IFN-alpha receptor 1 (IFNAR1) (Sino biotechnology, CN.: 13222-H08H) solution was mixed with equal volume of IFN single injection solution prepared in previous step to prepare IFN-IFNAR1 mixture. The concentration of IFNAR1 was 100 nM, while the concentration of IFNα-sFc or IFNα-Fc ranged from 6.25 nM to 100 nM. The equilibrium association constant (Ka) and equilibrium dissociation constant (Kd) values of IFNα-sFc or IFNα-Fc were analyzed by BIAevaluation software to calculate the binding constant (KD) values by the Kd and Ka.

Figure 12A:
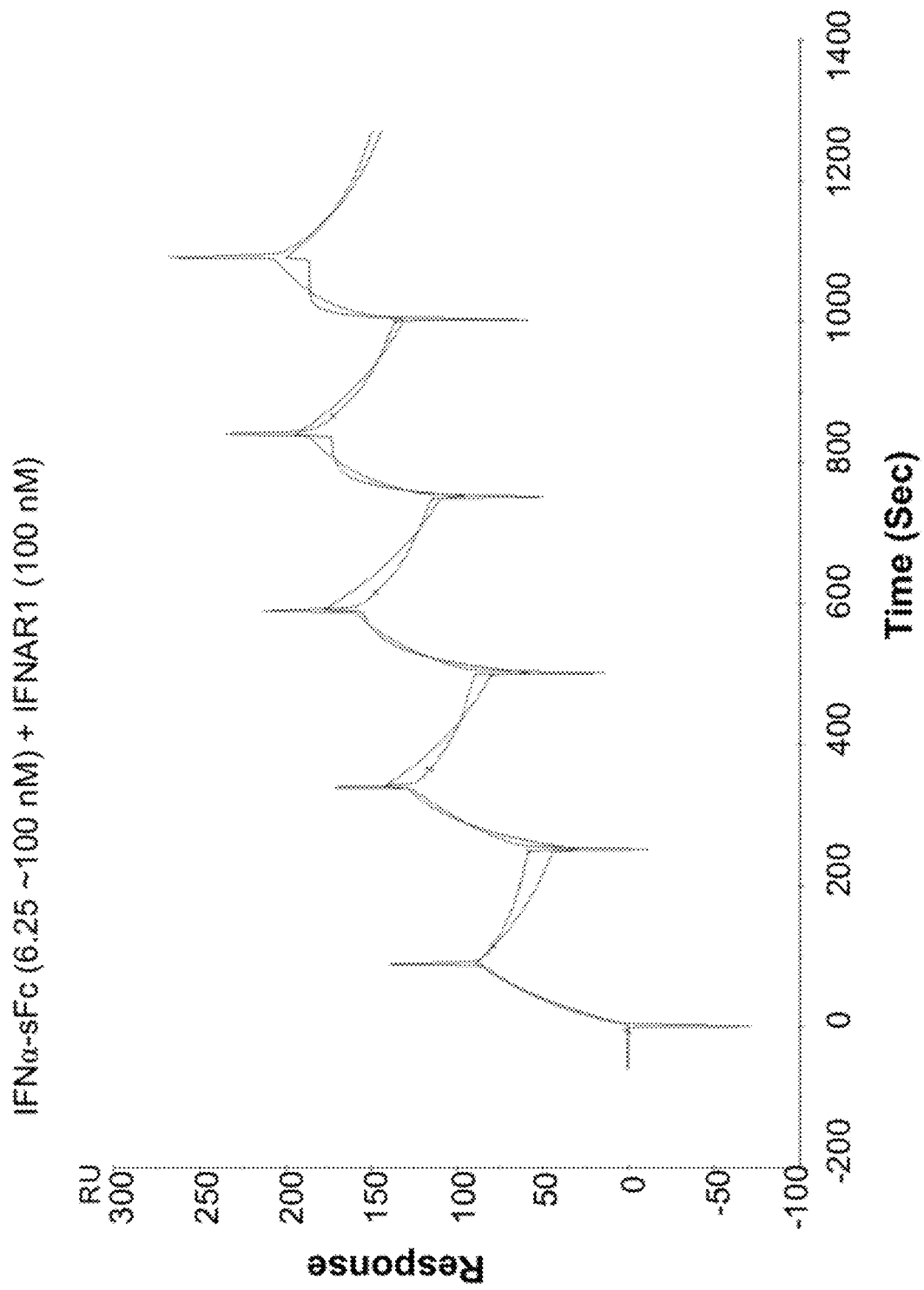
FIGS. 12a to 12b illustrate the association profiles of IFNα-sFc with Interferon-alpha receptor 1 (IFNAR1) (FIG. 12a) and IFNα-Fc with IFNAR1 (FIG. 12b).
Figure 12B:
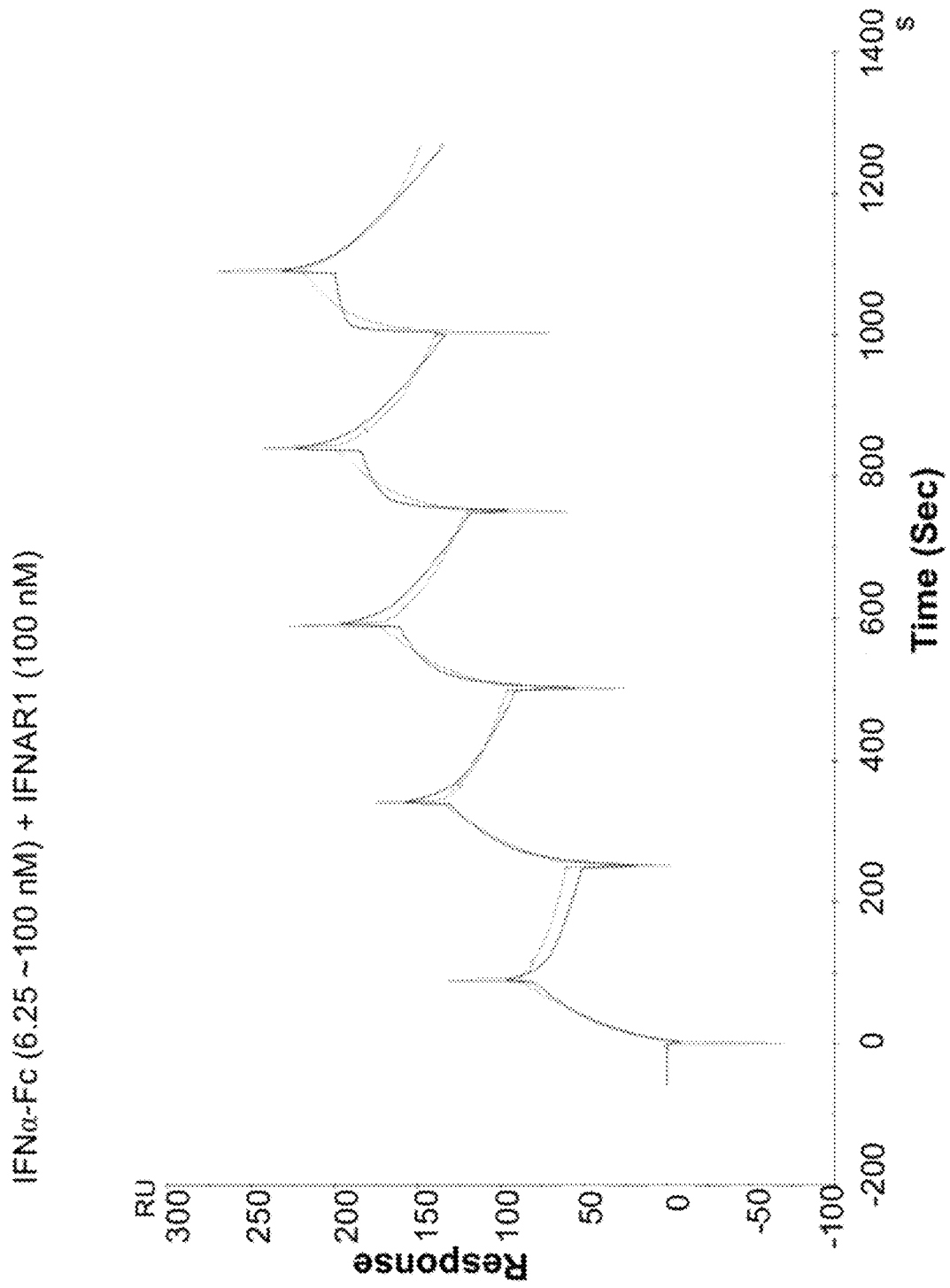

As shown in FIGS. 12a-12b, IFNα-sFc-IFNAR1 and IFNα-Fc-IFNAR1 had similar binding profiles. Specifically, Table 11 shows that the binding associations of the IFNs were relatively similar, with IFNα-sFc having a Ka of 1.4E+06 l/Ms and IFNα-Fc having a Ka of 3.3E+06 l/Ms, respectively. However, in the dissociation stage, IFNα-sFc-IFNAR1 had a slower dissociation profile (Kd) than that of IFNα-Fc-IFNAR1. As shown in Table 11, the dissociation (Kd) of IFNα-sFc and IFNα-Fc from IFNAR1 was 5.6E−03 and 5.6E−02 l/s, respectively. The affinity of interaction (KD) of IFNα-sFc and IFNα-Fc to IFNAR was determined to be 4.0E−09 and 1.7E−08 nM, respectively, based on the association (Ka) and dissociation (Kd) profiles observed. Therefore, the affinity of IFNα-sFc was 4.25-fold higher than IFNα-Fc for forming the ternary complexes.

The binding affinity results observed in this Example further support the theory discussed in the preceding Example that IFNα-sFc has enhanced biological activities, compared to IFNα-Fc, is likely due to less steric interference in receptor binding for the single chain Fc compared to the Fc dimer.

EXAMPLE 17

Granulocyte-Colony Stimulating Factor Single Chain Fc Fusion Protein (GCSF-sFc)

1. Fusion Protein

In this example, a fusion protein was prepared having a structure of formula 1 discussed above:

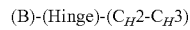

(B)-(Hinge)-($C_H2$-$C_H3$)

wherein:
the bioactive molecule (B) is granulocyte-colony stimulating factor (GCSF) protein (SEQ ID NO: 71);
the hinge region (Hinge) is a mutated IgG1 hinge (SEQ ID NO: 23); and
($C_H2$-$C_H3$) is a $C_H2$-$C_H3$ of IgG1 (SEQ ID NO: 62).

The full-length amino acid sequence of the GCSF-sFc fusion protein is shown in the Sequence Listing as SEQ ID NO: 72.

2. Expression Vector

Figure 13:
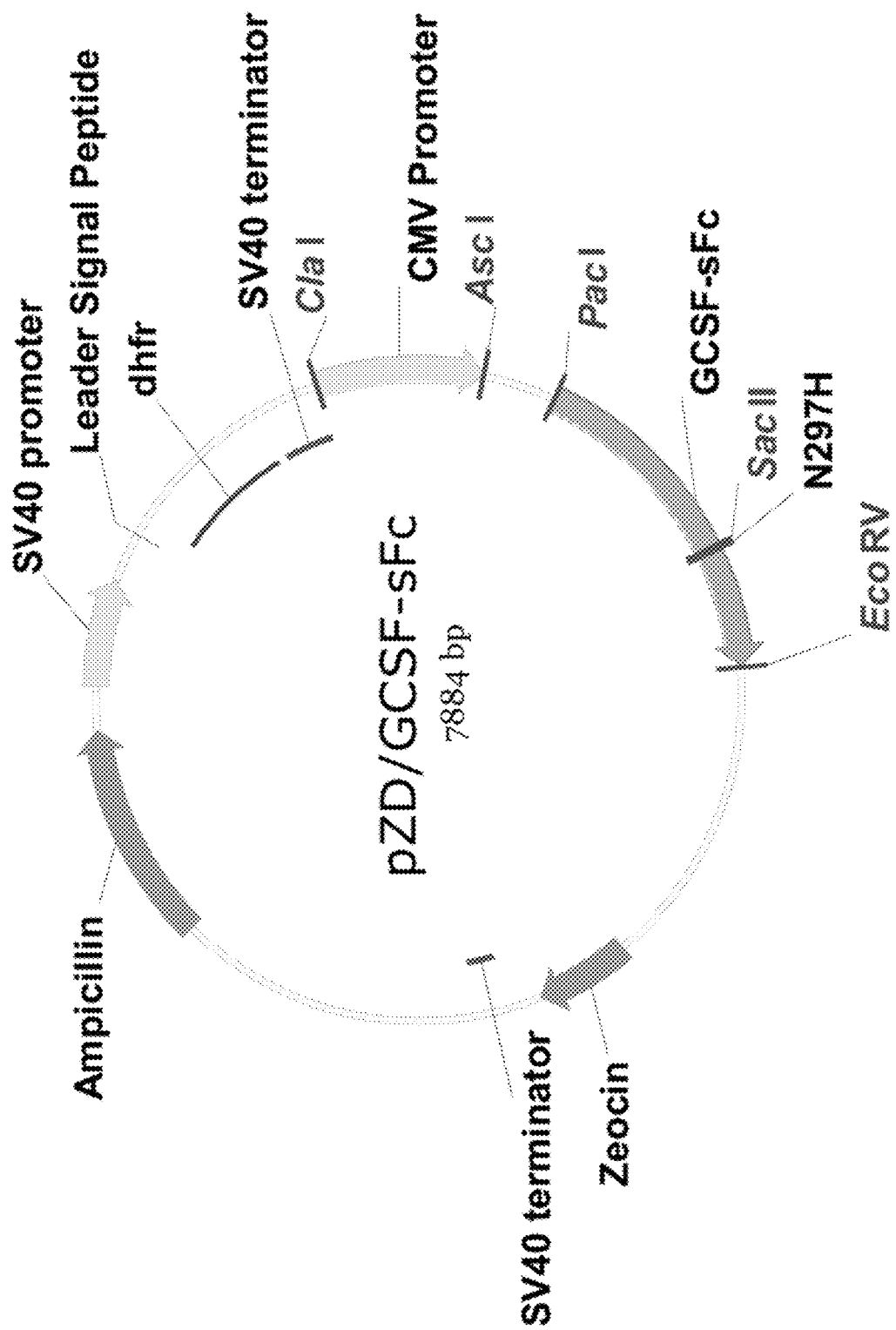
FIG. 13 illustrates a plasmid map of pZD-GCSF-sFc. The pZD/GCSF-sFc plasmid encodes an IFNα8-sFc fusion protein according to an embodiment of the present invention.

The GCSF-sFc was produced using a DNA expression vector. The DNA fragment of the granulocyte-colony stimulating factor single chain Fc fusion protein (GCSF-sFc) was assembled using overlapping primers by the method of assembly polymerase chain reaction (PCR). The assembled GCSF-sFc fragment was then ligated into PacI and EcoRV sites of pZD vector (pcDNA3.1Neo, Invitrogen, Carlsbad, CA, cat. no. V790-20 with dhfr gene) to obtain pZD-GCSF-sFc as shown in FIG. 13 and then transformed into E. coli. The expression vector construct contained the zeocin-resistance gene as a selection marker.

EXAMPLE 18

Establishment of Stable Recombinant Cell Lines Producing GCSF-sFc $CHO_{dhfr-}$ cells were trypsinized and resuspended at a concentration of $3×10^6$ cells/mL in CP-T buffer (Cyto pluse Cat. CP-T). 0.2 mL of cell suspension ($6×10^5$ cells) was transfected with 10 µg of plasmid pZD-GCSF-sFc by electroporation (PA4000 PulseAgile® electroporator, Cyto Pulse Sciences). After 48 hrs of growth in non-selective medium, the transfectants were incubated in the selective complete medium containing IMDM, 10% fetal bovine serum, Zeocin (Invitrogen Cat. 1486406) and 5 nM MTX (Sigma Cat. BCL5707V) to obtain high yield clone zG3-17-41. The expression of the secreted fusion protein in the culture medium was detected and quantified by Q-ELISA.

The original zG3-17-41 cells were cultivated in a 10-cm dish containing IMDM supplemented with 10% FBS, zeocin, and 0.1 µM MTX. Cells were maintained in a 37° C. humidified 95% air/5% $CO_2$ incubator (Model 3326, Forma scientific). In order to adapt the cells in serum-free culture medium, the medium was changed from IMDM to JRH serum-free medium supplemented with 5% FBS, zeocin, and 0.1 µM MTX. When cells became stable, the cells were detached from 10-cm dish by trypsinization and then transferred to spinner flasks containing 50 mL JRH serum-free medium supplemented with the same percentage of FBS. Cells were adapted into lower serum conditions by stepwise decreasing the FBS percentage from 10% to 0% in spinner flasks.

The concentration of GCSF-sFc fusion protein in serum samples was quantified by GCSF-sFc ELISA analysis. Absorbance at wavelength 450 nm and 600 nm was acquired by SoftMax® Pro 5 software. High-yield clones were successfully obtained by selection, limiting dilution and stepwise MTX challenges to produce finally the fusion protein comprising the recombinant GCSF linked to single chain Fc (i.e., GCSF-sFc). The resulting fusion protein was purified for further in vitro or in vivo biological activity assays and pharmacokinetics studies.

EXAMPLE 19

Chromatographic Purification of GCSF-sFc

Figure 14:
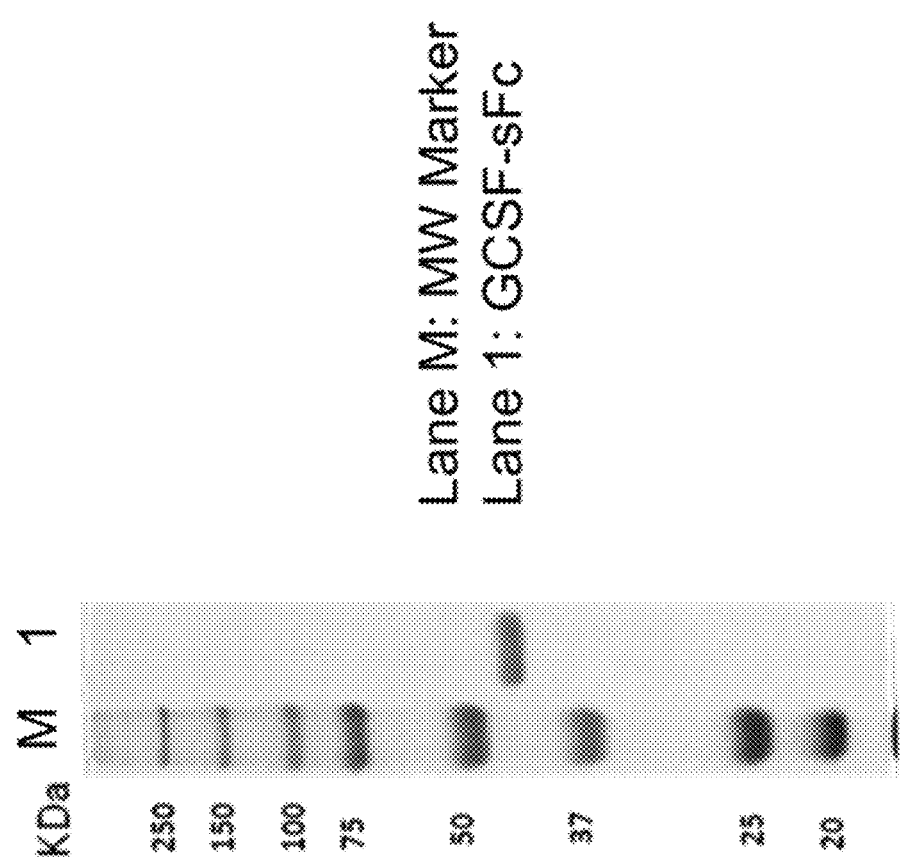
FIG. 14 illustrates an SDS-PAGE profile, by Coomassie blue staining, of GCSF single chain Fc fusion protein (GCSF-sFc) produced by methods disclosed herein. Lane M is a molecular weight marker (marker contains recombinant proteins in size of 20, 25, 37, 50, 75, 100, 150, and 250 kDa). Lane 1 is an eluate of GCSF-sFc.

Protein A based resin (MabSelect SuRe™) was used to purify GCSF-sFc. After purification, the corresponding recovery rate was analyzed by quantitative ELISA, and the respective purity by SDS-PAGE. The detailed purification process for GCSF-sFc is described below.
MabSelect SuRe™ Purification Culture medium from the high yield GCSF-sFc producing cell line was applied to a Protein A based MabSelect SuRe™ column (GE; Cat. no. 11-0034-93) with a loading ratio at about 3.4 mg for 1 mL resin. After 2 washing steps, the fusion protein was eluted with 0.1M Glycine pH3.0 elution buffer. The main peak eluted was analyzed by reverse phase HPLC (RP-HPLC). The MabSelect SuRe™ eluate was also analyzed by Q-ELISA to determine the quantity and recovery rate. The eluates of purified GCSF-sFc sample were also analyzed by SDS-PAGE. FIG. 14 reveals the GCSF-sFc fusion protein revealed as a major band by the SDS-PAGE. In summary, the GCSF-sFc could be captured by MabSelect SuRe™ efficiently.

EXAMPLE 20

Pharmacokinetic Study for GCSF-sFc

Nine rats, weighing from 180-200 g, were purchased from BioLASCO Taiwan Co., Ltd. All rats were quarantined and acclimatized for four days prior to the initiation of the pharmacokinetic (PK) studies. The rats were divided into three testing groups for the PK studies: (1) GCSF-sFc, (2) Lenograstim (Granocyte®), a recombinant GCSF, and (3) Peg-filgrastim (Neulasta®), a PEGylated form of recombinant human GCSF. The rats were dosed at 221.43 µg/Kg for GCSF-sFc and a molar equivalence of 100 µg/Kg for Lenograstim and Peg-filgrastim. All GCSF products were freshly prepared with sample diluents, 0.2% bovine serum albumin (AppliChem, CN: A0850,0250) in phosphate-buffered saline. The rats were grouped and labeled with fur dye. All injections were administered to the rats via the site of dorsal neck for subcutaneous (S.C.) route.

Blood samples were collected at 5 min, 0.5, 1, 2, 3, 8, 12, 24, 36, 48, 72, 96, 120, 144, and 168 hours after injection respectively and then centrifuged at 3,000 rpm for 20 minutes. The supernatants were stored at −70° C.

The GCSF concentrations in serum samples were quantified by ELISA method using paired antibodies (R&D System, CN: MAB214 and R&D System, CN: BAF214) to bind and detect GCSF. Before performing the assay, the serum dilution-fold was optimized and the plate was laid out for standards, controls, and specimens. The absorbances at wavelength 450 nm and 600 nm were acquired by SoftMax® Pro 5 software. The Cmax, Tmax, and AUC values and the elimination phase half-life ($T_{1/2}$) from the GCSF concentrations in serum were calculated by PK Solutions 2.0™ software.

Figure 15:
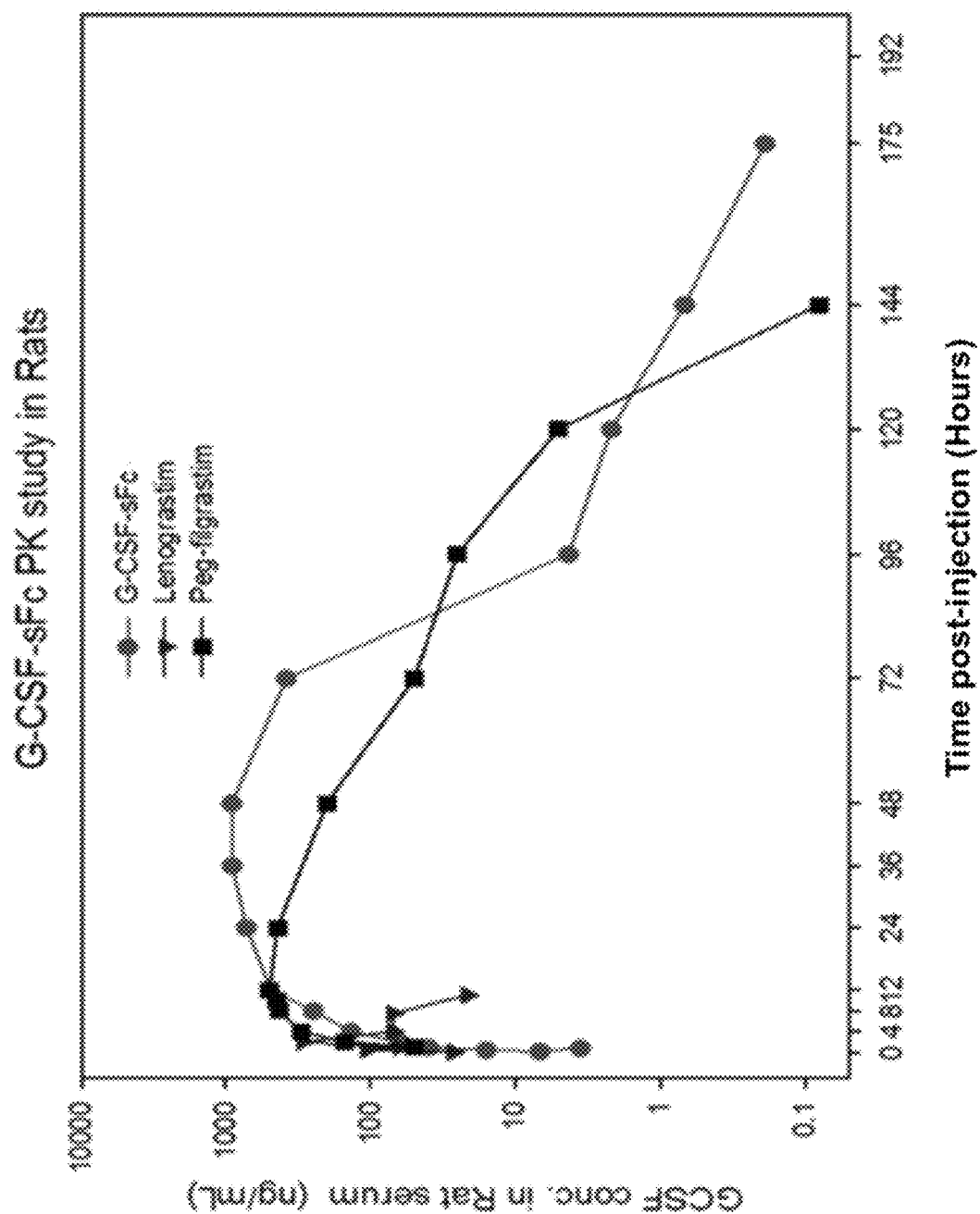
FIG. 15 is a graph showing the pharmacokinetics (PK) profile of a single dose subcutaneous (S.C.) administration of GCSF single chain Fc fusion protein (GCSF-sFc) (circle), Lenograstim (Granocyte®) (triangle), and Peg-filgrastim (Neulasta®) (rectangle) in rats. The half-life of GCSF-sFc is about 17.16 hours, which is longer than that of Lenograstim (4.1 hours) and Peg-filgrastim (12.0 hours).

The subcutaneous (S.C.) pharmacokinetic profiles of the respective GCSFs in rats after administration with single dose are shown in FIG. 15 with their mean pharmacokinetic features shown in Table 12. The half-life of GCSF-sFc, Lenograstim, and Peg-filgrastim was 17.16, 4.1 and 12.0 hrs, respectively. The Cmax of GCSF-sFc, Lenograstim, and Peg-filgrastim was 906.9, 156.4 and 480.8 ng/mL, respectively. The Tmax of GCSF-sFc, Lenograstim, and Peg-filgrastim was 48, 0.5 and 10.3 hrs, respectively. The AUC of GCSF-sFc, Lenograstim, and Peg-filgrastim was 50624, 790-1292, and 23202±2921 ng-h/mL, respectively.

Lenograstim is a first generation recombinant GCSF product. Peg-filgrastim is a second generation product of GCSF coupled to PEG (polyethylene glycol). The inclusion of PEG has previously been shown to prolong the half-life of GCSF when compared to the first generation product (Lenograstim). The increase in GCSF half-life with PEG was also observed in this Example, as shown in the pharmacokinetics data reported in Table 12 and FIG. 15 (compare the data for Lenograstim with the data for Peg-filgrastim).

Table 12 and FIG. 15 also show that the half-life of GCSF is prolonged even further, compared to Lenograstim and Peg-filgrastim, when GCSF is present in a single chain Fc fusion protein of the present disclosure. Specifically, the half-life of GCSF-sFc is nearly one and a half times longer than PEGylated GCSF (Peg-filgrastim) and more than 4 times longer than recombinant GCSF (Lenograstim).

EXAMPLE 21

Biological Activity Assay for GCSF-sFc

Neutropenic mice were used to analyze GCSFs potency in comparison to the native GCSF, i.e. Lenograstim (Granocyte®). In this study, 30 male BALB/cByJNarl mice aged 6 weeks were divided into six groups (i.e., five mice per group). All mice were treated with CPA (Cyclophosphamide monohydrate; Sigma, CN: C7397) (100 mg/kg) on day 0. Group A as the control group only received a 0.9% NaCl/0.1% BSA solution on day 1. Three reference groups received Lenograstim (Chugai, CN.: N3L212) in a single shot (Groups B1 and B2) or four shots (Group B3) containing a dose of 51.02, 116.07 and 12.75 μM/kg, respectively. Two test groups received a single shot of GCSF-sFc containing a dose of 51.02 μM/kg (Group C1) and 116.07 μM/kg (Group C2). The groups that received a single shot (Groups A, B1, B2, C1, and C2) were injected on day 1 and the group receiving 4 shots (Group B3) was injected on days 1, 2, 3 and 4. All shots were administered via the route of subcutaneous injection. Blood samples were collected each day after administration and analyzed by Hematoanalyzer (HEMAVET 950 LV) until termination of the study. A blood sample was also taken 3 days prior to CPA treatment (day −3) for reference. The experimental design used in this study is summarized in Table 13.

Figure 16:
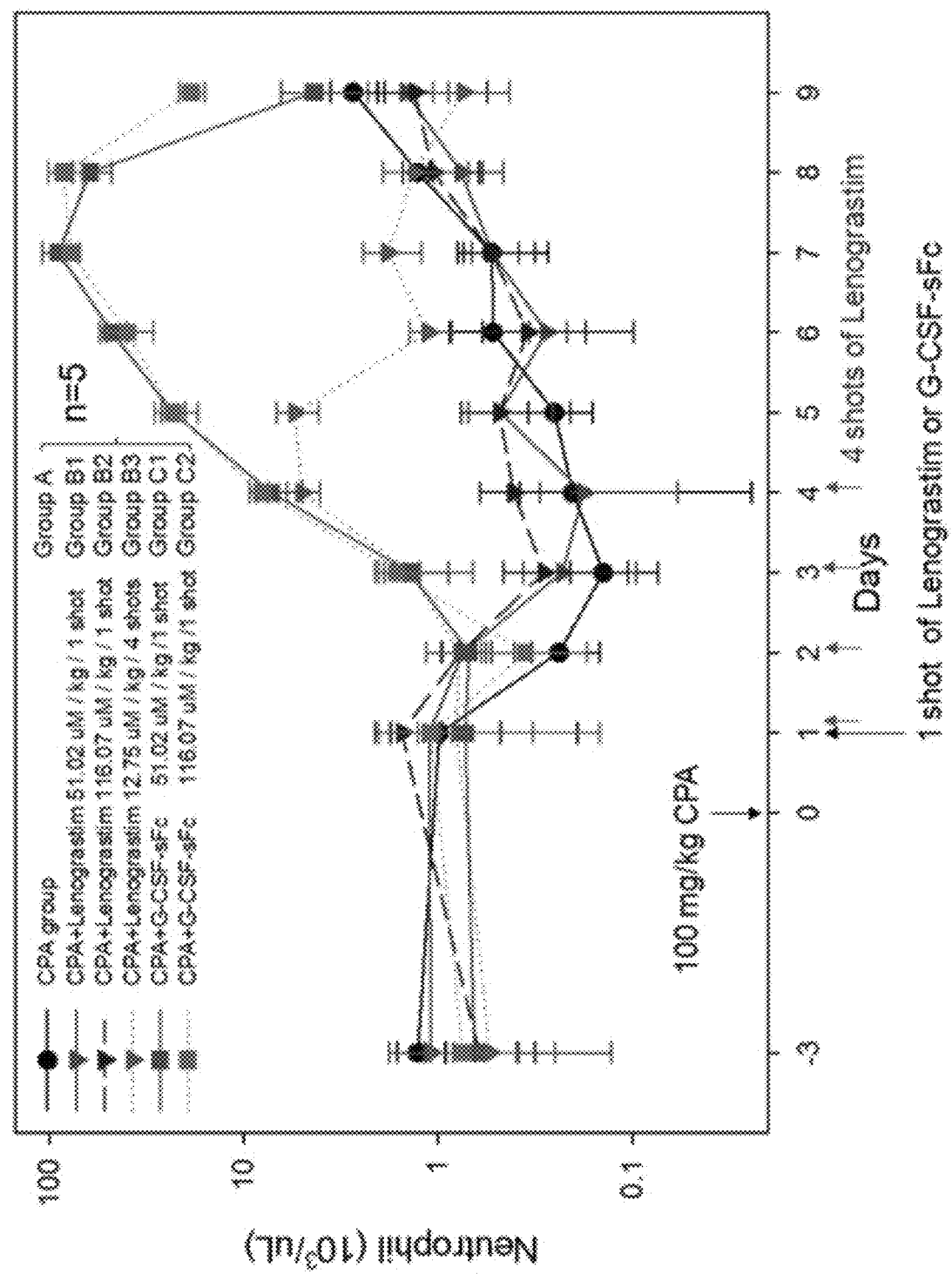
FIG. 16 is a graph showing the biological activity of single dose (groups B1 and B2) or four doses (Group B3) subcutaneous (S.C.) administration of Lenograstim and a single dose subcutaneous (S.C.) administration of GCSF single chain Fc fusion protein (GCSF-sFc) (Groups C1 and C2). The GCSF-sFc has a higher activity to enhance the neutrophil differentiation and proliferation in mice than Lenograstim.

FIG. 16 shows that pre-treating the mice with CPA caused neutropenia, i.e., a reduced the neutrophil counts in the blood of treated mice (compare days −3 and 0 with day 1 in all samples). However, the neutropenia was found to be temporary and the level of neutrophils slowly returned to pre-CPA treatment levels after about 8 days in the control group (see results for Group A). A single shot of Lenograstim at day 1, with either a mid-dose of 51.02 μM/Kg (Group B1) or a high-dose of 116.07 μM/Kg (Group B2), did not have any appreciable effect in increasing the neutrophil levels above those observed in the CPA control group during the observation period (compare Groups B1 and B2 with Group A). Multiple administrations (4 shots) of Lenograstim following CPA treatment (Group B3) had some effect in increasing neutrophil levels compared to Groups A, B1 and B2 (see Group B3, days 3-5). However, the observed effect was minimal and short-lived because neutrophil levels were barely raised above the normal range and the levels quickly decreased to the normal levels following the multiple administration period (see Group B3, days 5 et seq).

In contrast, administration of a single administration of a mid-dose (51.02 μM/Kg) or high dose (116.07 μM/kg) of GCSF-sFc following CPA treatment efficiently raised the neutrophil levels significantly above the control group and all of the groups treated with Lenograstim (compare Groups C1 and C2 with Groups A, B1, B2, and B3).

Thus, the GCSF single chain Fc fusion protein of the present disclosure (GCSF-sFc) has a longer half-life and is more potent and efficient in enhancing neutrophil differentiation and proliferation in a neutropenic animal disease model compared to the native and PEGylated forms of GCSF.

EXAMPLE 22

Interferon Beta Single Chain Fc Fusion Protein (IFNβ-sFc)

1. Fusion Protein

In this example, a fusion protein was prepared having a structure of formula 1 discussed above:

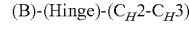

wherein:
the bioactive molecule (B) is interferon beta (IFNβ) protein (SEQ ID NO: 73);
the hinge region (Hinge) is a mutated IgG1 hinge (SEQ ID NO: 23); and
($C_H2$-$C_H3$) is a $C_H2$-$C_H3$ of IgG1 (SEQ ID NO: 63).

The full-length amino acid sequence of the IFNβ-sFc is shown in the Sequence Listing as SEQ ID NO: 74.

2. Expression Vector

Figure 17:
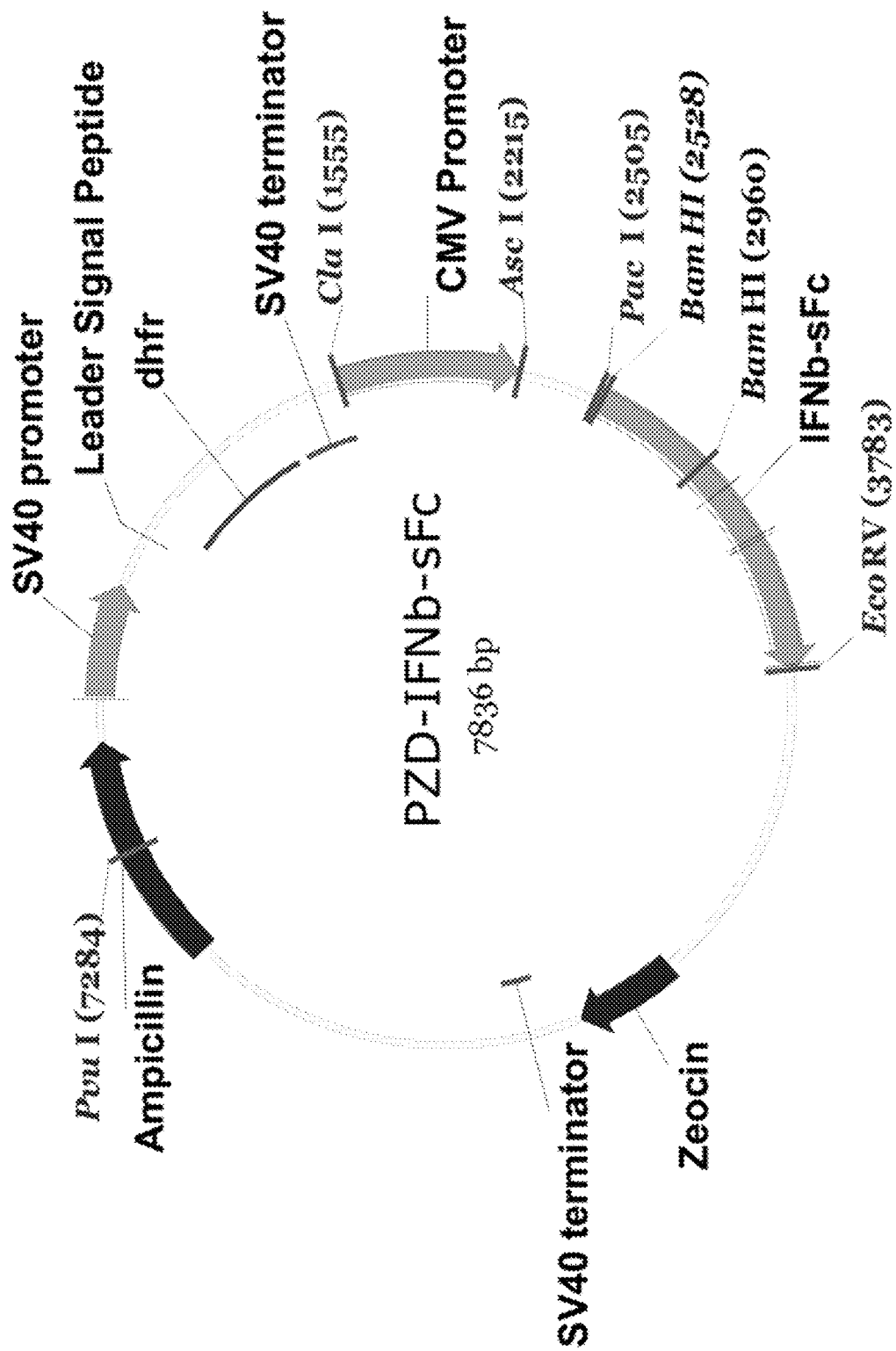
FIG. 17 is a plasmid map of pZD-IFNβ-sFc. The pZD-IFNβ-sFc plasmid encodes an IFNβ-sFc fusion protein according to an embodiment of the present invention.

The IFNβ-sFc was produced using a DNA expression vector. The DNA fragment of the IFNβ-sFc was assembled using overlapping primers by the method of assembly polymerase chain reaction (PCR). The assembled IFNβ-sFc fragment was then ligated into PacI and EcoRV sites of pZD vector (pcDNA3.1Neo, Invitrogen, Carlsbad, CA, cat. no. V790-20 with dhfr gene) to obtain pZD/IFNb-sFc as shown in FIG. 17 and then transformed into E. coli. The expression vector construct contained the zeocin-resistance gene as a selection marker.

EXAMPLE 23

Establishment of Stable Recombinant Cell Lines Producing IFNβ-sFc $CHO_{dhfr-}$ cells were trypsinized and resuspended at a concentration of $3 \times 10^6$ cells/mL in CP-T buffer (Cyto pluse Cat. CP-T). 0.2 mL of cell suspension ($6 \times 10^5$ cells) was transfected with 10 μg of plasmid pZD-IFNβ-sFc by electroporation (PA4000 PulseAgile® electroporator, Cyto Pulse Sciences). After 48 hrs of growth in non-selective medium, the transfectants were incubated in the selective complete medium containing IMDM, 10% fetal bovine serum, Zeocin (Invitrogen Cat. 1486406) and 5 nM MTX (Sigma Cat. BCL5707V) to obtain a high yield clone zG3-17-41. The expression of the secreted fusion protein in the culture medium was detected and quantified by Q-ELISA.

The original Z-BsFc cells were cultivated in a 10-cm dish containing IMDM supplemented with 10% FBS, zeocin, and 0.1 μM MTX. Cells were maintained in a 37° C. humidified 95% air/5% $CO_2$ incubator (Model 3326, Forma Scientific). In order to adapt the cells in serum-free culture medium, the medium was changed from IMDM to JRH serum-free medium supplemented with 5% FBS, zeocin, and 0.1 μM MTX. When cells became stable, the cells were detached from 10-cm dish by trypsinization and then transferred to spinner flasks containing 50 mL JRH serum-free medium supplemented with the same percentage of FBS. When confluency reached 90% in 3-5 days, cells were subcultured into spinner flask containing JRH serum-free medium supplemented with a lower percentage of FBS. Cells were adapted into lower serum conditions by stepwise decreasing the FBS percentage from 10% to 0% in spinner flasks.

The concentration of IFNβ-sFc fusion protein in serum samples were quantified by an in-house IFNβ-sFc ELISA kit. The serum dilution-fold was optimized and the plate layout for standards, controls, and specimens were determined before performing formal assays using the fusion protein. Absorbance at wavelength 450 nm and 600 nm was acquired by SoftMax® Pro 5 software. High-yield clones were successfully obtained by selection, limiting dilution and stepwise MTX challenges to produce finally the fusion protein comprising the recombinant IFN beta linked to single chain Fc (i.e., IFNβ-sFc). The resulting fusion protein was purified for further in vitro or in vivo biological activity assays and pharmacokinetics studies.

EXAMPLE 24

Chromatographic Purification of IFNβ-sFc

Protein A based resin (MabSelect SuRe™) was used to purify IFNβ-sFc. After purification, the corresponding recovery rate was analyzed by quantitative ELISA, and the respective purity by SDS-PAGE. The detailed purification process for IFNβ-sFc is described below.
MabSelect SuRe™ Purification Culture medium from the high yield IFNβ-sFc producing cell line was applied to a Protein A based MabSelect SuRe™ column (GE; Cat. no. 11-0034-93) with a loading ratio of about 1.58 mg for 1 mL resin. After 2 washing steps, the fusion protein was eluted with 0.1M Glycine pH3.0 elution buffer. The protein that eluted in the main peak from the MabSelect SuRe™ column was analyzed and found to be relatively pure, based on the sharp peak observed by reverse phase HPLC (RP-HPLC) and the sharp band obtained by SDS-PAGE (data not shown). The MabSelect SuRe™ eluate was also analyzed by Q-ELISA to determine the quantity and recovery rate as shown in Table 14.

EXAMPLE 25

Pharmacokinetic Study for IFNβ-sFc

Eight Lewis rats, weighing from 200-230 g, were purchased from BioLASCO Taiwan Co., Ltd. All rats were quarantined and acclimatized for four days prior to the initiation of the pharmacokinetic (PK) studies. The rats were divided into two testing groups for the PK studies: (1) natural fibroblast derived human IFNβ-1a (Rebif®) and (2) IFNβ-sFc. Rebif® and IFNβ-sFc were administered to the rats at a dose of 37 μg/Kg. All articles were freshly prepared with fresh sample diluents, 0.2% bovine serum albumin (AppliChem, CN: A0850,0250) in phosphate-buffered saline. The rats were grouped and labeled with fur dye. All injections were administered to the rats via the site of dorsal neck for subcutaneous (S.C.) route.

Blood samples were collected at 5 min, 0.5, 1, 4, 7, 12, 24, 36, 48, 72, 96, 120, 144, and 168 hours after injection respectively and then centrifuged at 3,000 rpm for 20 minutes. The supernatants were stored at −70° C.

The interferon concentrations in serum samples were quantified by VeriKine™ Human IFN Beta ELISA Kit (PBL assay science, CN.: 41410) for IFNβ. The absorbances at wavelength 450 nm and 600 nm were acquired by SoftMax® Pro 5 software. The Cmax, Tmax, AUC values, and the elimination phase half-life ($T_{1/2}$) from the interferon concentrations in serum were calculated by PK Solutions 2.0™ software.

Figure 18:
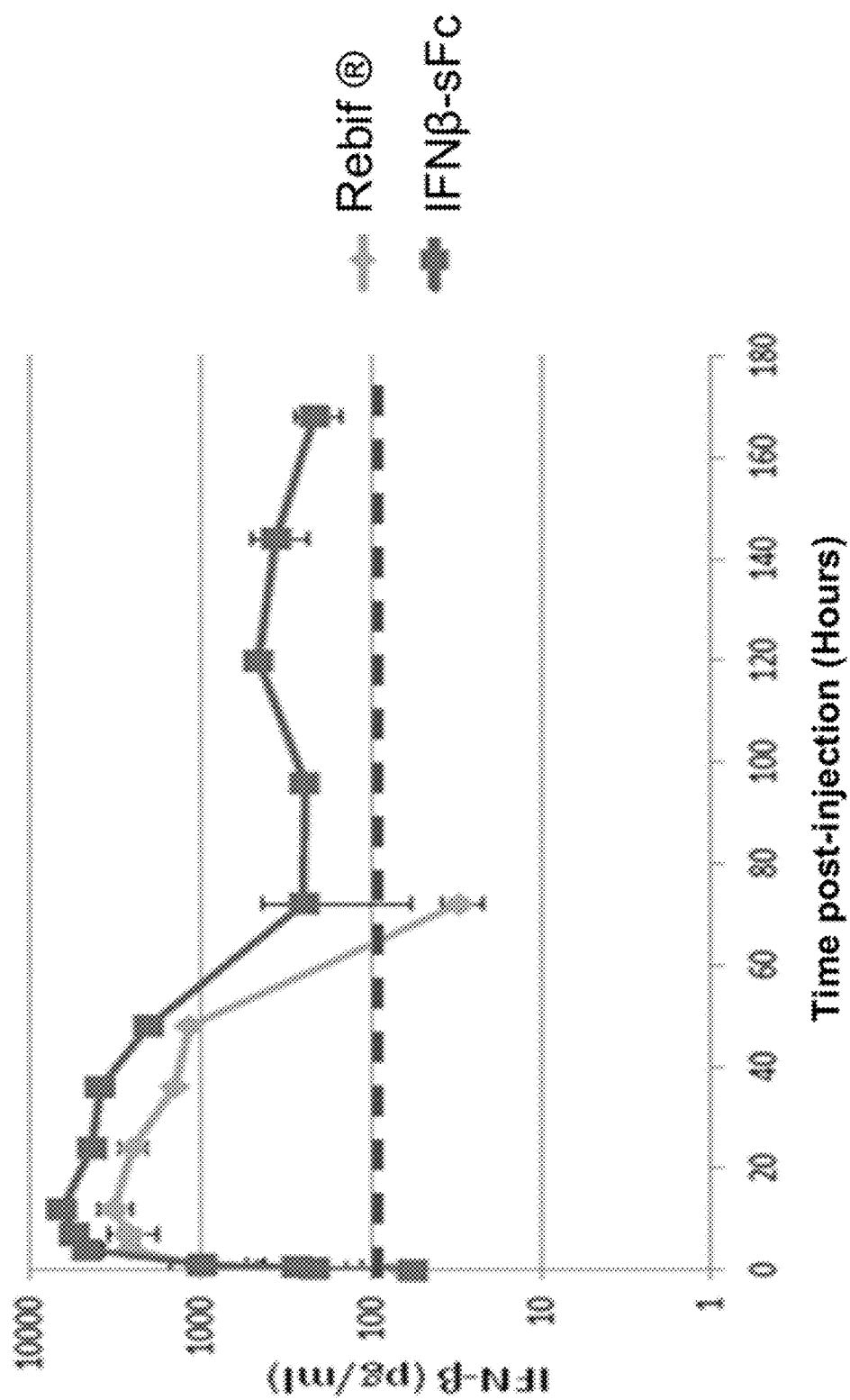
FIG. 18 is a graph showing the pharmacokinetics (PK) profile of a single dose subcutaneous (S.C.) administration of interferon β single chain Fc fusion protein (IFNβ-sFc) (rectangle) and Rebif® (rhombus) in rats. The half-life of IFNβ-sFc is about 31.89-37.7 hours, which is longer than that of Rebif® (18.92-23.57 hours).

The subcutaneous (S.C.) pharmacokinetic profiles of IFNβ in rats after administration with a single dose are shown in FIG. 18 and the mean pharmacokinetic features are reported in Table 15. The half-life of Rebif® and IFNβ-sFc was 18.92-23.57 and 31.89-37.7 hrs, respectively. The Cmax of Rebif® and IFNβ-sFc was 3.2±0.71 and 6.55±0.78 ng/mL, respectively. The Tmax of Rebif® and IFNβ-sFc was 12±0 and 9.55±3.61 hrs, respectively. The AUC of Rebif® and IFNβ-sFc was 115±18.38 and 273±2.83 ng-hr/mL, respectively.

The IFNβ-sFc of this invention exhibited improvement in half-life extension as shown in FIG. 18 and Table 15 when compared to that of Rebif® (the native form of IFNβ).

EXAMPLE 26

Biological Activity Assay for IFNβ-sFc

IFNβ is an anti-inflammatory cytokine and serves as one of the major drugs for multiple sclerosis (MS) treatment. MS is the most common inflammatory disease of the central nervous system. The immune cells cross the blood brain barrier and attack myelin, leading to ineffective conduction of signals in nervous systems of MS patients. Injections of IFNβ drug several times per week is necessary to control the relapse of MS. The anti-inflammatory mechanism of IFNβ on MS has been reported to involve a shift in cytokine balance from Th1 to Th2 in the T-cell response against elements of the myelin sheath. In addition to the Th1 and Th2 groups, two other important pro-inflammatory cytokines, including osteopontin (OPN), have been found to play important roles in CNS inflammation in the pathogenesis of MS. IFNβ has been shown to inhibit the production of OPN in primary T cells derived from PBMC and the inhibition occurs at the CD4+ T-cell level.

In this study, the biological activity of IFNβ-sFc was evaluated in an osteopontin inhibition assay and its activity was compared to natural IFNβ-1a (Rebif®). Briefly, the osteopontin inhibition assay was carried out as follows:

Human PBMCs were isolated from whole blood. For PBMC stimulation, 96-well flat-bottom tissue culture plate was pre-coated with 100 μl of anti-CD3 antibody at 1 μg/mL concentration per well and incubated overnight at 4° C. Each well was washed with 200 μl RPMI 1640 (with FBS), and seeded with $5 \times 10^4$ cells. Individual wells were treated with either 1 μg/mL anti-CD28 antibody, IFNβ-sFc (1.5 or 10 ng/mL), or Rebif® (1.5 or 10 ng/mL), and the plates were incubated for 48 hours at 37° C. in 5% $CO_2$ humidified incubator. After incubation, the supernatant from each well was harvested and stored in −70° C. freezer. The amount of the human Osteopontin (OPN) was measured by ELISA (R&D systems, CN.: DOST00).

The OPN concentration in each sample was calculated as follows: Separate standard curves were plotted with OPN on the x-axis and absorbance ($OD_{450}$-$OD_{570}$) on the y-axis and a fit line was drawn using a 4-parameter logistic equation. The OPN concentrations were then calculated using the following equation: $X = X0 \times \{[a/(Y-Y0)-1]^{\wedge}(1/b)\}$, as described in Chen M. et al. "Regulatory effects of IFN-β on production of osteopontin and IL-17 by CD4+ T Cells in MS" *Eur. J. Immunol.* 39, 2525-2536 (2009).

Figure 19:
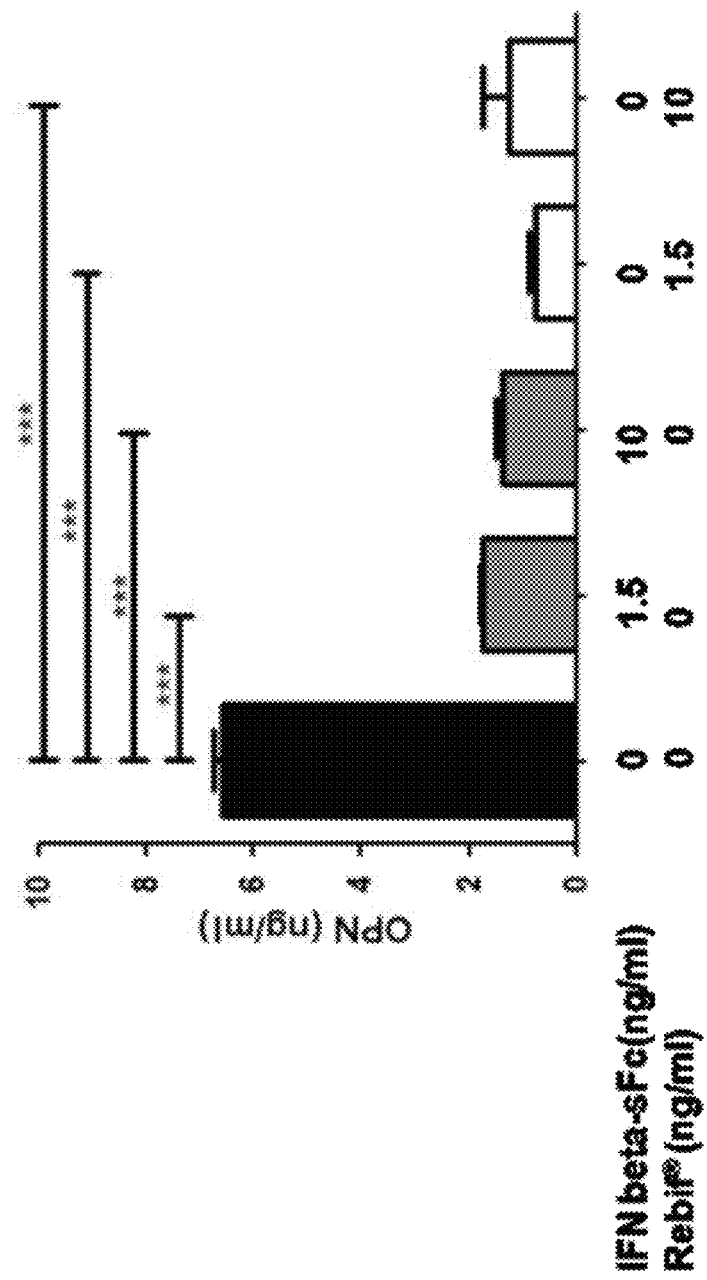
FIG. 19 is a graph showing the osteopontin (OPN) inhibition by IFNβ-sFc fusion protein and Rebif®. The IFNβ-sFc fusion protein exhibited significant inhibition effect of 73.4±0.8% and 79.5±3.6% at both 1.5 ng/mL and 10 ng/mL, respectively. The biological activity of IFNβ-sFc was comparable to Rebif®.

As shown in FIG. 19, the single chain Fc fusion protein of the present disclosure (IFNβ-sFc) significantly inhibited the production of OPN in cells treated with 1.5 ng/mL (73.4±0.8%) and 10 ng/mL (79.5±3.6%) of the test article. Cells treated with the reference article (Rebif®) demonstrated a similar inhibition of OPN at 1.5 ng/mL (88.4±2.7%) and 10 ng/mL (81.3±13.3%). These results suggest that the inclusion of a single chain Fc does not significantly interfere with the ability of the IFNβ portion of the fusion protein to efficiently bind to its receptor since IFNβ-sFc has a comparable biological activity to that of the native IFNβ.

TABLE 1

Examples of Mutated Hinge Regions

| Type of IgG | Sequence | SEQ ID NO |
|---|---|---|
| Wild-type IgG1 | EPKSCDKTHTCPPCP | SEQ ID NO: 1 |
| Mutated IgG1 | EPKSXDKTHTXPPXP | SEQ ID NO: 2 |
|  | EPKSXDKTHTXPP | SEQ ID NO: 3 |
|  | EPKSXDKTHT | SEQ ID NO: 4 |
|  | DKTHTXPPXP | SEQ ID NO: 5 |
| Wild-type IgG2 | ERKCCVECPPCP | SEQ ID NO: 6 |
| Mutated IgG2 | ERKXXVEXPPXP | SEQ ID NO: 7 |
|  | ERKXXVEXPP | SEQ ID NO: 8 |
|  | VEXPPXP | SEQ ID NO: 9 |
| Wild-type IgG3 | ELKTPLGDTTHTCPRCP | SEQ ID NO: 10 |
| Mutated IgG3 | ELKTPLGDTTHTXPRXP | SEQ ID NO: 11 |
|  | ELKTPLGDTTHTXPR | SEQ ID NO: 12 |
|  | ELKTPLGDTTHT | SEQ ID NO: 13 |
| Wild-type IgG3 | EPKSCDTPPPCPRCP | SEQ ID NO: 14 |
| Mutated IgG3 | EPKSXDTPPPXPRXP | SEQ ID NO: 15 |
|  | EPKSXDTPPPXPR | SEQ ID NO: 16 |
|  | EPKSXDTPPP | SEQ ID NO: 17 |
|  | DTPPPXPRXP | SEQ ID NO: 18 |
| Wild-type IgG4 | ESKYGPPCPSCP | SEQ ID NO: 19 |
| Mutated IgG4 | EXKYGPPCPXCP | SEQ ID NO: 20 |
|  | EXKYGPPCP | SEQ ID NO: 21 |
|  | KYGPPCPXCP | SEQ ID NO: 22 |

X: Ser, Gly, Thr, Ala, Val, Leu, Ile, Met, and/or deletion

TABLE 2

Examples of Amino Acid Sequences of Mutated Hinge Regions Derived from IgG1

| Amino acid sequences [1] | SEQ ID NO |
|---|---|
| EPKSSDKTHTSPPSP | SEQ ID NO: 23 |
| EPKSSDKTHTSPP | SEQ ID NO: 24 |
| EPKSSDKTHTSPPP | SEQ ID NO: 25 |
| EPKSSDKTHT | SEQ ID NO: 26 |
| DKTHTSPPSP | SEQ ID NO: 27 |
| DKTHTSPP | SEQ ID NO: 28 |
| EPKSDKTHTPPP | SEQ ID NO: 29 |
| EPKSDKTHTSPPSP | SEQ ID NO: 30 |
| EPKSGDKTHTGPPGP | SEQ ID NO: 31 |
| EPKSGDKTHTGPP | SEQ ID NO: 32 |
| EPKSGDKTHTGPPP | SEQ ID NO: 33 |
| EPKSGDKTHT | SEQ ID NO: 34 |
| DKTHTGPPGP | SEQ ID NO: 35 |
| DKTHTGPP | SEQ ID NO: 36 |
| EPKSDKTHTGPPGP | SEQ ID NO: 37 |
| EPKSGDKTHTSPPSP | SEQ ID NO: 38 |
| EPKSGDKTHTGPPSP | SEQ ID NO: 39 |
| EPKSSDKTHTGPPGP | SEQ ID NO: 40 |
| EPKSSDKTHTGPPSP | SEQ ID NO: 41 |
| EPKSSDKTHTGPP | SEQ ID NO: 42 |
| EPKSGDKTHTSPP | SEQ ID NO: 43 |
| EPKSTDKTHTTPPTP | SEQ ID NO: 44 |
| EPKSTDKTHTTPP | SEQ ID NO: 45 |
| EPKSTDKTHTTPPP | SEQ ID NO: 46 |
| EPKSTDKTHT | SEQ ID NO: 47 |
| DKTHTTPPTP | SEQ ID NO: 48 |
| DKTHTTPP | SEQ ID NO: 49 |
| EPKSDKTHTTPPTP | SEQ ID NO: 50 |
| EPKSSDKTHTTPPTP | SEQ ID NO: 51 |
| EPKSSDKTHTSPPTP | SEQ ID NO: 52 |
| EPKSADKTHTLPPMP | SEQ ID NO: 53 |
| EPKSVDKTHTLPPIP | SEQ ID NO: 54 |
| EPKSLDKTHTAPPAP | SEQ ID NO: 55 |
| EPKSVDKTHTAPP | SEQ ID NO: 56 |
| EPKSMDKTHTVPP | SEQ ID NO: 57 |
| EPKSIDKTHTLPP | SEQ ID NO: 58 |
| DKTHTAPPLP | SEQ ID NO: 59 |
| DKTHTVPPLP | SEQ ID NO: 60 |

[1] Underlined residues represent sites of mutation in relation to the sequence of wild-type IgG.

TABLE 3

Purification of EPO-sFc by Protein A Resin (MabSelect SuRe ™) and DEAE Resin (DEAE FF) Chromatography Columns

| Resin | Sample | Concentration (mg/mL) | Volume (mL) | Amount (mg) | Recovery rate (%) |
|---|---|---|---|---|---|
| MabSelect SuRe ™ | Medium loading | 0.096 | 50 | 4.8 | 65.8 |
|  | pH 3.0 elute | 0.355 | 8.8 | 3.124 |  |
| DEAE FF | EPO-sFc | 0.296 | 20 | 5.92 | 15.48 |
|  | NaCl eluate | 0.067 | 14 | 0.938 |  |

TABLE 4

Purification of FIX-sFc by Protein A Resin (MabSelect SuRe ™) and IXSelect Resin Chromatography Columns

| Resin | Sample | Concentration (mg/mL) | Volume (mL) | Amount (mg) | Recovery rate (%) |
|---|---|---|---|---|---|
| MabSelect SuRe ™ | Medium loading | 0.0188 | 98 | 1.8424 | 88.34 |
| | pH 3.0 elute | 0.217 | 7.5 | 1.6275 | |
| IXSelect | FIX-sFc | 0.0188 | 90 | 1.692 | 20.05 |
| | NaCl eluate | 0.0261 | 13 | 0.3393 | |

TABLE 5

Pharmacokinetic Features of Recombinant EPO (EPREX ®) and EPO-sFc Purified From DEAE FF

| | Recombinant EPO (EPREX ®) | EPO-sFc |
|---|---|---|
| Half-life (hr) | 6.182 ± 0.675 | 22.3 ± 0.38* |
| Cmax (ng/mL) | 6.47 ± 1.07 | 7.2 ± 0.71 |
| Tmax (hr) | 9.33 ± 2.31 | 18 ± 0.00 |
| AUC (0-t) | 161.5 ± 23.64 | 327.4 ± 15.13 |

Values represent means ± S.D. (CV).
*compared with EPREX ®, $P < 0.05$

TABLE 6

Pharmacokinetic Features of Recombinant FIX (BeneFIX ®) and FIX-sFc Purified From MabSelect SuRe ™

| | Recombinant FIX (BeneFIX ®) | FIX-sFc |
|---|---|---|
| Half-life(hr) | 11.91 ± 2.54 | 56.0 ± 13.1 |
| C initial (ng/mL) | 11790.98 ± 4898.85 | 4668.0 ± 447.5 |
| AUC (ng•hr/mL) | 46594.40 ± 3634.08 | 19080.3 ± 2606.4 |

Values represent means ± S.D. (I.V.)

TABLE 7

Potency Comparison Between Recombinant EPO (EPREX ®) and EPO-sFc

| | Recombinant EPO (EPREX ®) | EPO-sFc |
|---|---|---|
| $AUEC_{0-13}$ (ng•hr/mL) | 88.69 | 91.03 |
| $RET_{max}$ | 11.12% | 10.48% |

TABLE 8

Potency Comparison Between Recombinant FIX (BeneFIX ®) and FIX-sFc

| | APTT test (sec) | | | | | | |
|---|---|---|---|---|---|---|---|
| | Recombinant FIX (BeneFIX ®) | | | FIX-sFc | | | |
| Dose | No. 1 | No. 2 | Average | No. 1 | No. 2 | No. 3 | Average |
| 10.0 μg/mL | 25.0 | 25.6 | 25.3 | 23.5 | 26.6 | 26.3 | 25.5 |
| 5.0 μg/mL | 28.1 | 27.0 | 27.6 | 23.5 | 27.6 | 27.6 | 26.2 |
| 2.5 μg/mL | 30.4 | 29.2 | 29.8 | 30.1 | 29.9 | 30.2 | 30.1 |
| Specific activity (IU/mg) | | 200 | | | 218 | | |
| Relative potency [1] | | 1 | | | 1.09 | | |

[1] Relative potency is the ratio of the specific activity of the test sample compared to the specific activity of Recombinant FIX (i.e., 200 IU/mg)

TABLE 9

Pharmacokinetics Features of Interferons in Rats After Subcutaneous Administration

| | Pegasys ® (Pegylated-IFNα) | IFNα-sFc | PEG-Intron ® (Pegylated-IFNα) | Roferon-A ® (recombinant-IFNα) |
|---|---|---|---|---|
| Half-life (Hr) | 23.2 | 50.2 | 20.8 | 0.73 |
| Cmax (pM) | 820.6 | 677.6 | 182.1 | 213.0 |
| Tmax (Hr) | 32.0 | 32.0 | 6.0 | 0.67 |
| AUC (pM/h) | 64694.5 | 60621.9 | 5307.6 | 489.2 |
| CL/kg (mL/h/kg) | 160.8 | 390.7 | 1759.1 | 682.0 |
| Vd/kg (mL/kg) | 4.8 | 5.4 | 58.6 | 638.2 |

TABLE 10

Antiviral Activity of Interferons in Rats After Subcutaneous Administration

| | IFNα-sFc (Monomer) | IFNα-Fc (Dimer) | Pegasys ® (Pegylated-IFNα) |
|---|---|---|---|
| $IC_{50}$ (nM) | 0.0061 | 0.0313 | 0.0894 |
| Ratio [1] | 1 | 0.20 | 0.07 |

[1] The ratio is a comparison of the respective sample $IC_{50}$ with the $IC_{50}$ of IFNα-sFc.

TABLE 11

Binding Affinity Features of IFNα-sFc (Monomer) and IFNα-Fc (Dimer) to IFNAR1

| | Ka (1/Ms) | Kd (1/s) | KD (nM) |
|---|---|---|---|
| IFNα-sFc (Monomer) | 1.4E+06 | 5.6E-03 | 4.0E-09 |
| IFNα-Fc (Dimer) | 3.3E+06 | 5.6E-02 | 1.8E-08 |

TABLE 12

Pharmacokinetics Features of GCSFs in Rats After Subcutaneous Administration

|  | GCSF-sFc | Granocyte ® (Lenograstim) | Neulasta ® (Peg-filgrastim) |
| --- | --- | --- | --- |
| Tmax (hr) | 48 | 0.5 | 10.3 |
| Cmax (ng/mL) | 906.9 | 156.4 | 480.8 |
| Half-life (hr) | 17.16 | 4.1 | 12.0 |
| AUC (ng-h/mL) | 50624 | 790-1292 | 23202 ± 2921 |

TABLE 13

Experimental Setup for Biological Activity Assay for GCSF-sFc

| Group [1] | Sample | Treatment [2] | # Shots | Dose (μM/kg) |
| --- | --- | --- | --- | --- |
| A | Control | 0.9% NaCl/0.1% BSA | 1 | — |
| B1 | Reference | Lenograstim | 1 | 51.02 |
| B2 | Reference | Lenograstim | 1 | 116.07 |
| B2 | Reference | Lenograstim | 4 | 12.75 |
| C1 | Test | GCSF-sFc | 1 | 51.02 |
| C2 | Test | GCSF-sFc | 1 | 116.07 |

[1] Each Group contained 5 neutropenic mice
[2] All Groups were pre-treated with CPA (Cyclophosphamide monohydrate) on Day 0. Administration of the treatment drug was given on Day 1 for the Groups that received a single shot, and on Days 1, 2, 3, and 4 for the Group that received 4 shots.

TABLE 14

Recovery Rate of IFNβ-sFc Purified with Protein A Resin, Determined by ELISA

|  | Concentration (mg/mL) | Volume (mL) | Amount (mg) | Recovery (%) |
| --- | --- | --- | --- | --- |
| Medium loading | 0.01 | 925.0 | 8.33 | — |
| Eluate | 0.25 | 25.0 | 6.34 | 76.13 |

TABLE 15

Pharmacokinetics Features of IFNβ in Rats After Subcutaneous Administration

|  | Rebif ® (Natural IFNβ) | IFNβ-sFc |
| --- | --- | --- |
| $T_{1/2}$ (hr) | 18.92-23.57 | 31.89-37.70 |
| $T_{max}$ (hr) | 12.00 ± 0 | 9.55 ± 3.61 |
| $C_{max}$ (ng/mL) | 3.20 ± 0.71 | 6.55 ± 0.78 |
| AUC (ng-hr/mL) | 115 ± 18.38 | 273 ± 2.83 |
| Clearance (mL/hr/kg) | 326 ± 53.74 | 136 ± 1.41 |

The invention claimed is:

1. A fusion protein consisting of
   a) a single chain Fc (sFc) fragment of an IgG molecule having an amino acid sequence selected from the group consisting of SEQ ID NOs: 61, 62, 63, and 64;
   b) a bioactive molecule having an amino acid sequence of SEQ ID NO: 65; and
   c) a hinge region between the sFc fragment and the bioactive molecule comprising an amino acid sequence selected from the group consisting of SEQ ID NOs : 23-60.

2. A pharmaceutical composition comprising the fusion protein according to claim 1 and a pharmaceutically acceptable carrier or excipient.

3. The fusion protein according to claim 1, wherein the amino acid sequence of the hinge region is SEQ ID NO: 23 or 27.

4. The fusion protein according to claim 1, wherein the amino acid sequence of the fusion protein is SEQ ID NO: 66.

* * * * *

```
                              SEQUENCE LISTING

<160> NUMBER OF SEQ ID NOS: 74

<210> SEQ ID NO 1
    <211> LENGTH: 15
    <212> TYPE: PRT
    <213> ORGANISM: Homo sapiens
    <220> FEATURE:
    <221> NAME/KEY: SITE
    <222> LOCATION: (1)..(15)
    <223> OTHER INFORMATION: wild type IgG1 hinge peptide sequence

<400> SEQUENCE: 1

Glu Pro Lys Ser Cys Asp Lys Thr His Thr Cys Pro Pro Cys Pro
    1               5                   10                  15

<210> SEQ ID NO 2
    <211> LENGTH: 15
    <212> TYPE: PRT
    <213> ORGANISM: Artificial Sequence
    <220> FEATURE:
    <223> OTHER INFORMATION: Mutated IgG1 Hinge Region
    <220> FEATURE:
    <221> NAME/KEY: SITE
    <222> LOCATION: (1)..(15)
    <223> OTHER INFORMATION: Artificial mutated IgG1 hinge peptide sequence
    <220> FEATURE:
    <221> NAME/KEY: SITE
    <222> LOCATION: (5)..(5)
    <223> OTHER INFORMATION: S or G or T or A or V or L or I or M or
          deletion
    <220> FEATURE:
    <221> NAME/KEY: SITE
    <222> LOCATION: (11)..(11)
    <223> OTHER INFORMATION: S or G or T or A or V or L or I or M or
          deletion
    <220> FEATURE:
    <221> NAME/KEY: SITE
    <222> LOCATION: (14)..(14)
    <223> OTHER INFORMATION: S or G or T or A or V or L or I or M or
          deletion

<400> SEQUENCE: 2
```

Glu Pro Lys Ser Xaa Asp Lys Thr His Thr Xaa Pro Pro Xaa Pro
1               5                   10                  15

<210> SEQ ID NO 3
<211> LENGTH: 13
<212> TYPE: PRT
<213> ORGANISM: Artificial Sequence
<220> FEATURE:
<223> OTHER INFORMATION: Mutated IgG1 Hinge Region
<220> FEATURE:
<221> NAME/KEY: SITE
<222> LOCATION: (1)..(13)
<223> OTHER INFORMATION: Artificial mutated IgG1 hinge peptide sequence
<220> FEATURE:
<221> NAME/KEY: SITE
<222> LOCATION: (5)..(5)
<223> OTHER INFORMATION: S or G or T or A or V or L or I or M or
      deletion
<220> FEATURE:
<221> NAME/KEY: SITE
<222> LOCATION: (11)..(11)
<223> OTHER INFORMATION: S or G or T or A or V or L or I or M or
      deletion

<400> SEQUENCE: 3

Glu Pro Lys Ser Xaa Asp Lys Thr His Thr Xaa Pro Pro
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Mutated IgG1 Hinge Region
<220> FEATURE:
<221> NAME/KEY: SITE
<222> LOCATION: (1)..(10)
<223> OTHER INFORMATION: Artificial mutated IgG1 hinge peptide sequence
<220> FEATURE:
<221> NAME/KEY: SITE
<222> LOCATION: (5)..(5)
<223> OTHER INFORMATION: S or G or T or A or V or L or I or M or
      deletion

<400> SEQUENCE: 4

Glu Pro Lys Ser Xaa Asp Lys Thr His Thr
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Mutated IgG1 Hinge Region
<220> FEATURE:
<221> NAME/KEY: SITE
<222> LOCATION: (1)..(10)
<223> OTHER INFORMATION: Artificial mutated IgG1 hinge peptide sequence
<220> FEATURE:
<221> NAME/KEY: SITE
<222> LOCATION: (6)..(6)
<223> OTHER INFORMATION: S or G or T or A or V or L or I or M or
      deletion
<220> FEATURE:
<221> NAME/KEY: SITE
<222> LOCATION: (9)..(9)
<223> OTHER INFORMATION: S or G or T or A or V or L or I or M or
      deletion

<400> SEQUENCE: 5

Asp Lys Thr His Thr Xaa Pro Pro Xaa Pro
1               5                   10

```
<210> SEQ ID NO 6
<211> LENGTH: 12
<212> TYPE: PRT
<213> ORGANISM: Homo sapiens
<220> FEATURE:
<221> NAME/KEY: SITE
<222> LOCATION: (1)..(12)
<223> OTHER INFORMATION: Wild type IgG2 hinge peptide sequence

<400> SEQUENCE: 6

Glu Arg Lys Cys Cys Val Glu Cys Pro Pro Cys Pro
1               5                   10

<210> SEQ ID NO 7
<211> LENGTH: 12
<212> TYPE: PRT
<213> ORGANISM: Artificial Sequence
<220> FEATURE:
<223> OTHER INFORMATION: Mutated IgG2 Hinge Region
<220> FEATURE:
<221> NAME/KEY: SITE
<222> LOCATION: (1)..(12)
<223> OTHER INFORMATION: Artificial mutated IgG2 hinge peptide sequence
<220> FEATURE:
<221> NAME/KEY: SITE
<222> LOCATION: (4)..(4)
<223> OTHER INFORMATION: S or G or T or A or V or L or I or M or
      deletion
<220> FEATURE:
<221> NAME/KEY: SITE
<222> LOCATION: (5)..(5)
<223> OTHER INFORMATION: S or G or T or A or V or L or I or M or
      deletion
<220> FEATURE:
<221> NAME/KEY: SITE
<222> LOCATION: (8)..(8)
<223> OTHER INFORMATION: S or G or T or A or V or L or I or M or
      deletion
<220> FEATURE:
<221> NAME/KEY: SITE
<222> LOCATION: (11)..(11)
<223> OTHER INFORMATION: S or G or T or A or V or L or I or M or
      deletion

<400> SEQUENCE: 7

Glu Arg Lys Xaa Xaa Val Glu Xaa Pro Pro Xaa Pro
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Mutated IgG2 Hinge Region
<220> FEATURE:
<221> NAME/KEY: SITE
<222> LOCATION: (1)..(10)
<223> OTHER INFORMATION: Artificial mutated IgG2 hinge peptide sequence
<220> FEATURE:
<221> NAME/KEY: SITE
<222> LOCATION: (4)..(4)
<223> OTHER INFORMATION: S or G or T or A or V or L or I or M or
      deletion
<220> FEATURE:
<221> NAME/KEY: SITE
<222> LOCATION: (5)..(5)
<223> OTHER INFORMATION: S or G or T or A or V or L or I or M or
      deletion
<220> FEATURE:
<221> NAME/KEY: SITE
<222> LOCATION: (8)..(8)
<223> OTHER INFORMATION: S or G or T or A or V or L or I or M or
      deletion
```

```
<400> SEQUENCE: 8

Glu Arg Lys Xaa Xaa Val Glu Xaa Pro Pro
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Mutated IgG2 Hinge Region
<220> FEATURE:
<221> NAME/KEY: SITE
<222> LOCATION: (1)..(7)
<223> OTHER INFORMATION: Artificial mutated IgG2 hinge peptide sequence
<220> FEATURE:
<221> NAME/KEY: SITE
<222> LOCATION: (3)..(3)
<223> OTHER INFORMATION: S or G or T or A or V or L or I or M or
      deletion
<220> FEATURE:
<221> NAME/KEY: SITE
<222> LOCATION: (6)..(6)
<223> OTHER INFORMATION: S or G or T or A or V or L or I or M or
      deletion

<400> SEQUENCE: 9

Val Glu Xaa Pro Pro Xaa Pro
1               5

<210> SEQ ID NO 10
<211> LENGTH: 17
<212> TYPE: PRT
<213> ORGANISM: Homo sapiens
<220> FEATURE:
<221> NAME/KEY: SITE
<222> LOCATION: (1)..(17)
<223> OTHER INFORMATION: Wild type IgG3 hinge peptide sequence

<400> SEQUENCE: 10

Glu Leu Lys Thr Pro Leu Gly Asp Thr Thr His Thr Cys Pro Arg Cys
1               5                   10                  15

Pro

<210> SEQ ID NO 11
<211> LENGTH: 17
<212> TYPE: PRT
<213> ORGANISM: Artificial Sequence
<220> FEATURE:
<223> OTHER INFORMATION: Mutated IgG3 Hinge Region
<220> FEATURE:
<221> NAME/KEY: SITE
<222> LOCATION: (1)..(17)
<223> OTHER INFORMATION: Artificial mutated IgG3 hinge peptide sequence
<220> FEATURE:
<221> NAME/KEY: SITE
<222> LOCATION: (13)..(13)
<223> OTHER INFORMATION: S or G or T or A or V or L or I or M or
      deletion
<220> FEATURE:
<221> NAME/KEY: SITE
<222> LOCATION: (16)..(16)
<223> OTHER INFORMATION: S or G or T or A or V or L or I or M or
      deletion

<400> SEQUENCE: 11

Glu Leu Lys Thr Pro Leu Gly Asp Thr Thr His Thr Xaa Pro Arg Xaa
1               5                   10                  15

Pro
```

```
<210> SEQ ID NO 12
<211> LENGTH: 15
<212> TYPE: PRT
<213> ORGANISM: Artificial Sequence
<220> FEATURE:
<223> OTHER INFORMATION: Mutated IgG3 Hinge Region
<220> FEATURE:
<221> NAME/KEY: SITE
<222> LOCATION: (1)..(15)
<223> OTHER INFORMATION: Artificial mutated IgG3 hinge peptide sequence
<220> FEATURE:
<221> NAME/KEY: SITE
<222> LOCATION: (13)..(13)
<223> OTHER INFORMATION: S or G or T or A or V or L or I or M or
      deletion

<400> SEQUENCE: 12

Glu Leu Lys Thr Pro Leu Gly Asp Thr Thr His Thr Xaa Pro Arg
1               5                   10                  15

<210> SEQ ID NO 13
<211> LENGTH: 12
<212> TYPE: PRT
<213> ORGANISM: Artificial Sequence
<220> FEATURE:
<223> OTHER INFORMATION: Mutated IgG3 Hinge Region
<220> FEATURE:
<221> NAME/KEY: SITE
<222> LOCATION: (1)..(12)
<223> OTHER INFORMATION: Artificial mutated IgG3 hinge peptide sequence

<400> SEQUENCE: 13

Glu Leu Lys Thr Pro Leu Gly Asp Thr Thr His Thr
1               5                   10

<210> SEQ ID NO 14
<211> LENGTH: 15
<212> TYPE: PRT
<213> ORGANISM: Homo sapiens
<220> FEATURE:
<221> NAME/KEY: SITE
<222> LOCATION: (1)..(15)
<223> OTHER INFORMATION: Wild type IgG3 hinge peptide sequence

<400> SEQUENCE: 14

Glu Pro Lys Ser Cys Asp Thr Pro Pro Pro Cys Pro Arg Cys Pro
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Mutated IgG3 Hinge Region
<220> FEATURE:
<221> NAME/KEY: SITE
<222> LOCATION: (1)..(15)
<223> OTHER INFORMATION: Artificial mutated IgG3 hinge peptide sequence
<220> FEATURE:
<221> NAME/KEY: SITE
<222> LOCATION: (5)..(5)
<223> OTHER INFORMATION: S or G or T or A or V or L or I or M or
      deletion
<220> FEATURE:
<221> NAME/KEY: SITE
<222> LOCATION: (11)..(11)
<223> OTHER INFORMATION: S or G or T or A or V or L or I or M or
      deletion
<220> FEATURE:
<221> NAME/KEY: SITE
<222> LOCATION: (14)..(14)
<223> OTHER INFORMATION: S or G or T or A or V or L or I or M or
```

```
                              deletion

<400> SEQUENCE: 15

Glu Pro Lys Ser Xaa Asp Thr Pro Pro Pro Xaa Pro Arg Xaa Pro
1               5                   10                  15

<210> SEQ ID NO 16
<211> LENGTH: 13
<212> TYPE: PRT
<213> ORGANISM: Artificial Sequence
<220> FEATURE:
<223> OTHER INFORMATION: Mutated IgG3 Hinge Region
<220> FEATURE:
<221> NAME/KEY: SITE
<222> LOCATION: (1)..(13)
<223> OTHER INFORMATION: Artificial mutated IgG3 hinge peptide sequence
<220> FEATURE:
<221> NAME/KEY: SITE
<222> LOCATION: (5)..(5)
<223> OTHER INFORMATION: S or G or T or A or V or L or I or M or
      deletion
<220> FEATURE:
<221> NAME/KEY: SITE
<222> LOCATION: (11)..(11)
<223> OTHER INFORMATION: S or G or T or A or V or L or I or M or
      deletion

<400> SEQUENCE: 16

Glu Pro Lys Ser Xaa Asp Thr Pro Pro Pro Xaa Pro Arg
1               5                   10

<210> SEQ ID NO 17
<211> LENGTH: 10
<212> TYPE: PRT
<213> ORGANISM: Artificial Sequence
<220> FEATURE:
<223> OTHER INFORMATION: Mutated IgG3 Hinge Region
<220> FEATURE:
<221> NAME/KEY: SITE
<222> LOCATION: (1)..(10)
<223> OTHER INFORMATION: Artificial mutated IgG3 hinge peptide sequence
<220> FEATURE:
<221> NAME/KEY: SITE
<222> LOCATION: (5)..(5)
<223> OTHER INFORMATION: S or G or T or A or V or L or I or M or
      deletion

<400> SEQUENCE: 17

Glu Pro Lys Ser Xaa Asp Thr Pro Pro Pro
1               5                   10

<210> SEQ ID NO 18
<211> LENGTH: 10
<212> TYPE: PRT
<213> ORGANISM: Artificial Sequence
<220> FEATURE:
<223> OTHER INFORMATION: Mutated IgG3 Hinge Region
<220> FEATURE:
<221> NAME/KEY: SITE
<222> LOCATION: (1)..(10)
<223> OTHER INFORMATION: Artificial mutated IgG3 hinge peptide sequence
<220> FEATURE:
<221> NAME/KEY: SITE
<222> LOCATION: (6)..(6)
<223> OTHER INFORMATION: S or G or T or A or V or L or I or M or
      deletion
<220> FEATURE:
<221> NAME/KEY: SITE
<222> LOCATION: (9)..(9)
<223> OTHER INFORMATION: S or G or T or A or V or L or I or M or
      deletion

<400> SEQUENCE: 18
```

```
Asp Thr Pro Pro Xaa Pro Arg Xaa Pro
1               5                   10

<210> SEQ ID NO 19
<211> LENGTH: 12
<212> TYPE: PRT
<213> ORGANISM: Homo sapiens
<220> FEATURE:
<221> NAME/KEY: SITE
<222> LOCATION: (1)..(12)
<223> OTHER INFORMATION: Wild type IgG4 hinge peptide sequence

<400> SEQUENCE: 19

Glu Ser Lys Tyr Gly Pro Pro Cys Pro Ser Cys Pro
1               5                   10

<210> SEQ ID NO 20
<211> LENGTH: 12
<212> TYPE: PRT
<213> ORGANISM: Artificial Sequence
<220> FEATURE:
<223> OTHER INFORMATION: Mutated IgG4 Hinge Region
<220> FEATURE:
<221> NAME/KEY: SITE
<222> LOCATION: (1)..(12)
<223> OTHER INFORMATION: Artificial mutated IgG4 hinge peptide sequence
<220> FEATURE:
<221> NAME/KEY: SITE
<222> LOCATION: (10)..(10)
<223> OTHER INFORMATION: S or G or T or A or V or L or I or M or
      deletion

<400> SEQUENCE: 20

Glu Xaa Lys Tyr Gly Pro Pro Cys Pro Xaa Cys Pro
1               5                   10

<210> SEQ ID NO 21
<211> LENGTH: 9
<212> TYPE: PRT
<213> ORGANISM: Artificial Sequence
<220> FEATURE:
<223> OTHER INFORMATION: Mutated IgG4 Hinge Region
<220> FEATURE:
<221> NAME/KEY: SITE
<222> LOCATION: (1)..(9)
<223> OTHER INFORMATION: Artificial mutated IgG4 hinge peptide sequence
<220> FEATURE:
<221> NAME/KEY: SITE
<222> LOCATION: (2)..(2)
<223> OTHER INFORMATION: S or G or T or A or V or L or I or M or
      deletion

<400> SEQUENCE: 21

Glu Xaa Lys Tyr Gly Pro Pro Cys Pro
1               5

<210> SEQ ID NO 22
<211> LENGTH: 10
<212> TYPE: PRT
<213> ORGANISM: Artificial Sequence
<220> FEATURE:
<223> OTHER INFORMATION: Mutated IgG4 Hinge Region
<220> FEATURE:
<221> NAME/KEY: SITE
<222> LOCATION: (1)..(10)
<223> OTHER INFORMATION: Artificial mutated IgG4 hinge peptide sequence
<220> FEATURE:
<221> NAME/KEY: SITE
<222> LOCATION: (8)..(8)
<223> OTHER INFORMATION: S or G or T or A or V or L or I or M or
      deletion
```

```
<400> SEQUENCE: 22

Lys Tyr Gly Pro Pro Cys Pro Xaa Cys Pro
1               5                   10

<210> SEQ ID NO 23
<211> LENGTH: 15
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(15)
<223> OTHER INFORMATION: Artificial IgG1 hinge peptide sequence

<400> SEQUENCE: 23

Glu Pro Lys Ser Ser Asp Lys Thr His Thr Ser Pro Pro Ser Pro
1               5                   10                  15

<210> SEQ ID NO 24
<211> LENGTH: 13
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(13)
<223> OTHER INFORMATION: Artificial IgG1 hinge peptide sequence

<400> SEQUENCE: 24

Glu Pro Lys Ser Ser Asp Lys Thr His Thr Ser Pro Pro
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(14)
<223> OTHER INFORMATION: Artificial IgG1 hinge peptide sequence

<400> SEQUENCE: 25

Glu Pro Lys Ser Ser Asp Lys Thr His Thr Ser Pro Pro Pro
1               5                   10

<210> SEQ ID NO 26
<211> LENGTH: 10
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(10)
<223> OTHER INFORMATION: Artificial IgG1 hinge peptide sequence

<400> SEQUENCE: 26

Glu Pro Lys Ser Ser Asp Lys Thr His Thr
1               5                   10

<210> SEQ ID NO 27
<211> LENGTH: 10
<212> TYPE: PRT
<213> ORGANISM: Artificial Sequence
```

```
<220> FEATURE:
<223> OTHER INFORMATION: Mutated IgG Hinge Region
<220> FEATURE:
<221> NAME/KEY: SITE
<222> LOCATION: (1)..(10)
<223> OTHER INFORMATION: Artificial IgG1 hinge peptide sequence

<400> SEQUENCE: 27

Asp Lys Thr His Thr Ser Pro Pro Ser Pro
1               5                   10

<210> SEQ ID NO 28
<211> LENGTH: 8
<212> TYPE: PRT
<213> ORGANISM: Homo sapiens
<220> FEATURE:
<221> NAME/KEY: SITE
<222> LOCATION: (1)..(8)
<223> OTHER INFORMATION: Artificial IgG1 hinge peptide sequence

<400> SEQUENCE: 28

Asp Lys Thr His Thr Ser Pro Pro
1               5

<210> SEQ ID NO 29
<211> LENGTH: 12
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(12)
<223> OTHER INFORMATION: Artificial IgG1 hinge peptide sequence

<400> SEQUENCE: 29

Glu Pro Lys Ser Asp Lys Thr His Thr Pro Pro Pro
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(14)
<223> OTHER INFORMATION: Artificial IgG1 hinge peptide sequence

<400> SEQUENCE: 30

Glu Pro Lys Ser Asp Lys Thr His Thr Ser Pro Pro Ser Pro
1               5                   10

<210> SEQ ID NO 31
<211> LENGTH: 15
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(15)
<223> OTHER INFORMATION: Artificial IgG1 hinge peptide sequence

<400> SEQUENCE: 31

Glu Pro Lys Ser Gly Asp Lys Thr His Thr Gly Pro Pro Gly Pro
1               5                   10                  15
```

```
<210> SEQ ID NO 32
<211> LENGTH: 13
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(13)
<223> OTHER INFORMATION: Artificial IgG1 hinge peptide sequence

<400> SEQUENCE: 32

Glu Pro Lys Ser Gly Asp Lys Thr His Thr Gly Pro Pro
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(14)
<223> OTHER INFORMATION: Artificial IgG1 hinge peptide sequence

<400> SEQUENCE: 33

Glu Pro Lys Ser Gly Asp Lys Thr His Thr Gly Pro Pro Pro
1               5                   10

<210> SEQ ID NO 34
<211> LENGTH: 10
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(10)
<223> OTHER INFORMATION: Artificial IgG1 hinge peptide sequence

<400> SEQUENCE: 34

Glu Pro Lys Ser Gly Asp Lys Thr His Thr
1               5                   10

<210> SEQ ID NO 35
<211> LENGTH: 10
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(10)
<223> OTHER INFORMATION: Artificial IgG1 hinge peptide sequence

<400> SEQUENCE: 35

Asp Lys Thr His Thr Gly Pro Pro Gly Pro
1               5                   10

<210> SEQ ID NO 36
<211> LENGTH: 8
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(8)
<223> OTHER INFORMATION: Artificial IgG1 hinge peptide sequence
```

```
<400> SEQUENCE: 36

Asp Lys Thr His Thr Gly Pro Pro
1               5

<210> SEQ ID NO 37
<211> LENGTH: 14
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(14)
<223> OTHER INFORMATION: Artificial IgG1 hinge peptide sequence

<400> SEQUENCE: 37

Glu Pro Lys Ser Asp Lys Thr His Thr Gly Pro Pro Gly Pro
1               5                   10

<210> SEQ ID NO 38
<211> LENGTH: 15
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(15)
<223> OTHER INFORMATION: Artificial IgG1 hinge peptide sequence

<400> SEQUENCE: 38

Glu Pro Lys Ser Gly Asp Lys Thr His Thr Ser Pro Pro Ser Pro
1               5                   10                  15

<210> SEQ ID NO 39
<211> LENGTH: 15
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(15)
<223> OTHER INFORMATION: Artificial IgG1 hinge peptide sequence

<400> SEQUENCE: 39

Glu Pro Lys Ser Gly Asp Lys Thr His Thr Gly Pro Pro Ser Pro
1               5                   10                  15

<210> SEQ ID NO 40
<211> LENGTH: 15
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(15)
<223> OTHER INFORMATION: Artificial IgG1 hinge peptide sequence

<400> SEQUENCE: 40

Glu Pro Lys Ser Ser Asp Lys Thr His Thr Gly Pro Pro Gly Pro
1               5                   10                  15

<210> SEQ ID NO 41
<211> LENGTH: 15
<212> TYPE: PRT
<213> ORGANISM: Artificial Sequence
<220> FEATURE:
```

<223> OTHER INFORMATION: Mutated IgG Hinge Region
<220> FEATURE:
<221> NAME/KEY: SITE
<222> LOCATION: (1)..(15)
<223> OTHER INFORMATION: Artificial IgG1 hinge peptide sequence

<400> SEQUENCE: 41

Glu Pro Lys Ser Ser Asp Lys Thr His Thr Gly Pro Pro Ser Pro
1               5                   10                  15

<210> SEQ ID NO 42
<211> LENGTH: 13
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(13)
<223> OTHER INFORMATION: Artificial IgG1 hinge peptide sequence

<400> SEQUENCE: 42

Glu Pro Lys Ser Ser Asp Lys Thr His Thr Gly Pro Pro
1               5                   10

<210> SEQ ID NO 43
<211> LENGTH: 13
<212> TYPE: PRT
<213> ORGANISM: Homo sapiens
<220> FEATURE:
<221> NAME/KEY: SITE
<222> LOCATION: (1)..(13)
<223> OTHER INFORMATION: Artificial IgG1 hinge peptide sequence

<400> SEQUENCE: 43

Glu Pro Lys Ser Gly Asp Lys Thr His Thr Ser Pro Pro
1               5                   10

<210> SEQ ID NO 44
<211> LENGTH: 15
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(15)
<223> OTHER INFORMATION: Artificial IgG1 hinge peptide sequence

<400> SEQUENCE: 44

Glu Pro Lys Ser Thr Asp Lys Thr His Thr Thr Pro Pro Thr Pro
1               5                   10                  15

<210> SEQ ID NO 45
<211> LENGTH: 13
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(13)
<223> OTHER INFORMATION: Artificial IgG1 hinge peptide sequence

<400> SEQUENCE: 45

Glu Pro Lys Ser Thr Asp Lys Thr His Thr Thr Pro Pro
1               5                   10

<210> SEQ ID NO 46

```
<211> LENGTH: 14
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(14)
<223> OTHER INFORMATION: Artificial IgG1 hinge peptide sequence

<400> SEQUENCE: 46

Glu Pro Lys Ser Thr Asp Lys Thr His Thr Thr Pro Pro Pro
1               5                   10

<210> SEQ ID NO 47
<211> LENGTH: 10
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(10)
<223> OTHER INFORMATION: Artificial IgG1 hinge peptide sequence

<400> SEQUENCE: 47

Glu Pro Lys Ser Thr Asp Lys Thr His Thr
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(10)
<223> OTHER INFORMATION: Artificial IgG1 hinge peptide sequence

<400> SEQUENCE: 48

Asp Lys Thr His Thr Thr Pro Pro Thr Pro
1               5                   10

<210> SEQ ID NO 49
<211> LENGTH: 8
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(8)
<223> OTHER INFORMATION: Artificial IgG1 hinge peptide sequence

<400> SEQUENCE: 49

Asp Lys Thr His Thr Thr Pro Pro
1               5

<210> SEQ ID NO 50
<211> LENGTH: 14
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(14)
<223> OTHER INFORMATION: Artificial IgG1 hinge peptide sequence

<400> SEQUENCE: 50
```

```
Glu Pro Lys Ser Asp Lys Thr His Thr Pro Pro Thr Pro
1               5                   10

<210> SEQ ID NO 51
<211> LENGTH: 15
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(15)
<223> OTHER INFORMATION: Artificial IgG1 hinge peptide sequence

<400> SEQUENCE: 51

Glu Pro Lys Ser Ser Asp Lys Thr His Thr Thr Pro Pro Thr Pro
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(15)
<223> OTHER INFORMATION: Artificial IgG1 hinge peptide sequence

<400> SEQUENCE: 52

Glu Pro Lys Ser Ser Asp Lys Thr His Thr Ser Pro Pro Thr Pro
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(15)
<223> OTHER INFORMATION: Artificial IgG1 hinge peptide sequence

<400> SEQUENCE: 53

Glu Pro Lys Ser Ala Asp Lys Thr His Thr Leu Pro Pro Met Pro
1               5                   10                  15

<210> SEQ ID NO 54
<211> LENGTH: 15
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(15)
<223> OTHER INFORMATION: Artificial IgG1 hinge peptide sequence

<400> SEQUENCE: 54

Glu Pro Lys Ser Val Asp Lys Thr His Thr Leu Pro Pro Ile Pro
1               5                   10                  15

<210> SEQ ID NO 55
<211> LENGTH: 15
<212> TYPE: PRT
<213> ORGANISM: Artificial Sequence
<220> FEATURE:
<223> OTHER INFORMATION: Mutated IgG Hinge Region
```

```
<220> FEATURE:
<221> NAME/KEY: SITE
<222> LOCATION: (1)..(15)
<223> OTHER INFORMATION: Artificial IgG1 hinge peptide sequence

<400> SEQUENCE: 55

Glu Pro Lys Ser Leu Asp Lys Thr His Thr Ala Pro Pro Ala Pro
1               5                   10                  15

<210> SEQ ID NO 56
<211> LENGTH: 13
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(13)
<223> OTHER INFORMATION: Artificial IgG1 hinge peptide sequence

<400> SEQUENCE: 56

Glu Pro Lys Ser Val Asp Lys Thr His Thr Ala Pro Pro
1               5                   10

<210> SEQ ID NO 57
<211> LENGTH: 13
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(13)
<223> OTHER INFORMATION: Artificial IgG1 hinge peptide sequence

<400> SEQUENCE: 57

Glu Pro Lys Ser Met Asp Lys Thr His Thr Val Pro Pro
1               5                   10

<210> SEQ ID NO 58
<211> LENGTH: 13
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(13)
<223> OTHER INFORMATION: Artificial IgG1 hinge peptide sequence

<400> SEQUENCE: 58

Glu Pro Lys Ser Ile Asp Lys Thr His Thr Leu Pro Pro
1               5                   10

<210> SEQ ID NO 59
<211> LENGTH: 10
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(10)
<223> OTHER INFORMATION: Artificial IgG1 hinge peptide sequence

<400> SEQUENCE: 59

Asp Lys Thr His Thr Ala Pro Pro Leu Pro
1               5                   10
```

```
<210> SEQ ID NO 60
<211> LENGTH: 10
<212> TYPE: PRT
<213> ORGANISM: Artificial Sequence
<220> FEATURE:
<223> OTHER INFORMATION: Mutated IgG Hinge Region
<220> FEATURE:
<221> NAME/KEY: SITE
<222> LOCATION: (1)..(10)
<223> OTHER INFORMATION: Artificial IgG1 hinge peptide sequence

<400> SEQUENCE: 60

Asp Lys Thr His Thr Val Pro Pro Leu Pro
1               5                   10

<210> SEQ ID NO 61
<211> LENGTH: 216
<212> TYPE: PRT
<213> ORGANISM: Homo sapiens
<220> FEATURE:
<221> NAME/KEY: SITE
<222> LOCATION: (1)..(216)
<223> OTHER INFORMATION: Fc region of wild type IgG1 (CH2-CH3 domain of
      human IgG1)

<400> SEQUENCE: 61

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
    50                  55                  60

Gln Tyr Asn Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 62
<211> LENGTH: 216
<212> TYPE: PRT
<213> ORGANISM: Artificial Sequence
<220> FEATURE:
<223> OTHER INFORMATION: Fc region of human IgG1 with glycosylation site
      mutated from Asn to His
```

```
<220> FEATURE:
<221> NAME/KEY: SITE
<222> LOCATION: (67)..(67)
<223> OTHER INFORMATION: Glycosylation site at residue 67 in wild type
      sequence mutated to His

<400> SEQUENCE: 62

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr His Ser Thr Tyr Arg Val Val Ser Val Leu Thr Val Leu His
65                  70                  75                  80

Gln Asp Trp Leu Asn Gly Lys Glu Tyr Lys Cys Lys Val Ser Asn Lys
                85                  90                  95

Ala Leu Pro Ala Pro Ile Glu Lys Thr Ile Ser Lys Ala Lys Gly Gln
            100                 105                 110

Pro Arg Glu Pro Gln Val Tyr Thr Leu Pro Pro Ser Arg Asp Glu Leu
        115                 120                 125

Thr Lys Asn Gln Val Ser Leu Thr Cys Leu Val Lys Gly Phe Tyr Pro
    130                 135                 140

Ser Asp Ile Ala Val Glu Trp Glu Ser Asn Gly Gln Pro Glu Asn Asn
145                 150                 155                 160

Tyr Lys Thr Thr Pro Pro Val Leu Asp Ser Asp Gly Ser Phe Phe Leu
                165                 170                 175

Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 63
<211> LENGTH: 216
<212> TYPE: PRT
<213> ORGANISM: Artificial Sequence
<220> FEATURE:
<223> OTHER INFORMATION: Fc region of human IgG1 with glycosylation site
      mutated from Asn to Ala
<220> FEATURE:
<221> NAME/KEY: SITE
<222> LOCATION: (67)..(67)
<223> OTHER INFORMATION: Glycosylation site at residue 67 in wild type
      sequence mutated to Ala

<400> SEQUENCE: 63

Ala Pro Glu Leu Leu Gly Gly Pro Ser Val Phe Leu Phe Pro Pro Lys
1               5                   10                  15

Pro Lys Asp Thr Leu Met Ile Ser Arg Thr Pro Glu Val Thr Cys Val
            20                  25                  30

Val Val Asp Val Ser His Glu Asp Pro Glu Val Lys Phe Asn Trp Tyr
        35                  40                  45

Val Asp Gly Val Glu Val His Asn Ala Lys Thr Lys Pro Arg Glu Glu
50                  55                  60

Gln Tyr Ala Ser Thr Tyr Arg Val Val Ser Val Leu Thr Val Leu His
```

```
                        65                   70                  75                  80
        Gln Asp Trp Leu Asn Gly Lys Glu Tyr Lys Cys Lys Val Ser Asn Lys
                            85                  90                  95

Ala Leu Pro Ala Pro Ile Glu Lys Thr Ile Ser Lys Ala Lys Gly Gln
                        100                 105                 110

Pro Arg Glu Pro Gln Val Tyr Thr Leu Pro Pro Ser Arg Asp Glu Leu
                        115                 120                 125

Thr Lys Asn Gln Val Ser Leu Thr Cys Leu Val Lys Gly Phe Tyr Pro
                    130                 135                 140

Ser Asp Ile Ala Val Glu Trp Glu Ser Asn Gly Gln Pro Glu Asn Asn
        145                 150                 155                 160

Tyr Lys Thr Thr Pro Pro Val Leu Asp Ser Asp Gly Ser Phe Phe Leu
                        165                 170                 175

Tyr Ser Lys Leu Thr Val Asp Lys Ser Arg Trp Gln Gln Gly Asn Val
                        180                 185                 190

Phe Ser Cys Ser Val Met His Glu Ala Leu His Asn His Tyr Thr Gln
                    195                 200                 205

Lys Ser Leu Ser Leu Ser Pro Gly
                    210                 215

<210> SEQ ID NO 64
<211> LENGTH: 216
<212> TYPE: PRT
<213> ORGANISM: Artificial Sequence
<220> FEATURE:
<223> OTHER INFORMATION: Fc region of human IgG1 with variable residues
      at the wild type glycosylation site
<220> FEATURE:
<221> NAME/KEY: SITE
<222> LOCATION: (67)..(67)
<223> OTHER INFORMATION: N or H or A
<220> FEATURE:
<221> NAME/KEY: SITE
<222> LOCATION: (67)..(67)
<223> OTHER INFORMATION: Glycosylation site in wild-type IgG1

<400> SEQUENCE: 64

Ala Pro Glu Leu Leu Gly Gly Pro Ser Val Phe Leu Phe Pro Pro Lys
        1               5                   10                  15

Pro Lys Asp Thr Leu Met Ile Ser Arg Thr Pro Glu Val Thr Cys Val
                        20                  25                  30

Val Val Asp Val Ser His Glu Asp Pro Glu Val Lys Phe Asn Trp Tyr
                    35                  40                  45

Val Asp Gly Val Glu Val His Asn Ala Lys Thr Lys Pro Arg Glu Glu
            50                  55                  60

Gln Tyr Xaa Ser Thr Tyr Arg Val Val Ser Val Leu Thr Val Leu His
        65                  70                  75                  80

Gln Asp Trp Leu Asn Gly Lys Glu Tyr Lys Cys Lys Val Ser Asn Lys
                            85                  90                  95

Ala Leu Pro Ala Pro Ile Glu Lys Thr Ile Ser Lys Ala Lys Gly Gln
                        100                 105                 110

Pro Arg Glu Pro Gln Val Tyr Thr Leu Pro Pro Ser Arg Asp Glu Leu
                        115                 120                 125

Thr Lys Asn Gln Val Ser Leu Thr Cys Leu Val Lys Gly Phe Tyr Pro
                    130                 135                 140

Ser Asp Ile Ala Val Glu Trp Glu Ser Asn Gly Gln Pro Glu Asn Asn
        145                 150                 155                 160

Tyr Lys Thr Thr Pro Pro Val Leu Asp Ser Asp Gly Ser Phe Phe Leu
```

```
                165                 170                 175
Tyr Ser Lys Leu Thr Val Asp Lys Ser Arg Trp Gln Gln Gly Asn Val
            180                 185                 190

Phe Ser Cys Ser Val Met His Glu Ala Leu His Asn His Tyr Thr Gln
        195                 200                 205

Lys Ser Leu Ser Leu Ser Pro Gly
    210                 215

<210> SEQ ID NO 65
<211> LENGTH: 193
<212> TYPE: PRT
<213> ORGANISM: Homo sapiens
<220> FEATURE:
<221> NAME/KEY: SITE
<222> LOCATION: (1)..(193)
<223> OTHER INFORMATION: Human EPO protein

<400> SEQUENCE: 65

Met Gly Val His Glu Cys Pro Ala Trp Leu Trp Leu Leu Ser Leu
1               5                   10                  15

Leu Leu Ser Leu Pro Leu Gly Leu Pro Val Leu Gly Ala Pro Pro Arg
            20                  25                  30

Leu Ile Cys Asp Ser Arg Val Leu Glu Arg Tyr Leu Leu Glu Ala Lys
        35                  40                  45

Glu Ala Glu Asn Ile Thr Thr Gly Cys Ala Glu His Cys Ser Leu Asn
50                  55                  60

Glu Asn Ile Thr Val Pro Asp Thr Lys Val Asn Phe Tyr Ala Trp Lys
65                  70                  75                  80

Arg Met Glu Val Gly Gln Gln Ala Val Glu Val Trp Gln Gly Leu Ala
                85                  90                  95

Leu Leu Ser Glu Ala Val Leu Arg Gly Gly Ala Leu Leu Val Asn Ser
            100                 105                 110

Ser Gln Pro Trp Glu Pro Leu Gln Leu His Val Asp Lys Ala Val Ser
        115                 120                 125

Gly Leu Gly Ser Leu Thr Thr Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 66
<211> LENGTH: 419
<212> TYPE: PRT
<213> ORGANISM: Artificial Sequence
<220> FEATURE:
<223> OTHER INFORMATION: Erythropoietin Single Chain Fc Fusion Protein
      (EPO-sFc)
<220> FEATURE:
<221> NAME/KEY: SITE
<222> LOCATION: (1)..(419)
<223> OTHER INFORMATION: Erythropoietin single chain Fc Fusion Protein
      (EPO-sFc)
<220> FEATURE:
<221> NAME/KEY: SITE
<222> LOCATION: (1)..(193)
<223> OTHER INFORMATION: Erythropoietin (EPO)
<220> FEATURE:
```

```
<221> NAME/KEY: SITE
<222> LOCATION: (194)..(203)
<223> OTHER INFORMATION: Mutated Hinge Region
<220> FEATURE:
<221> NAME/KEY: SITE
<222> LOCATION: (204)..(419)
<223> OTHER INFORMATION: Single Chain Fc Region (sFc)

<400> SEQUENCE: 66
```

| | | | | | | | | | | | | | | |
|---|---|---|---|---|---|---|---|---|---|---|---|---|---|---|
| Met | Gly | Val | His | Glu | Cys | Pro | Ala | Trp | Leu | Trp | Leu | Leu | Ser | Leu |
| 1 | | | | 5 | | | | | 10 | | | | | 15 |

| Leu | Leu | Ser | Leu | Pro | Leu | Gly | Leu | Pro | Val | Leu | Gly | Ala | Pro | Pro | Arg |
|---|---|---|---|---|---|---|---|---|---|---|---|---|---|---|---|
| | | | 20 | | | | | 25 | | | | | 30 | | |

| Leu | Ile | Cys | Asp | Ser | Arg | Val | Leu | Glu | Arg | Tyr | Leu | Leu | Glu | Ala | Lys |
|---|---|---|---|---|---|---|---|---|---|---|---|---|---|---|---|
| | | | 35 | | | | | 40 | | | | | 45 | | |

| Glu | Ala | Glu | Asn | Ile | Thr | Thr | Gly | Cys | Ala | Glu | His | Cys | Ser | Leu | Asn |
|---|---|---|---|---|---|---|---|---|---|---|---|---|---|---|---|
| | 50 | | | | | 55 | | | | | 60 | | | | |

| Glu | Asn | Ile | Thr | Val | Pro | Asp | Thr | Lys | Val | Asn | Phe | Tyr | Ala | Trp | Lys |
|---|---|---|---|---|---|---|---|---|---|---|---|---|---|---|---|
| 65 | | | | | 70 | | | | | 75 | | | | | 80 |

| Arg | Met | Glu | Val | Gly | Gln | Gln | Ala | Val | Glu | Val | Trp | Gln | Gly | Leu | Ala |
|---|---|---|---|---|---|---|---|---|---|---|---|---|---|---|---|
| | | | | 85 | | | | | 90 | | | | | 95 | |

| Leu | Leu | Ser | Glu | Ala | Val | Leu | Arg | Gly | Gly | Ala | Leu | Leu | Val | Asn | Ser |
|---|---|---|---|---|---|---|---|---|---|---|---|---|---|---|---|
| | | | 100 | | | | | 105 | | | | | 110 | | |

| Ser | Gln | Pro | Trp | Glu | Pro | Leu | Gln | Leu | His | Val | Asp | Lys | Ala | Val | Ser |
|---|---|---|---|---|---|---|---|---|---|---|---|---|---|---|---|
| | | | 115 | | | | | 120 | | | | | 125 | | |

| Gly | Leu | Gly | Ser | Leu | Thr | Thr | Leu | Arg | Ala | Leu | Gly | Ala | Gln | Lys | Glu |
|---|---|---|---|---|---|---|---|---|---|---|---|---|---|---|---|
| | 130 | | | | | 135 | | | | | 140 | | | | |

| Ala | Ile | Ser | Pro | Pro | Asp | Ala | Ala | Ser | Ala | Ala | Pro | Leu | Arg | Thr | Ile |
|---|---|---|---|---|---|---|---|---|---|---|---|---|---|---|---|
| 145 | | | | | 150 | | | | | 155 | | | | | 160 |

| Thr | Ala | Asp | Thr | Phe | Arg | Lys | Leu | Phe | Arg | Val | Tyr | Ser | Asn | Phe | Leu |
|---|---|---|---|---|---|---|---|---|---|---|---|---|---|---|---|
| | | | | 165 | | | | | 170 | | | | | 175 | |

| Arg | Gly | Lys | Leu | Lys | Leu | Tyr | Thr | Gly | Glu | Ala | Cys | Arg | Thr | Gly | Asp |
|---|---|---|---|---|---|---|---|---|---|---|---|---|---|---|---|
| | | | 180 | | | | | 185 | | | | | 190 | | |

| Arg | Asp | Lys | Thr | His | Thr | Ser | Pro | Ser | Pro | Ala | Pro | Glu | Leu | Leu |
|---|---|---|---|---|---|---|---|---|---|---|---|---|---|---|
| | | 195 | | | | | 200 | | | | | 205 | | |

| Gly | Gly | Pro | Ser | Val | Phe | Leu | Phe | Pro | Pro | Lys | Pro | Lys | Asp | Thr | Leu |
|---|---|---|---|---|---|---|---|---|---|---|---|---|---|---|---|
| | 210 | | | | | 215 | | | | | 220 | | | | |

| Met | Ile | Ser | Arg | Thr | Pro | Glu | Val | Thr | Cys | Val | Val | Val | Asp | Val | Ser |
|---|---|---|---|---|---|---|---|---|---|---|---|---|---|---|---|
| 225 | | | | | 230 | | | | | 235 | | | | | 240 |

| His | Glu | Asp | Pro | Glu | Val | Lys | Phe | Asn | Trp | Tyr | Val | Asp | Gly | Val | Glu |
|---|---|---|---|---|---|---|---|---|---|---|---|---|---|---|---|
| | | | | 245 | | | | | 250 | | | | | 255 | |

| Val | His | Asn | Ala | Lys | Thr | Lys | Pro | Arg | Glu | Glu | Gln | Tyr | His | Ser | Thr |
|---|---|---|---|---|---|---|---|---|---|---|---|---|---|---|---|
| | | | 260 | | | | | 265 | | | | | 270 | | |

| Tyr | Arg | Val | Val | Ser | Val | Leu | Thr | Val | Leu | His | Gln | Asp | Trp | Leu | Asn |
|---|---|---|---|---|---|---|---|---|---|---|---|---|---|---|---|
| | | 275 | | | | | 280 | | | | | 285 | | | |

| Gly | Lys | Glu | Tyr | Lys | Cys | Lys | Val | Ser | Asn | Lys | Ala | Leu | Pro | Ala | Pro |
|---|---|---|---|---|---|---|---|---|---|---|---|---|---|---|---|
| | 290 | | | | | 295 | | | | | 300 | | | | |

| Ile | Glu | Lys | Thr | Ile | Ser | Lys | Ala | Lys | Gly | Gln | Pro | Arg | Glu | Pro | Gln |
|---|---|---|---|---|---|---|---|---|---|---|---|---|---|---|---|
| 305 | | | | | 310 | | | | | 315 | | | | | 320 |

| Val | Tyr | Thr | Leu | Pro | Pro | Ser | Arg | Asp | Glu | Leu | Thr | Lys | Asn | Gln | Val |
|---|---|---|---|---|---|---|---|---|---|---|---|---|---|---|---|
| | | | | 325 | | | | | 330 | | | | | 335 | |

| Ser | Leu | Thr | Cys | Leu | Val | Lys | Gly | Phe | Tyr | Pro | Ser | Asp | Ile | Ala | Val |
|---|---|---|---|---|---|---|---|---|---|---|---|---|---|---|---|
| | | | 340 | | | | | 345 | | | | | 350 | | |

| Glu | Trp | Glu | Ser | Asn | Gly | Gln | Pro | Glu | Asn | Asn | Tyr | Lys | Thr | Thr | Pro |
|---|---|---|---|---|---|---|---|---|---|---|---|---|---|---|---|
| | | | 355 | | | | | 360 | | | | | 365 | | |

```
Pro Val Leu Asp Ser Asp Gly Ser Phe Phe Leu Tyr Ser Lys Leu Thr
    370             375                 380

Val Asp Lys Ser Arg Trp Gln Gln Gly Asn Val Phe Ser Cys Ser Val
385             390                 395                 400

Met His Glu Ala Leu His Asn His Tyr Thr Gln Lys Ser Leu Ser Leu
            405                 410                 415

Ser Pro Gly

<210> SEQ ID NO 67
<211> LENGTH: 461
<212> TYPE: PRT
<213> ORGANISM: Homo sapiens
<220> FEATURE:
<221> NAME/KEY: SITE
<222> LOCATION: (1)..(461)
<223> OTHER INFORMATION: Human Factor IX protein

<400> SEQUENCE: 67

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Ala Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300
```

```
Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
            325                 330                 335

Ala Asp Lys Glu Tyr Thr Asn Ile Phe Leu Lys Phe Gly Ser Gly Tyr
        340                 345                 350

Val Ser Gly Trp Gly Arg Val Phe His Lys Gly Arg Ser Ala Leu Val
    355                 360                 365

Leu Gln Tyr Leu Arg Val Pro Leu Val Asp Arg Ala Thr Cys Leu Arg
370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
            405                 410                 415

Thr Glu Val Glu Gly Thr Ser Phe Leu Thr Gly Ile Ile Ser Trp Gly
        420                 425                 430

Glu Glu Cys Ala Met Lys Gly Lys Tyr Gly Ile Tyr Thr Lys Val Ser
    435                 440                 445

Arg Tyr Val Asn Trp Ile Lys Glu Lys Thr Lys Leu Thr
450                 455                 460

<210> SEQ ID NO 68
<211> LENGTH: 692
<212> TYPE: PRT
<213> ORGANISM: Artificial Sequence
<220> FEATURE:
<223> OTHER INFORMATION: Factor IX Single Chain Fc Fusion Protein
      (FIX-sFc)
<220> FEATURE:
<221> NAME/KEY: SITE
<222> LOCATION: (1)..(692)
<223> OTHER INFORMATION: Factor IX single chain Fc Fusion Protein
      (FIX-sFc)
<220> FEATURE:
<221> NAME/KEY: SITE
<222> LOCATION: (1)..(461)
<223> OTHER INFORMATION: Factor IX (FIX)
<220> FEATURE:
<221> NAME/KEY: SITE
<222> LOCATION: (462)..(476)
<223> OTHER INFORMATION: Mutated Hinge Region
<220> FEATURE:
<221> NAME/KEY: SITE
<222> LOCATION: (477)..(692)
<223> OTHER INFORMATION: single chain Fc Region (sFc)

<400> SEQUENCE: 68

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110
```

-continued

```
Asn Ser Tyr Glu Cys Trp Cys Pro Phe Gly Phe Glu Gly Lys Asn Cys
            115                 120                 125
Glu Leu Asp Val Thr Cys Asn Ile Lys Asn Gly Arg Cys Glu Gln Phe
        130                 135                 140
Cys Lys Asn Ser Ala Asp Asn Lys Val Val Cys Ser Cys Thr Glu Gly
145                 150                 155                 160
Tyr Arg Leu Ala Glu Asn Gln Lys Ser Cys Glu Pro Ala Val Pro Phe
                165                 170                 175
Pro Cys Gly Arg Val Ser Val Ser Gln Thr Ser Lys Leu Thr Arg Ala
            180                 185                 190
Glu Ala Val Phe Pro Asp Val Asp Tyr Val Asn Ser Thr Glu Ala Glu
        195                 200                 205
Thr Ile Leu Asp Asn Ile Thr Gln Ser Thr Gln Ser Phe Asn Asp Phe
210                 215                 220
Thr Arg Val Val Gly Gly Glu Asp Ala Lys Pro Gly Gln Phe Pro Trp
225                 230                 235                 240
Gln Val Val Leu Asn Gly Lys Val Asp Ala Phe Cys Gly Gly Ser Ile
                245                 250                 255
Val Asn Glu Lys Trp Ile Val Thr Ala Ala His Cys Val Glu Thr Gly
            260                 265                 270
Val Lys Ile Thr Val Val Ala Gly Glu His Asn Ile Glu Glu Thr Glu
        275                 280                 285
His Thr Glu Gln Lys Arg Asn Val Ile Arg Ile Ile Pro His His Asn
        290                 295                 300
Tyr Asn Ala Ala Ile Asn Lys Tyr Asn His Asp Ile Ala Leu Leu Glu
305                 310                 315                 320
Leu Asp Glu Pro Leu Val Leu Asn Ser Tyr Val Thr Pro Ile Cys Ile
                325                 330                 335
Ala Asp Lys Glu Tyr Thr Asn Ile Phe Leu Lys Phe Gly Ser Gly Tyr
            340                 345                 350
Val Ser Gly Trp Gly Arg Val Phe His Lys Gly Arg Ser Ala Leu Val
        355                 360                 365
Leu Gln Tyr Leu Arg Val Pro Leu Val Asp Arg Ala Thr Cys Leu Arg
        370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
            420                 425                 430
Glu Glu Cys Ala Met Lys Gly Lys Tyr Gly Ile Tyr Thr Lys Val Ser
        435                 440                 445
Arg Tyr Val Asn Trp Ile Lys Glu Lys Thr Lys Leu Thr Glu Pro Lys
        450                 455                 460
Ser Ser Asp Lys Thr His Thr Ser Pro Pro Ser Pro Ala Pro Glu Leu
465                 470                 475                 480
Leu Gly Gly Pro Ser Val Phe Leu Phe Pro Pro Lys Pro Lys Asp Thr
                485                 490                 495
Leu Met Ile Ser Arg Thr Pro Glu Val Thr Cys Val Val Val Asp Val
            500                 505                 510
Ser His Glu Asp Pro Glu Val Lys Phe Asn Trp Tyr Val Asp Gly Val
        515                 520                 525
```

```
Glu Val His Asn Ala Lys Thr Lys Pro Arg Glu Glu Gln Tyr His Ser
            530                 535                 540

Thr Tyr Arg Val Val Ser Val Leu Thr Val Leu His Gln Asp Trp Leu
545                 550                 555                 560

Asn Gly Lys Glu Tyr Lys Cys Lys Val Ser Asn Lys Ala Leu Pro Ala
                565                 570                 575

Pro Ile Glu Lys Thr Ile Ser Lys Ala Lys Gly Gln Pro Arg Glu Pro
            580                 585                 590

Gln Val Tyr Thr Leu Pro Pro Ser Arg Asp Glu Leu Thr Lys Asn Gln
                595                 600                 605

Val Ser Leu Thr Cys Leu Val Lys Gly Phe Tyr Pro Ser Asp Ile Ala
610                 615                 620

Val Glu Trp Glu Ser Asn Gly Gln Pro Glu Asn Asn Tyr Lys Thr Thr
625                 630                 635                 640

Pro Pro Val Leu Asp Ser Asp Gly Ser Phe Phe Leu Tyr Ser Lys Leu
                645                 650                 655

Thr Val Asp Lys Ser Arg Trp Gln Gln Gly Asn Val Phe Ser Cys Ser
                660                 665                 670

Val Met His Glu Ala Leu His Asn His Tyr Thr Gln Lys Ser Leu Ser
            675                 680                 685

Leu Ser Pro Gly
            690

<210> SEQ ID NO 69
<211> LENGTH: 189
<212> TYPE: PRT
<213> ORGANISM: Homo sapiens
<220> FEATURE:
<221> NAME/KEY: SITE
<222> LOCATION: (1)..(189)
<223> OTHER INFORMATION: Interferon alpha 8 (IFNa8)

<400> SEQUENCE: 69

Met Ala Leu Thr Phe Tyr Leu Leu Val Ala Leu Val Val Leu Ser Tyr
1               5                   10                  15

Lys Ser Phe Ser Ser Leu Gly Cys Asp Leu Pro Gln Thr His Ser Leu
            20                  25                  30

Gly Asn Arg Arg Ala Leu Ile Leu Leu Ala Gln Met Arg Arg Ile Ser
        35                  40                  45

Pro Phe Ser Cys Leu Lys Asp Arg His Asp Phe Glu Phe Pro Gln Glu
    50                  55                  60

Glu Phe Asp Asp Lys Gln Phe Gln Lys Ala Gln Ala Ile Ser Val Leu
65                  70                  75                  80

His Glu Met Ile Gln Gln Thr Phe Asn Leu Phe Ser Thr Lys Asp Ser
                85                  90                  95

Ser Ala Ala Leu Asp Glu Thr Leu Leu Asp Glu Phe Tyr Ile Glu Leu
            100                 105                 110

Asp Gln Gln Leu Asn Asp Leu Glu Ser Cys Val Met Gln Glu Val Gly
        115                 120                 125

Val Ile Glu Ser Pro Leu Met Tyr Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Ser Cys Ala Trp Glu Val Val Arg Ala Glu Ile Met Arg Ser Phe Ser
                165                 170                 175

Leu Ser Ile Asn Leu Gln Lys Arg Leu Lys Ser Lys Glu
            180                 185
```

```
<210> SEQ ID NO 70
<211> LENGTH: 420
<212> TYPE: PRT
<213> ORGANISM: Artificial Sequence
<220> FEATURE:
<223> OTHER INFORMATION: Interferon alpha single chain fusion protein
      (IFNa-sFc)
<220> FEATURE:
<221> NAME/KEY: SITE
<222> LOCATION: (1)..(189)
<223> OTHER INFORMATION: Interferon alpha (IFNa)
<220> FEATURE:
<221> NAME/KEY: SITE
<222> LOCATION: (1)..(204)
<223> OTHER INFORMATION: Hinge Region
<220> FEATURE:
<221> NAME/KEY: SITE
<222> LOCATION: (205)..(420)
<223> OTHER INFORMATION: single chain Fc region (sFc)

<400> SEQUENCE: 70

Met Ala Leu Thr Phe Tyr Leu Leu Val Ala Leu Val Val Leu Ser Tyr
1               5                   10                  15

Lys Ser Phe Ser Ser Leu Gly Cys Asp Leu Pro Gln Thr His Ser Leu
            20                  25                  30

Gly Asn Arg Arg Ala Leu Ile Leu Leu Ala Gln Met Arg Arg Ile Ser
        35                  40                  45

Pro Phe Ser Cys Leu Lys Asp Arg His Asp Phe Glu Phe Pro Gln Glu
    50                  55                  60

Glu Phe Asp Asp Lys Gln Phe Gln Lys Ala Gln Ala Ile Ser Val Leu
65                  70                  75                  80

His Glu Met Ile Gln Gln Thr Phe Asn Leu Phe Ser Thr Lys Asp Ser
                85                  90                  95

Ser Ala Ala Leu Asp Glu Thr Leu Leu Asp Glu Phe Tyr Ile Glu Leu
            100                 105                 110

Asp Gln Gln Leu Asn Asp Leu Glu Ser Cys Val Met Gln Glu Val Gly
        115                 120                 125

Val Ile Glu Ser Pro Leu Met Tyr Glu Asp Ser Ile Leu Ala Val Arg
    130                 135                 140

Lys Tyr Phe Gln Arg Ile Thr Leu Tyr Leu Thr Glu Lys Lys Tyr Ser
145                 150                 155                 160

Ser Cys Ala Trp Glu Val Val Arg Ala Glu Ile Met Arg Ser Phe Ser
                165                 170                 175

Leu Ser Ile Asn Leu Gln Lys Arg Leu Lys Ser Lys Glu Glu Pro Lys
            180                 185                 190

Ser Ser Asp Lys Thr His Thr Ser Pro Pro Ser Pro Ala Pro Glu Leu
        195                 200                 205

Leu Gly Gly Pro Ser Val Phe Leu Phe Pro Pro Lys Pro Lys Asp Thr
    210                 215                 220

Leu Met Ile Ser Arg Thr Pro Glu Val Thr Cys Val Val Val Asp Val
225                 230                 235                 240

Ser His Glu Asp Pro Glu Val Lys Phe Asn Trp Tyr Val Asp Gly Val
                245                 250                 255

Glu Val His Asn Ala Lys Thr Lys Pro Arg Glu Glu Gln Tyr His Ser
            260                 265                 270

Thr Tyr Arg Val Val Ser Val Leu Thr Val Leu His Gln Asp Trp Leu
        275                 280                 285
```

```
Asn Gly Lys Glu Tyr Lys Cys Lys Val Ser Asn Lys Ala Leu Pro Ala
    290                 295                 300

Pro Ile Glu Lys Thr Ile Ser Lys Ala Lys Gly Gln Pro Arg Glu Pro
305                 310                 315                 320

Gln Val Tyr Thr Leu Pro Pro Ser Arg Asp Glu Leu Thr Lys Asn Gln
                325                 330                 335

Val Ser Leu Thr Cys Leu Val Lys Gly Phe Tyr Pro Ser Asp Ile Ala
                340                 345                 350

Val Glu Trp Glu Ser Asn Gly Gln Pro Glu Asn Asn Tyr Lys Thr Thr
                355                 360                 365

Pro Pro Val Leu Asp Ser Asp Gly Ser Phe Phe Leu Tyr Ser Lys Leu
370                 375                 380

Thr Val Asp Lys Ser Arg Trp Gln Gln Gly Asn Val Phe Ser Cys Ser
385                 390                 395                 400

Val Met His Glu Ala Leu His Asn His Tyr Thr Gln Lys Ser Leu Ser
                405                 410                 415

Leu Ser Pro Gly
            420

<210> SEQ ID NO 71
<211> LENGTH: 204
<212> TYPE: PRT
<213> ORGANISM: Homo sapiens
<220> FEATURE:
<221> NAME/KEY: SITE
<222> LOCATION: (1)..(204)
<223> OTHER INFORMATION: Granulocyte-Colony Stimulating Factor (GCSF)

<400> SEQUENCE: 71

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
        115                 120                 125

Leu Gly Pro Thr Leu Asp Thr Leu Gln Leu Asp Val Ala Asp Phe Ala
130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro
        195                 200
```

```
<210> SEQ ID NO 72
<211> LENGTH: 435
<212> TYPE: PRT
<213> ORGANISM: Artificial Sequence
<220> FEATURE:
<223> OTHER INFORMATION: Granulocyte-Colony Stimulating Factor single
      chaing Fc Fusion Protein (GCSF-sFc)
<220> FEATURE:
<221> NAME/KEY: SITE
<222> LOCATION: (1)..(204)
<223> OTHER INFORMATION: Granulocyte-Colony Stimulating Factor (GCSF)
<220> FEATURE:
<221> NAME/KEY: SITE
<222> LOCATION: (205)..(219)
<223> OTHER INFORMATION: Mutated Hinge Region
<220> FEATURE:
<221> NAME/KEY: SITE
<222> LOCATION: (220)..(435)
<223> OTHER INFORMATION: Single chain Fc (sFc)

<400> SEQUENCE: 72

Met Ala Gly Pro Ala Thr Gln Ser Pro Met Lys Leu Met Ala Leu Gln
1               5                   10                  15

Leu Leu Leu Trp His Ser Ala Leu Trp Thr Val Gln Glu Ala Thr Pro
            20                  25                  30

Leu Gly Pro Ala Ser Ser Leu Pro Gln Ser Phe Leu Leu Lys Cys Leu
        35                  40                  45

Glu Gln Val Arg Lys Ile Gln Gly Asp Gly Ala Ala Leu Gln Glu Lys
    50                  55                  60

Leu Cys Ala Thr Tyr Lys Leu Cys His Pro Glu Glu Leu Val Leu Leu
65                  70                  75                  80

Gly His Ser Leu Gly Ile Pro Trp Ala Pro Leu Ser Ser Cys Pro Ser
                85                  90                  95

Gln Ala Leu Gln Leu Ala Gly Cys Leu Ser Gln Leu His Ser Gly Leu
            100                 105                 110

Phe Leu Tyr Gln Gly Leu Leu Gln Ala Leu Glu Gly Ile Ser Pro Glu
        115                 120                 125

Leu Gly Pro Thr Leu Asp Thr Leu Gln Leu Asp Val Ala Asp Phe Ala
    130                 135                 140

Thr Thr Ile Trp Gln Gln Met Glu Glu Leu Gly Met Ala Pro Ala Leu
145                 150                 155                 160

Gln Pro Thr Gln Gly Ala Met Pro Ala Phe Ala Ser Ala Phe Gln Arg
                165                 170                 175

Arg Ala Gly Gly Val Leu Val Ala Ser His Leu Gln Ser Phe Leu Glu
            180                 185                 190

Val Ser Tyr Arg Val Leu Arg His Leu Ala Gln Pro Glu Pro Lys Ser
        195                 200                 205

Ser Asp Lys Thr His Thr Ser Pro Pro Ser Pro Ala Pro Glu Leu Leu
    210                 215                 220

Gly Gly Pro Ser Val Phe Leu Phe Pro Pro Lys Pro Lys Asp Thr Leu
225                 230                 235                 240

Met Ile Ser Arg Thr Pro Glu Val Thr Cys Val Val Val Asp Val Ser
                245                 250                 255

His Glu Asp Pro Glu Val Lys Phe Asn Trp Tyr Val Asp Gly Val Glu
            260                 265                 270

Val His Asn Ala Lys Thr Lys Pro Arg Glu Glu Gln Tyr His Ser Thr
        275                 280                 285

Tyr Arg Val Val Ser Val Leu Thr Val Leu His Gln Asp Trp Leu Asn
    290                 295                 300
```

```
Gly Lys Glu Tyr Lys Cys Lys Val Ser Asn Lys Ala Leu Pro Ala Pro
305                 310                 315                 320

Ile Glu Lys Thr Ile Ser Lys Ala Lys Gly Gln Pro Arg Glu Pro Gln
            325                 330                 335

Val Tyr Thr Leu Pro Pro Ser Arg Asp Glu Leu Thr Lys Asn Gln Val
            340                 345                 350

Ser Leu Thr Cys Leu Val Lys Gly Phe Tyr Pro Ser Asp Ile Ala Val
            355                 360                 365

Glu Trp Glu Ser Asn Gly Gln Pro Glu Asn Asn Tyr Lys Thr Thr Pro
370                 375                 380

Pro Val Leu Asp Ser Asp Gly Ser Phe Phe Leu Tyr Ser Lys Leu Thr
385                 390                 395                 400

Val Asp Lys Ser Arg Trp Gln Gln Gly Asn Val Phe Ser Cys Ser Val
            405                 410                 415

Met His Glu Ala Leu His Asn His Tyr Thr Gln Lys Ser Leu Ser Leu
            420                 425                 430

Ser Pro Gly
            435
```

<210> SEQ ID NO 73
<211> LENGTH: 187
<212> TYPE: PRT
<213> ORGANISM: Homo sapiens
<220> FEATURE:
<221> NAME/KEY: SITE
<222> LOCATION: (1)..(187)
<223> OTHER INFORMATION: Interferon beta (IFNb)

<400> SEQUENCE: 73

```
Met Asn Asn Arg Trp Ile Leu His Ala Ala Phe Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn
                180                 185
```

<210> SEQ ID NO 74
<211> LENGTH: 419
<212> TYPE: PRT

-continued

```
<213> ORGANISM: Artificial Sequence
<220> FEATURE:
<223> OTHER INFORMATION: Interferon beta single chain Fc Fusion Protein
      (IFNb-sFc)
<220> FEATURE:
<221> NAME/KEY: SITE
<222> LOCATION: (1)..(187)
<223> OTHER INFORMATION: Interferon beta (IFNb)
<220> FEATURE:
<221> NAME/KEY: SITE
<222> LOCATION: (188)..(202)
<223> OTHER INFORMATION: Mutated Hinge Region
<220> FEATURE:
<221> NAME/KEY: SITE
<222> LOCATION: (203)..(419)
<223> OTHER INFORMATION: Single chain Fc (sFc)

<400> SEQUENCE: 74
```

Met Asn Asn Arg Trp Ile Leu His Ala Ala Phe Leu Leu Cys Phe Ser
1               5                   10                  15

Thr Thr Ala Leu Ser Met Ser Tyr Asn Leu Leu Gly Phe Leu Gln Arg
            20                  25                  30

Ser Ser Asn Phe Gln Cys Gln Lys Leu Leu Trp Gln Leu Asn Gly Arg
        35                  40                  45

Leu Glu Tyr Cys Leu Lys Asp Arg Met Asn Phe Asp Ile Pro Glu Glu
    50                  55                  60

Ile Lys Gln Leu Gln Gln Phe Gln Lys Glu Asp Ala Ala Leu Thr Ile
65                  70                  75                  80

Tyr Glu Met Leu Gln Asn Ile Phe Ala Ile Phe Arg Gln Asp Ser Ser
                85                  90                  95

Ser Thr Gly Trp Asn Glu Thr Ile Val Glu Asn Leu Leu Ala Asn Val
            100                 105                 110

Tyr His Gln Ile Asn His Leu Lys Thr Val Leu Glu Glu Lys Leu Glu
        115                 120                 125

Lys Glu Asp Phe Thr Arg Gly Lys Leu Met Ser Ser Leu His Leu Lys
    130                 135                 140

Arg Tyr Tyr Gly Arg Ile Leu His Tyr Leu Lys Ala Lys Glu Tyr Ser
145                 150                 155                 160

His Cys Ala Trp Thr Ile Val Arg Val Glu Ile Leu Arg Asn Phe Tyr
                165                 170                 175

Phe Ile Asn Arg Leu Thr Gly Tyr Leu Arg Asn Glu Pro Lys Ser Ser
            180                 185                 190

Asp Lys Thr His Thr Ser Pro Pro Ser Pro Ala Pro Glu Leu Leu Gly
        195                 200                 205

Gly Pro Ser Val Phe Leu Phe Pro Pro Lys Pro Lys Asp Thr Leu Met
    210                 215                 220

Ile Ser Arg Thr Pro Glu Val Thr Cys Val Val Val Asp Val Ser His
225                 230                 235                 240

Glu Asp Pro Glu Val Lys Phe Asn Trp Tyr Val Asp Gly Val Glu Val
                245                 250                 255

His Asn Ala Lys Thr Lys Pro Arg Glu Glu Gln Tyr Ala Ser Thr Tyr
            260                 265                 270

Arg Val Val Ser Val Leu Thr Val Leu His Gln Asp Trp Leu Asn Gly
        275                 280                 285

Lys Glu Tyr Lys Cys Lys Val Ser Asn Lys Ala Leu Pro Ala Pro Ile
    290                 295                 300

Glu Lys Thr Ile Ser Lys Ala Lys Gly Gln Pro Arg Glu Pro Gln Val
305                 310                 315                 320

-continued

```
Tyr Thr Leu Pro Pro Ser Arg Asp Glu Leu Thr Lys Asn Gln Val Ser
            325                 330                 335

Leu Thr Cys Leu Val Lys Gly Phe Tyr Pro Ser Asp Ile Ala Val Glu
            340                 345                 350

Trp Glu Ser Asn Gly Gln Pro Glu Asn Asn Tyr Lys Thr Thr Pro Pro
            355                 360                 365

Val Leu Asp Ser Asp Gly Ser Phe Phe Leu Tyr Ser Lys Leu Thr Val
        370                 375                 380

Asp Lys Ser Arg Trp Gln Gln Gly Asn Val Phe Ser Cys Ser Val Met
385                 390                 395                 400

His Glu Ala Leu His Asn His Tyr Thr Gln Lys Ser Leu Ser Leu Ser
                405                 410                 415

Pro Gly Lys
```